(12) United States Patent
Kulesa et al.

(10) Patent No.: US 8,235,986 B2
(45) Date of Patent: Aug. 7, 2012

(54) SYSTEMS AND METHODS FOR TRANSEPTAL CARDIAC PROCEDURES, INCLUDING TISSUE PENETRATING MEMBERS AND ASSOCIATED METHODS

(75) Inventors: Larry B. Kulesa, Bothell, WA (US);
Ryan E. Kaveckis, Everett, WA (US);
David C. Auth, Kirkland, WA (US)

(73) Assignee: CoAptus Medical Corporation, Redmond, WA (US)

( * ) Notice: Subject to any disclaimer, the term of this patent is extended or adjusted under 35 U.S.C. 154(b) by 871 days.

(21) Appl. No.: 12/246,358

(22) Filed: Oct. 6, 2008

(65) Prior Publication Data
US 2009/0093802 A1    Apr. 9, 2009

Related U.S. Application Data

(60) Provisional application No. 60/977,837, filed on Oct. 5, 2007.

(51) Int. Cl.
*A61B 18/14* (2006.01)
(52) U.S. Cl. ......................................................... 606/41
(58) Field of Classification Search .................. 606/41, 606/49
See application file for complete search history.

(56) References Cited

U.S. PATENT DOCUMENTS

| | | | |
|---|---|---|---|
| 4,273,127 A | 6/1981 | Auth et al. | |
| 4,492,231 A | 1/1985 | Auth | |
| 4,532,924 A | 8/1985 | Auth et al. | |
| 4,582,057 A | 4/1986 | Auth et al. | |
| 4,682,596 A | 7/1987 | Bales et al. | |
| 4,921,484 A | 5/1990 | Hillstead | |
| 4,998,933 A | 3/1991 | Eggers et al. | |
| 5,035,696 A * | 7/1991 | Rydell | 606/47 |
| 5,290,278 A | 3/1994 | Anderson | |
| 5,300,065 A | 4/1994 | Anderson | |
| 5,342,357 A | 8/1994 | Nardella | |
| 5,364,389 A | 11/1994 | Anderson | |
| 5,364,393 A * | 11/1994 | Auth et al. | 606/34 |
| 5,403,311 A | 4/1995 | Abele et al. | |
| 5,421,338 A | 6/1995 | Crowley et al. | |
| 5,507,744 A | 4/1996 | Tay et al. | |

(Continued)

FOREIGN PATENT DOCUMENTS
WO    WO-99/18871    4/1999
(Continued)

OTHER PUBLICATIONS

European Search Report for European Application No. 08835914.6, Applicant: Coaptus Medical Corporation, mailed Apr. 8, 2011, 12 pages.

(Continued)

*Primary Examiner* — Michael Peffley
*Assistant Examiner* — Daniel Fowler
(74) *Attorney, Agent, or Firm* — Perkins Coie LLP

(57) ABSTRACT

Systems and methods for transeptal cardiac procedures are disclosed. A method for treating a patient in accordance with a particular embodiment includes positioning a tissue penetrating guidewire adjacent to a cardiac septum, directing pulses of energy to the guidewire, and advancing the guidewire into and through the septum by moving the guidewire in a distal direction in a series of discrete steps. Individual steps can be of a predetermined distance measured outside the patient's body. The method can further include passing a catheter over the guidewire after the guidewire has passed through the septum.

40 Claims, 37 Drawing Sheets

U.S. PATENT DOCUMENTS

| | | |
|---|---|---|
| 5,522,873 A | 6/1996 | Jackman et al. |
| 5,558,671 A | 9/1996 | Yates |
| 5,571,088 A | 11/1996 | Lennox et al. |
| 5,584,872 A | 12/1996 | LaFontaine et al. |
| 5,607,462 A | 3/1997 | Imran |
| 5,643,171 A | 7/1997 | Bradshaw et al. |
| 5,662,647 A | 9/1997 | Crow et al. |
| 5,680,860 A | 10/1997 | Imran |
| 5,709,224 A | 1/1998 | Behl et al. |
| 5,725,552 A | 3/1998 | Kotula et al. |
| 5,782,860 A | 7/1998 | Epstein et al. |
| 5,810,810 A | 9/1998 | Tay et al. |
| 5,827,268 A | 10/1998 | Laufer |
| 5,919,200 A | 7/1999 | Stambaugh et al. |
| 5,944,738 A | 8/1999 | Amplatz et al. |
| 5,972,026 A | 10/1999 | Laufer et al. |
| 5,989,284 A | 11/1999 | Laufer |
| 6,004,269 A | 12/1999 | Crowley et al. |
| 6,030,380 A | 2/2000 | Auth et al. |
| 6,033,397 A | 3/2000 | Laufer et al. |
| 6,033,398 A | 3/2000 | Farley et al. |
| 6,036,687 A | 3/2000 | Laufer et al. |
| 6,063,081 A | 5/2000 | Mulier et al. |
| 6,063,085 A | 5/2000 | Tay et al. |
| 6,068,653 A | 5/2000 | LaFontaine |
| 6,090,063 A | 7/2000 | Makower et al. |
| 6,091,995 A | 7/2000 | Ingle et al. |
| 6,106,520 A | 8/2000 | Laufer et al. |
| 6,112,123 A | 8/2000 | Kelleher et al. |
| 6,129,726 A | 10/2000 | Edwards et al. |
| 6,132,429 A | 10/2000 | Baker |
| 6,135,997 A | 10/2000 | Laufer et al. |
| 6,179,824 B1 | 1/2001 | Eggers et al. |
| 6,200,333 B1 | 3/2001 | Laufer |
| 6,212,426 B1 | 4/2001 | Swanson |
| 6,221,068 B1 | 4/2001 | Fried et al. |
| 6,231,570 B1 | 5/2001 | Tu et al. |
| 6,235,021 B1 | 5/2001 | Sieben |
| 6,238,389 B1 | 5/2001 | Paddock et al. |
| 6,254,598 B1 | 7/2001 | Edwards et al. |
| 6,258,087 B1 | 7/2001 | Edwards et al. |
| 6,283,988 B1 | 9/2001 | Laufer et al. |
| 6,283,989 B1 | 9/2001 | Laufer et al. |
| 6,290,674 B1 | 9/2001 | Roue et al. |
| 6,355,030 B1 | 3/2002 | Aldrich et al. |
| 6,398,779 B1 | 6/2002 | Buysse et al. |
| 6,398,782 B1 | 6/2002 | Pecor et al. |
| 6,401,720 B1 | 6/2002 | Stevens et al. |
| 6,428,538 B1 * | 8/2002 | Blewett et al. .................. 606/46 |
| 6,488,673 B1 | 12/2002 | Laufer et al. |
| 6,527,769 B2 | 3/2003 | Langberg et al. |
| 6,529,756 B1 | 3/2003 | Phan et al. |
| 6,546,934 B1 | 4/2003 | Ingle et al. |
| 6,547,776 B1 | 4/2003 | Gaiser et al. |
| 6,606,513 B2 | 8/2003 | Lardo et al. |
| 6,629,534 B1 | 10/2003 | St. Goar et al. |
| 6,652,517 B1 | 11/2003 | Hall et al. |
| 6,712,814 B2 | 3/2004 | Edwards et al. |
| 6,733,498 B2 | 5/2004 | Paton et al. |
| 6,775,575 B2 | 8/2004 | Bommannan et al. |
| 6,783,523 B2 | 8/2004 | Qin et al. |
| 6,836,688 B2 | 12/2004 | Ingle et al. |
| 6,837,886 B2 | 1/2005 | Collins et al. |
| 6,866,663 B2 | 3/2005 | Edwards et al. |
| 6,917,834 B2 | 7/2005 | Koblish et al. |
| 6,939,348 B2 | 9/2005 | Malecki et al. |
| 7,027,869 B2 | 4/2006 | Danek et al. |
| 7,044,134 B2 | 5/2006 | Khairkhahan et al. |
| 7,048,733 B2 | 5/2006 | Hartley et al. |
| 7,112,197 B2 | 9/2006 | Hartley et al. |
| 7,122,043 B2 | 10/2006 | Greenhalgh et al. |
| 7,165,551 B2 | 1/2007 | Edwards et al. |
| 7,165,552 B2 | 1/2007 | Deem et al. |
| 7,186,251 B2 | 3/2007 | Malecki et al. |
| 7,220,265 B2 | 5/2007 | Chanduszko et al. |
| 7,257,450 B2 | 8/2007 | Auth et al. |
| 7,270,662 B2 | 9/2007 | Visram et al. |
| 7,293,562 B2 | 11/2007 | Malecki et al. |
| 7,306,594 B2 | 12/2007 | Collins et al. |
| 7,338,514 B2 | 3/2008 | Wahr et al. |
| 7,367,975 B2 | 5/2008 | Malecki et al. |
| 7,473,252 B2 | 1/2009 | Barry |
| 2002/0042564 A1 | 4/2002 | Cooper et al. |
| 2002/0107512 A1 | 8/2002 | Edwards |
| 2003/0208232 A1 | 11/2003 | Blaeser et al. |
| 2004/0143262 A1 | 7/2004 | Visram et al. |
| 2004/0187875 A1 * | 9/2004 | He et al. ........................ 128/898 |
| 2004/0243122 A1 | 12/2004 | Auth et al. |
| 2004/0267191 A1 | 12/2004 | Gifford et al. |
| 2005/0033288 A1 | 2/2005 | Auth et al. |
| 2005/0131460 A1 | 6/2005 | Gifford et al. |
| 2005/0192654 A1 | 9/2005 | Chanduszko et al. |
| 2006/0052821 A1 | 3/2006 | Abbott et al. |
| 2006/0142756 A1 | 6/2006 | Davies et al. |
| 2006/0200197 A1 | 9/2006 | Brenzel et al. |
| 2006/0271030 A1 | 11/2006 | Francis et al. |
| 2007/0021739 A1 | 1/2007 | Weber |
| 2007/0043318 A1 | 2/2007 | Sogard et al. |
| 2007/0055333 A1 | 3/2007 | Forde et al. |
| 2007/0060858 A1 | 3/2007 | Sogard et al. |
| 2007/0088355 A9 | 4/2007 | Auth et al. |
| 2007/0093804 A1 | 4/2007 | Kaveckis et al. |
| 2007/0112358 A1 | 5/2007 | Abbott et al. |
| 2007/0123851 A1 | 5/2007 | Alejandro et al. |
| 2007/0123852 A1 | 5/2007 | Deem et al. |
| 2007/0123932 A1 | 5/2007 | Gray et al. |
| 2007/0156123 A1 | 7/2007 | Moll et al. |
| 2007/0185530 A1 | 8/2007 | Chin-Chen et al. |
| 2007/0287999 A1 | 12/2007 | Malecki et al. |
| 2008/0015633 A1 | 1/2008 | Abbott et al. |
| 2008/0140064 A1 | 6/2008 | Vegesna |
| 2008/0140068 A1 | 6/2008 | Taimisto |
| 2008/0140074 A1 | 6/2008 | Horne et al. |
| 2008/0221566 A1 | 9/2008 | Krishnan |
| 2009/0005780 A1 | 1/2009 | Kato |
| 2009/0069809 A1 | 3/2009 | Ootsubo |
| 2009/0076525 A1 | 3/2009 | Kato et al. |
| 2009/0093802 A1 | 4/2009 | Kulesa et al. |
| 2009/0093803 A1 | 4/2009 | Herrin |
| 2009/0118726 A1 | 5/2009 | Auth et al. |
| 2009/0131925 A1 | 5/2009 | Tempel et al. |
| 2011/0087211 A1 | 4/2011 | Kulesa et al. |

FOREIGN PATENT DOCUMENTS

| | | |
|---|---|---|
| WO | WO-99/42044 A1 | 8/1999 |
| WO | WO-00/18308 | 4/2000 |
| WO | WO-00/51510 | 9/2000 |
| WO | WO-00/66015 | 11/2000 |
| WO | WO-01/17450 | 3/2001 |
| WO | WO-01/82814 | 11/2001 |
| WO | WO-02/058780 | 8/2002 |
| WO | WO-2005046487 A1 | 5/2005 |
| WO | WO-2006/110830 | 10/2006 |
| WO | WO-2007038609 A2 | 4/2007 |
| WO | WO-2007/092860 A2 | 8/2007 |
| WO | WO-2007092860 A2 | 8/2007 |
| WO | WO-2007140419 A2 | 12/2007 |
| WO | WO-2008079826 A2 | 7/2008 |
| WO | WO-2008/137649 A2 | 11/2008 |
| WO | WO-2008140419 A2 | 11/2008 |

OTHER PUBLICATIONS

NovaSure No Hormones. No Hysterectomy, "The NovaSure Procedure," http://www.novasure.com/novasure-procedure/novasure-procedure.cfm, A Hologic Company, accessed Sep. 18, 2008, 2 pages.

International Search Report and Written Opinion for International Patent Application No. PCT/US08/78980, Applicant: CoAptus Medical Corporation, mailing date: Feb. 6, 2009, 17 pages.

McMahon, C.J. et al., "Use of the Transseptal Puncture in transcatherer Closure of Long tunnel-type Patent foramen Ovale," Heart, Aug. 2002, 88:e3, (2 pages).

Ruiz, C. et al., "The Puncture Technique: A New Method for Transcatheter Closure of Patent Foramen Ovale," Catheterization and Cardiovascular Interventions, 2001, pp. 369-372, vol. 53, Wiley-Liss, Inc.

Szili-Torok, T. et al.-Transseptal Left Heart Catheterisation Guided by Intracardiac Echocardiography, Heart, 2001, 86:e11, Dept. of Cardiology, Rotterdam, The Netherlands. (5 Pages).

Skowasch, Marijke et al. Non-Device Closure (Radiofrequency, Sutures). CHD 2006. Jun. 8-10. Frankfurt. 19 Slides.

Sigel, Bernard et al. "Physical Factors in Electrocoaptation of Blood Vessels" Archives of Surgery, vol. 95, No. 1. Jul. 1967.

Circulation Arrhythmia and Electrophysiology, "Radiofrequency Puncture of the *Fossa ovalis* for Resistant Transseptal Access, Journal of the American Heart Association," 7 pages.

* cited by examiner

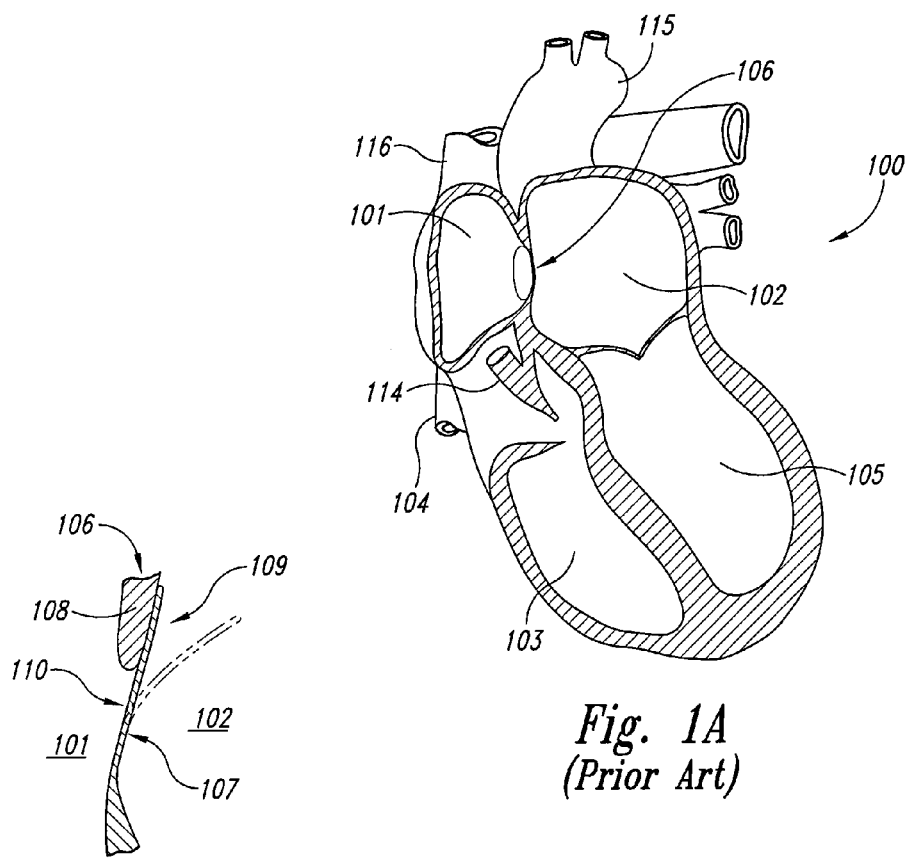
Fig. 1A
(Prior Art)
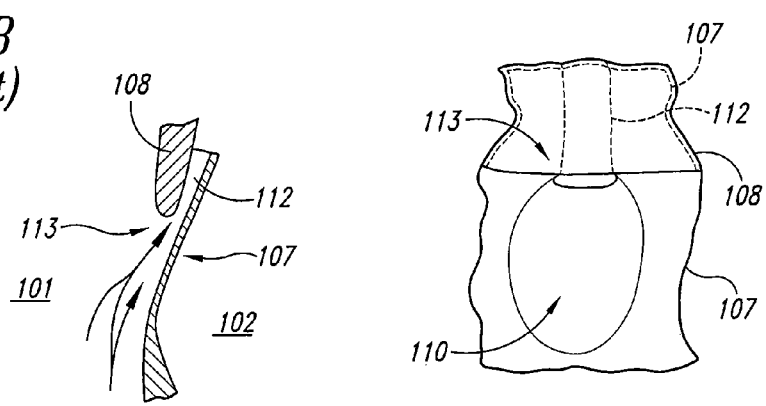
Fig. 1B
(Prior Art)
Fig. 1C
(Prior Art)
Fig. 1D
(Prior Art)

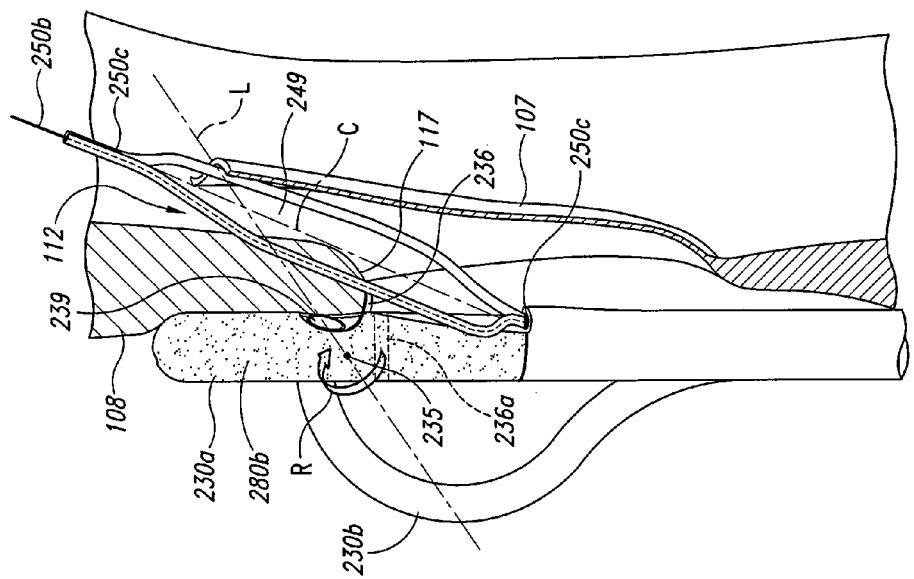
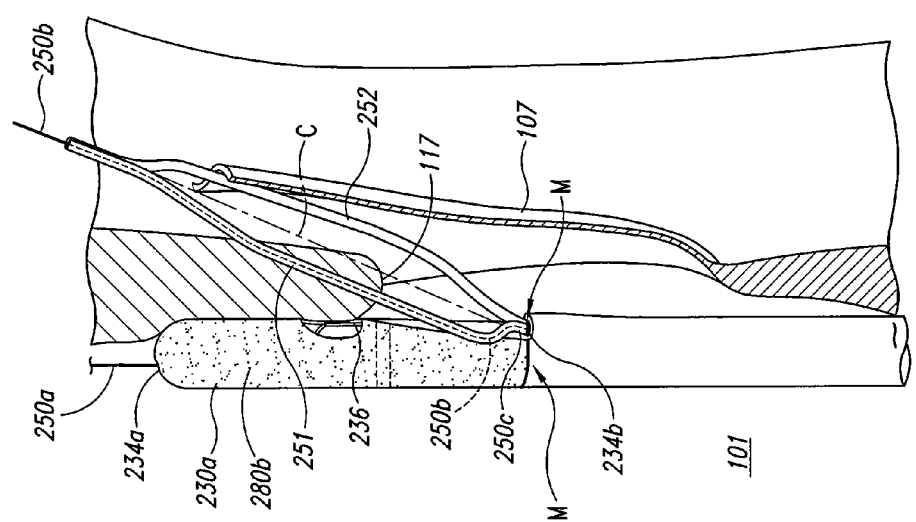

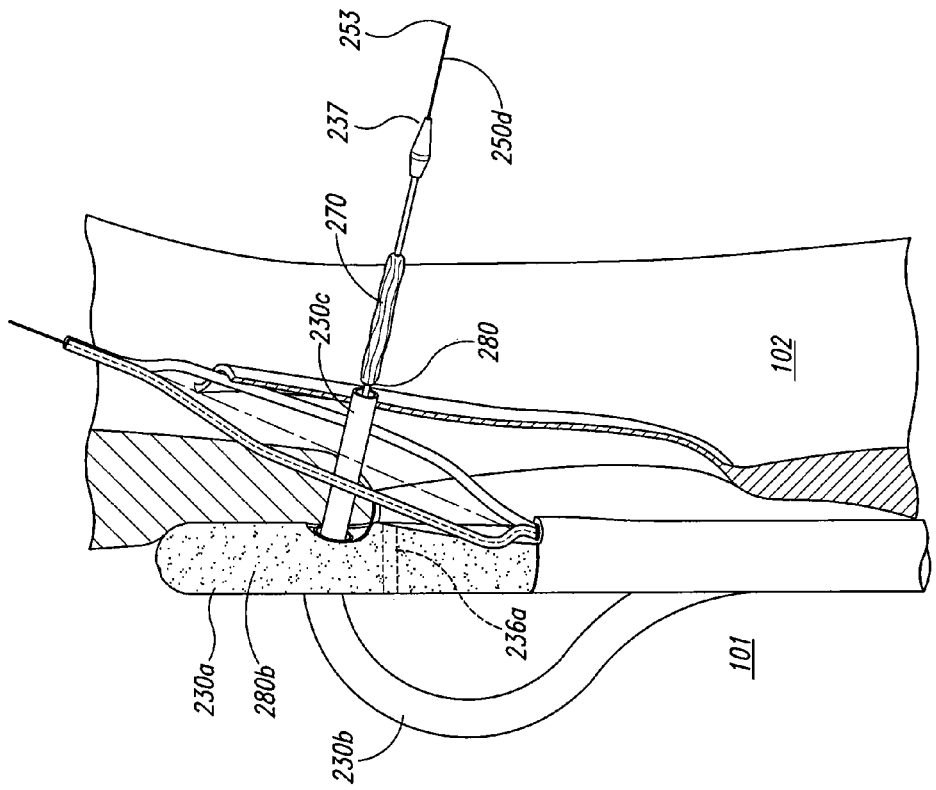
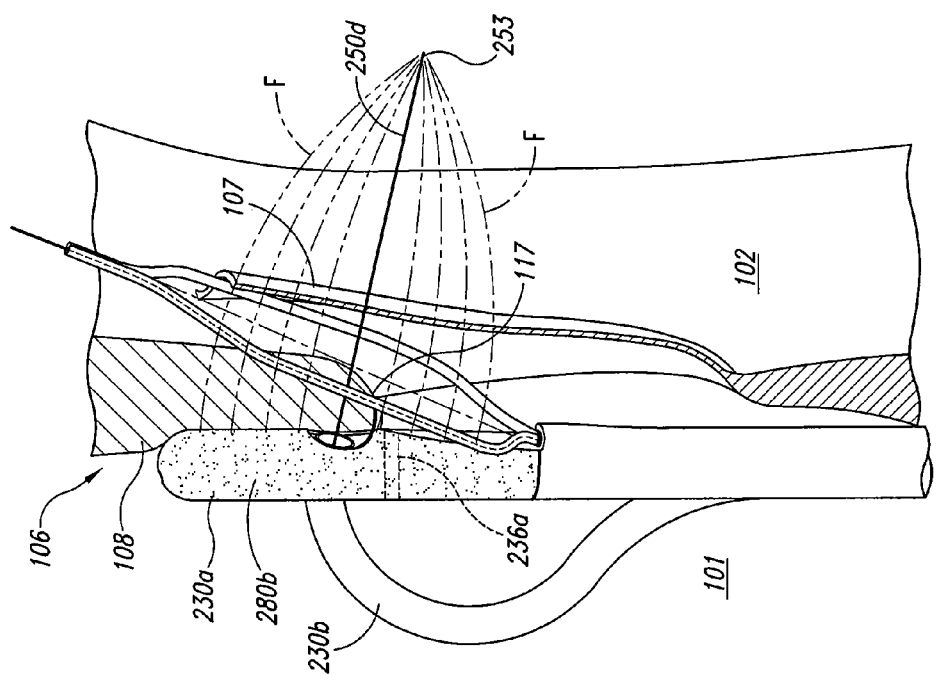

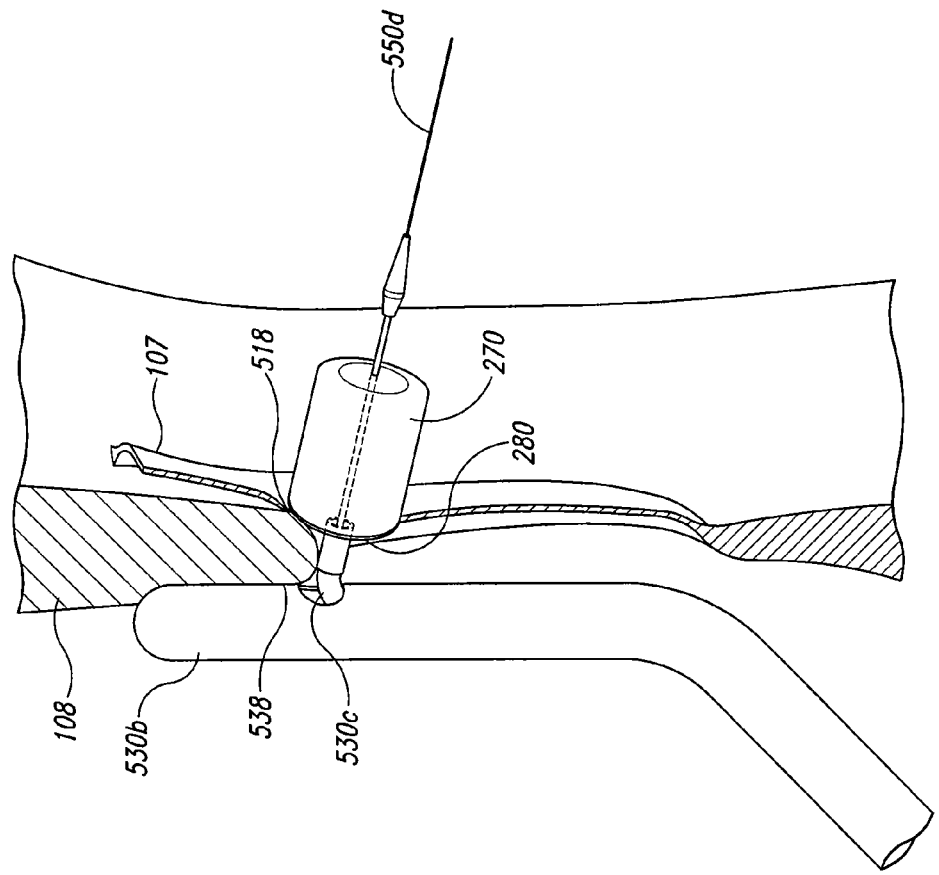
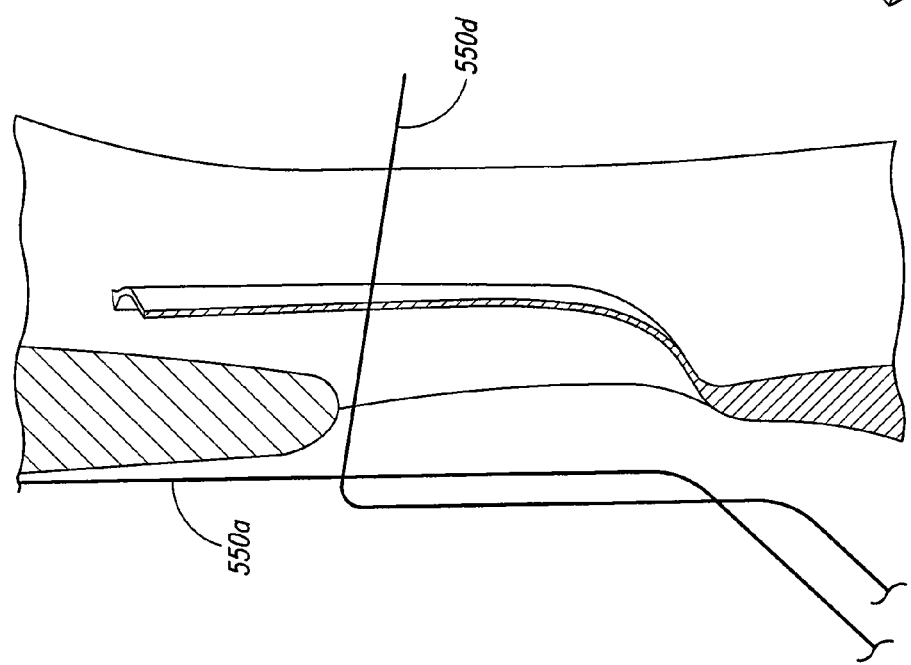
Fig. 5D
Fig. 5C

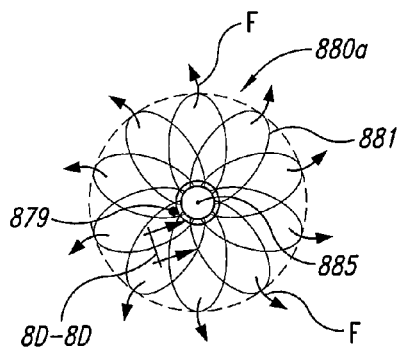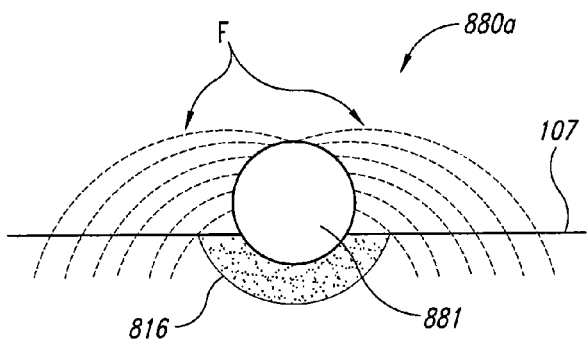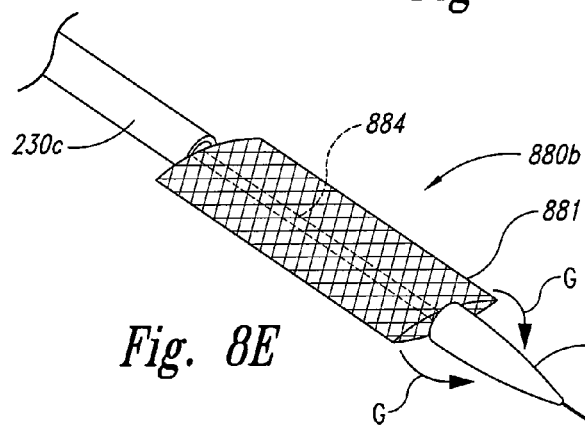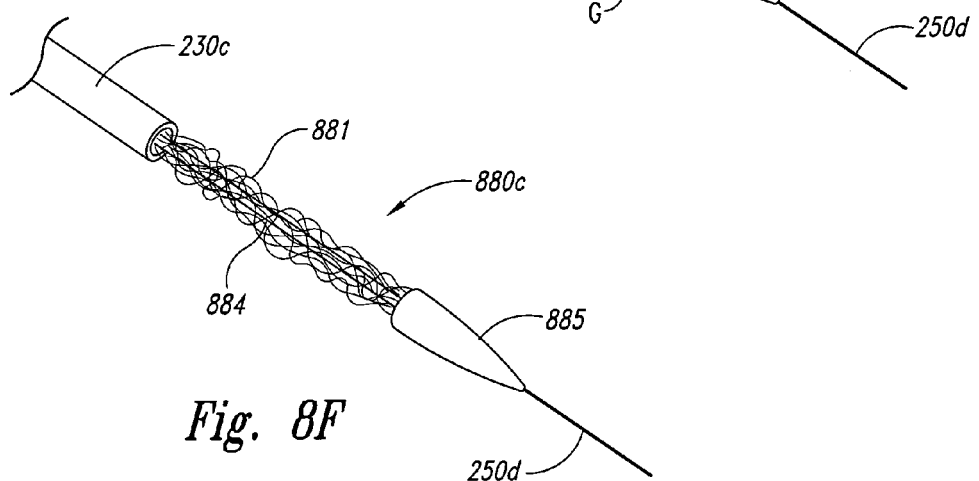

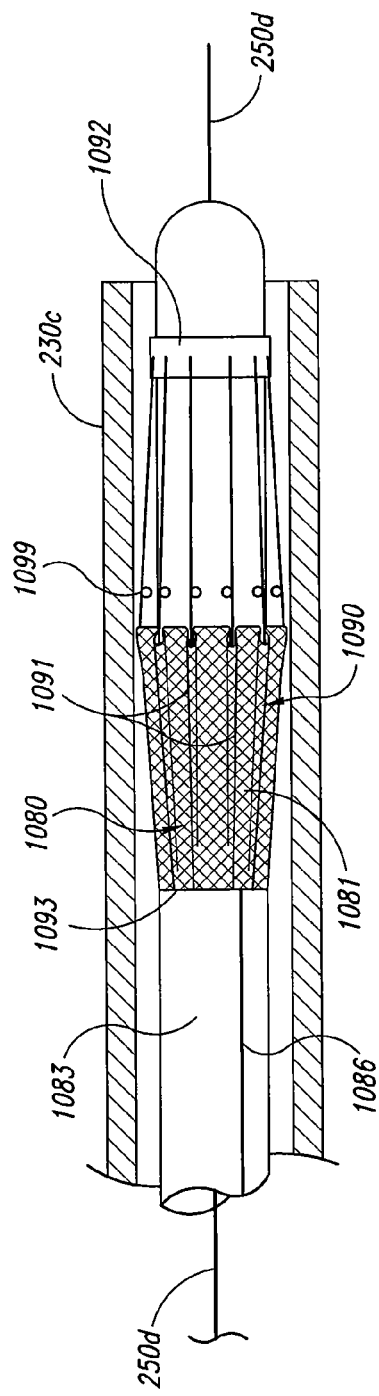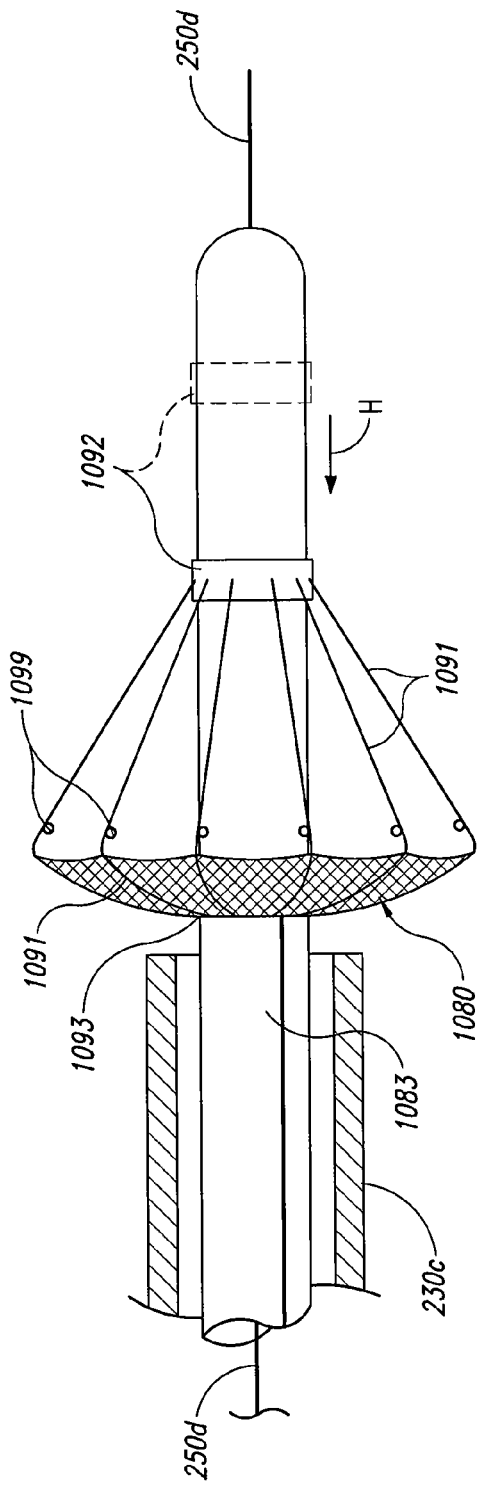

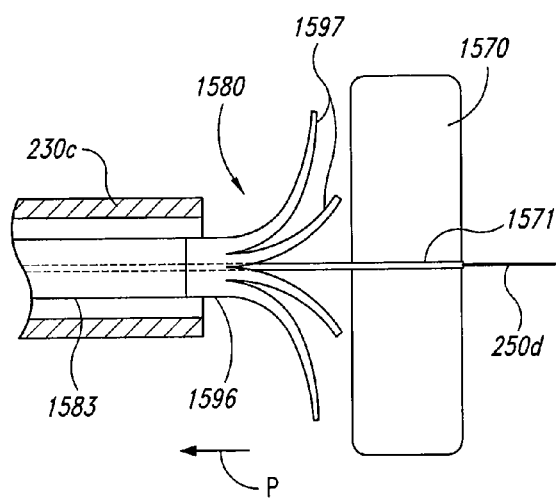
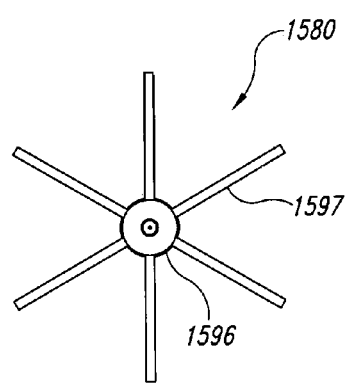
Fig. 15A　　　　　Fig. 15B
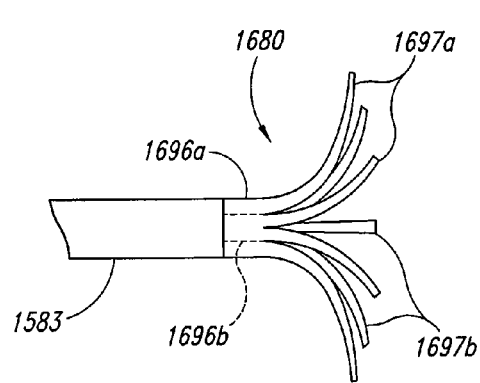
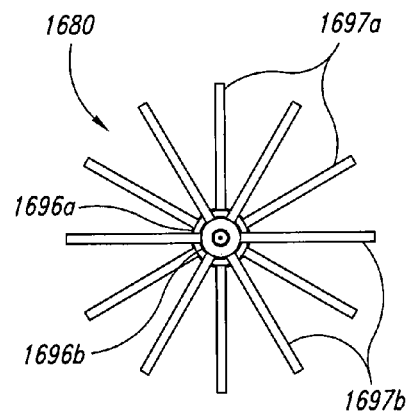
Fig. 16A　　　　　Fig. 16B

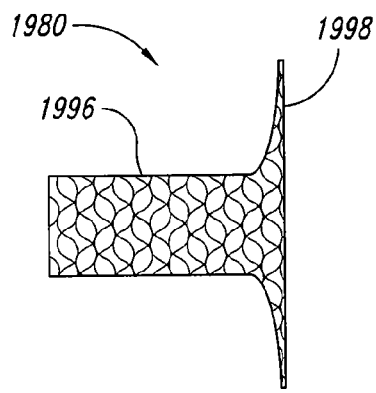
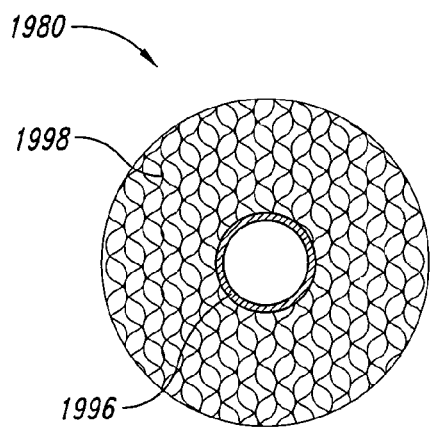
*Fig. 19A*  *Fig. 19B*
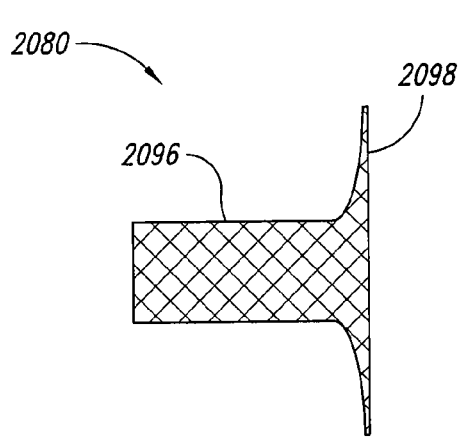
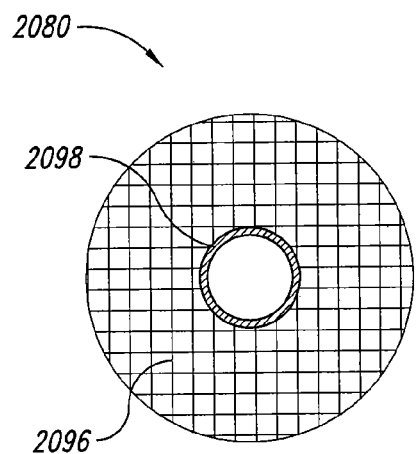
*Fig. 20A*  *Fig. 20B*

SYSTEMS AND METHODS FOR TRANSEPTAL CARDIAC PROCEDURES, INCLUDING TISSUE PENETRATING MEMBERS AND ASSOCIATED METHODS

CROSS-REFERENCE TO RELATED APPLICATION

The present application claims priority to U.S. Provisional Application No. 60/977,837, filed Oct. 5, 2007 and incorporated herein by reference.

TECHNICAL FIELD

The present disclosure is directed generally to systems and methods for transeptal cardiac procedures, including separable guidewires, tissue penetrating members, and tissue sealing members.

BACKGROUND

The human heart is a complex organ that requires reliable, fluid-tight seals to prevent de-oxygenated blood and other constituents received from the body's tissues from mixing with re-oxygenated blood delivered to the body's tissues. FIG. 1A illustrates a human heart 100 having a right atrium 101, which receives the de-oxygenated blood from the superior vena cava 116 and the inferior vena cava 104. The de-oxygenated blood passes to the right ventricle 103, which pumps the de-oxygenated blood to the lungs via the pulmonary artery 114. Re-oxygenated blood returns from the lungs to the left atrium 102 and is pumped into the left ventricle 105. From the left ventricle 105, the re-oxygenated blood is pumped throughout the body via the aorta 115.

The right atrium 101 and the left atrium 102 are separated by an interatrial septum 106. As shown in FIG. 1B, the interatrial septum 106 includes a primum 107 and a secundum 108. Prior to birth, the primum 107 and the secundum 108 are separated to form an opening (the foramen ovale 109) that allows blood to flow from the right atrium 101 to the left atrium 102 while the fetus receives oxygenated blood from the mother. After birth, the primum 107 normally seals against the secundum 108 and forms an oval-shaped depression, i.e., a fossa ovalis 110.

In some infants, the primum 107 never completely seals with the secundum 108, as shown in cross-sectional view in FIG. 1C and in a left side view in FIG. 1D. In these instances, a patency often having the shape of a tunnel 112 forms between the primum 107 and the secundum 108. This patency is typically referred to as a patent foramen ovale or PFO 113. In most circumstances, the PFO 113 will remain functionally closed and blood will not tend to flow through the PFO 113, due to the normally higher pressures in the left atrium 102 that secure the primum 107 against the secundum 108. Nevertheless, during physical exertion or other instances when pressures are greater in the right atrium 101 than in the left atrium 102, blood can inappropriately pass directly from the right atrium 101 to the left atrium 102 and can carry with it clots, gas bubbles, or other vaso-active substances. Such constituents in the atrial system can pose serious health risks including hemodynamic problems, cryptogenic strokes, venous-to-atrial gas embolisms, migraines, and in some cases even death.

Traditionally, open chest surgery was required to suture or ligate a PFO 113. However, these procedures carry high attendant risks, such as postoperative infection, long patient recovery, and significant patient discomfort and trauma. Accordingly, less invasive techniques have been developed. Most such techniques include using transcatheter implantation of various mechanical devices to close the PFO 113. Such devices include the Cardia® PFO Closure Device, Amplatzer® PFO Occluder, and CardioSEAL® Septal Occlusion Device. One potential drawback with these devices is that they may not be well suited for the long, tunnel-like shape of the PFO 113. As a result, the implanted mechanical devices may become deformed or distorted and in some cases may fail, migrate, or even dislodge. Furthermore, these devices can irritate the cardiac tissue at or near the implantation site, which in turn can potentially cause thromboembolic events, palpitations, and arrhythmias. Other reported complications include weakening, erosion, and tearing of the cardiac tissues around the implanted devices.

Another potential drawback with the implanted mechanical devices described above is that, in order to be completely effective, the tissue around the devices must endothelize once the devices are implanted. The endothelization process can be gradual and can accordingly take several months or more to occur. Accordingly, the foregoing techniques do not immediately solve the problems caused by the PFO 113.

Still another drawback associated with the foregoing techniques is that they can be technically complicated and cumbersome. Accordingly, the techniques may require multiple attempts before the mechanical device is appropriately positioned and implanted. As a result, implanting these devices may require long procedure times during which the patient must be kept under conscious sedation, which can pose further risks to the patient.

BRIEF DESCRIPTION OF THE DRAWINGS

FIGS. 1A-1D illustrate a human heart having a patent foramen ovale (PFO) in accordance with the prior art.

FIGS. 3A-3J illustrate a process for closing a PFO in accordance with an embodiment of the disclosure.

FIGS. 5A-5D are schematic, isometric illustrations of a process for closing a PFO using a trans-primum procedure in accordance with another embodiment of the disclosure.

FIGS. 8A-8L illustrate electrode devices that include conductive filaments in accordance with several embodiments of the disclosure.

FIGS. 10A and 10B illustrate an electrode device including a conductive material that deploys in an "umbrella" fashion.

FIGS. 15A-15B illustrate an electrode device that includes a tubular portion and fingers configured in accordance with an embodiment of the disclosure.

FIGS. 16A-16B illustrate an electrode device having nested tubular portions with inner and outer fingers in accordance with another embodiment of the disclosure.

FIGS. 19A and 19B illustrate an electrode device having knitted fibers forming a tubular portion and a flange in accordance with another embodiment of the disclosure.

FIGS. 20A and 20B illustrate an electrode device having fibers woven to form a tubular portion and a flange in accordance with yet another embodiment of the disclosure.

DETAILED DESCRIPTION

A. Introduction

Aspects of the present disclosure are directed generally to methods and devices for drawing portions of cardiovascular tissue together, sealing the portions to each other, and controlling the performance of these tasks. Much of the discussion below is provided in the context of sealing patent foremen ovales (PFOs). However, in other embodiments, these techniques may be used to treat other types of cardiac tissue and/or tissue defects. The energy to seal the PFO is generally provided by an energy transmitter. For purposes of discussion, much of the following description is provided in the context of energy transmitters that include electrodes configured to seal cardiac tissue by delivering radio frequency (RF) energy. In other embodiments, the energy transmitters can have other arrangements and can deliver other types of energy, for example, microwave energy, laser energy or ultrasound energy.

In general, many of the techniques and associated devices described below include advancing a catheter into the right atrium of the patient's heart, piercing the septum between the right atrium and the left atrium, and placing an electrode or other energy transmitter in the left atrium. The energy transmitter applies energy to the septum to seal the PFO, optionally with the assistance of a balloon or other inflatable member, and is then drawn back through the septum. The catheter can then be withdrawn from the patient's body, leaving no foreign objects behind. A residual hole in the septum remaining after the electrode is withdrawn from the left atrium to the right atrium is expected to close over a short period of time as a result of the body's natural healing response.

Many techniques and devices described in detail in one or more of the following sections may be combined with techniques and/or devices described in the same section and/or other sections. Several details describing devices or processes that are well-known to those of ordinary skill in the relevant art and often associated with such devices and processes are not set forth in the following description for purposes of brevity. Those of ordinary skill in the relevant art will understand that further embodiments may include features not disclosed in the following sections, and/or may eliminate some of the features described below with reference to FIGS. 2-23.

Figure 2:
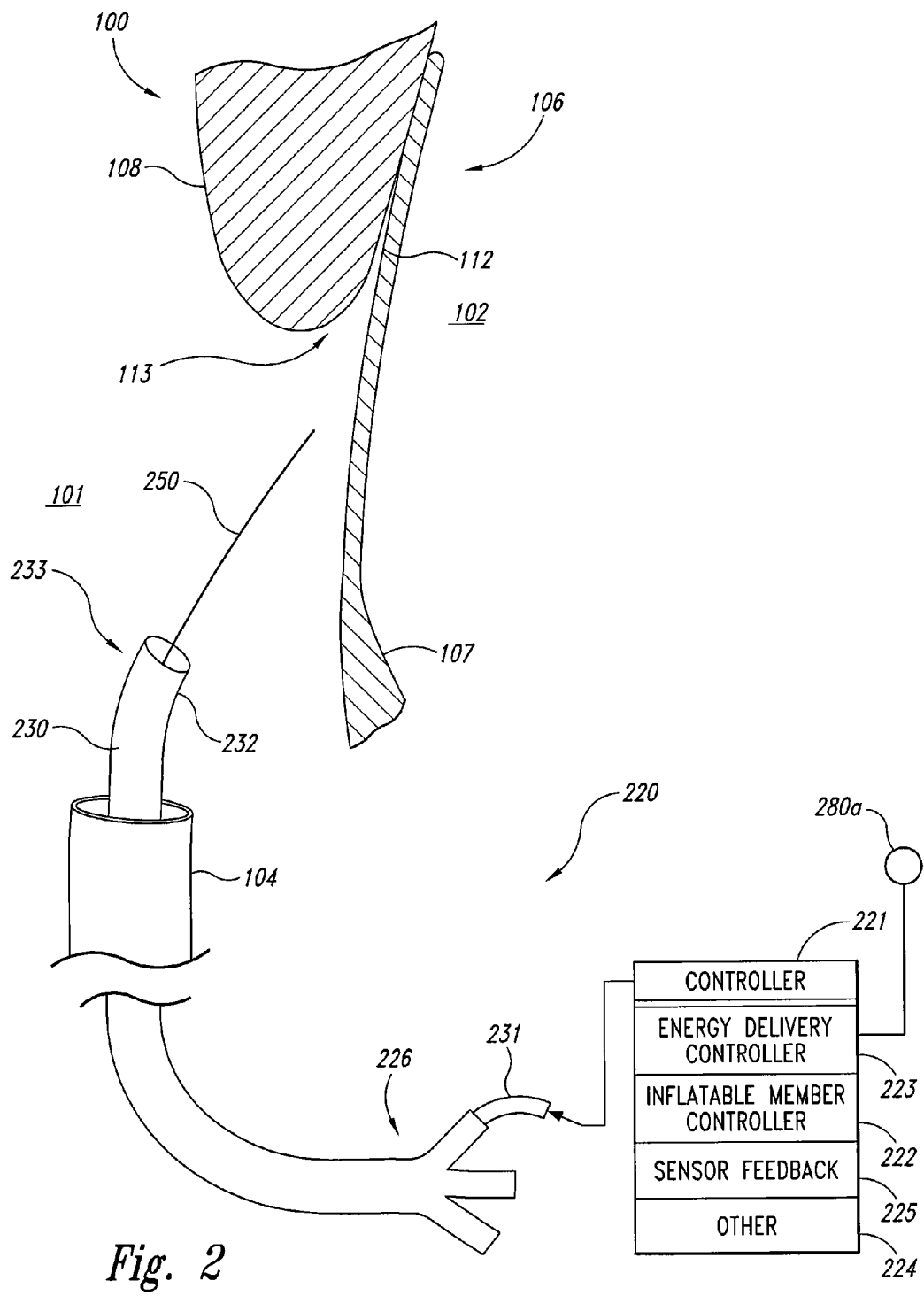
FIG. 2 illustrates a catheter positioned proximate to a PFO for treatment in accordance with several embodiments of the disclosure.

FIG. 2 is a schematic, not-to-scale illustration of the general components of a system 220 used to treat a patient in accordance with several embodiments of the disclosure. The system 220 generally includes one or more patient treatment devices, a term which, as used herein, includes devices that provide direct therapeutic benefits, and/or associated functions, including but not limited to, diagnostic functions, feedback functions, and/or positioning functions. The system 220 can include one or more guidewires 250 that are directed into the patient via an introducer 226, and are then threaded through the patient's vascular system to the heart 100. In the illustrated embodiment, the guidewire 250 enters the right atrium 101 from the inferior vena cava 104, and in other embodiments, the guidewire 250 can enter the right atrium 101 or other heart chamber from other vessels. One or more guidewires may also pass into the left atrium 102. One or more catheters 230 are then threaded along the guidewire 250 via corresponding lumens to treat a PFO 113 (e.g., the PFO tunnel 112) located between the primum 107 and the secundum 108 of the patient's septum 106. The catheter lumen(s) can be flushed with saline or another appropriate biocompatible fluid, either continuously or at selected intervals, to prevent clot formation and/or to lubricate the relative motion between the catheter(s) and devices within the lumens.

The catheter 230 typically includes a distal end 232 within the patient's body, a working portion 233 toward the distal end 232, and a proximal end 231 that extends outside the patient's body. A controller 221 controls the functions carried out by the catheter 230 and the rest of the system 220, and can include an energy delivery controller 223 to control RF or other energy transmitted to the patient, an inflatable member controller 222 to control the operation of one or more inflatable members in the patient, a sensor feedback unit 225 to receive diagnostic information, and other controllers 224 to control other functions, for example, the motion of various guidewires and/or other elements of the system 220, and/or fluid delivery to elements of the system 220. A representative handheld controller configured for such purposes is described in co-pending U.S. application Ser. No. 12/246,349, filed concurrently herewith and incorporated herein by reference. When the energy transmitter or delivery device includes an electrode, it may be operated in a monopolar manner, in which case a return electrode 280a is located remotely from the PFO 113. For example, the return electrode 280a can include a patient pad located at the back of the patient's left shoulder. In other embodiments, the electrode can operate in a bipolar manner, in which case the return electrode is generally located at or close to the PFO 113.

For purposes of organization and ease of understanding, the following discussion is arranged in five sections in addition to the present Section A. Section B describes overall techniques and tissue sealing devices for sealing a patient's PFO. Section C describes self-centering guidewires used to position the tissue sealing devices, and Section D describes systems and techniques for penetrating the septal tissue. Section E describes electrodes configured to seal the PFO, and Section F describes systems and techniques for clamping the septal tissue as it is sealed. Similar disclosures are included in the following U.S. Applications, filed concurrently herewith and incorporated herein by reference: U.S. application Ser. No. 12/246,369; U.S. application Ser. No. 12/246,366; and U.S. application Ser. No. 12/246,361.

B. General Techniques and Systems for Treating a PFO

FIGS. 3A-3I are enlarged cross-sectional views of the heart regions around a PFO, and illustrate representative techniques and associated devices for sealing the PFO in accordance with a particular embodiment. Beginning with FIG. 3A, a practitioner passes a right atrial guidewire 250a into the right atrium 101 of the patient's heart 100 in accordance with a particular embodiment. Optionally, the practitioner can continue to advance the right atrial guidewire 250a into the superior vena cava. The practitioner then passes a left atrial guidewire 250b into the right atrium 101, through the PFO tunnel 112 and into the left atrium 102. Accordingly, the left atrial guidewire 250b is positioned in the tunnel 112 between the primum 107 and the secundum 108. Suitable imaging processes (e.g., transthoracic ultrasound or TTE, intra-cardiac echo or ICE, transesophageal echo or TEE, fluoroscopy, and/or others) known to those of ordinary skill in the relevant art may be used to position the guidewires 250a, 250b and/or other devices used during the procedure.

In another embodiment, the left atrial guidewire 250b is routed as described above, but before the right atrial guidewire 250a is introduced. The right atrial guidewire 250a is instead pre-loaded into a delivery catheter (described later with reference to FIG. 3C), and the delivery catheter, with the right atrial guidewire 250a on board, is threaded along the left atrial guidewire 250b to the right atrium 101 (e.g., at or near the junction between the right atrium 101 and the inferior vena cava). Once the delivery catheter is in the right atrium 101, the right atrial guidewire 250a can be deployed to the location shown in FIG. 3A.

Figure 3B:
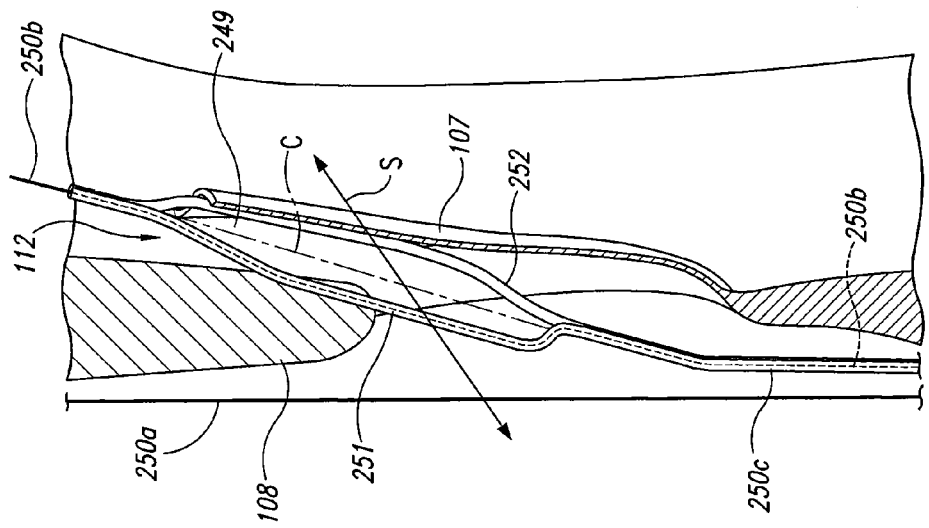
Figure 3A:
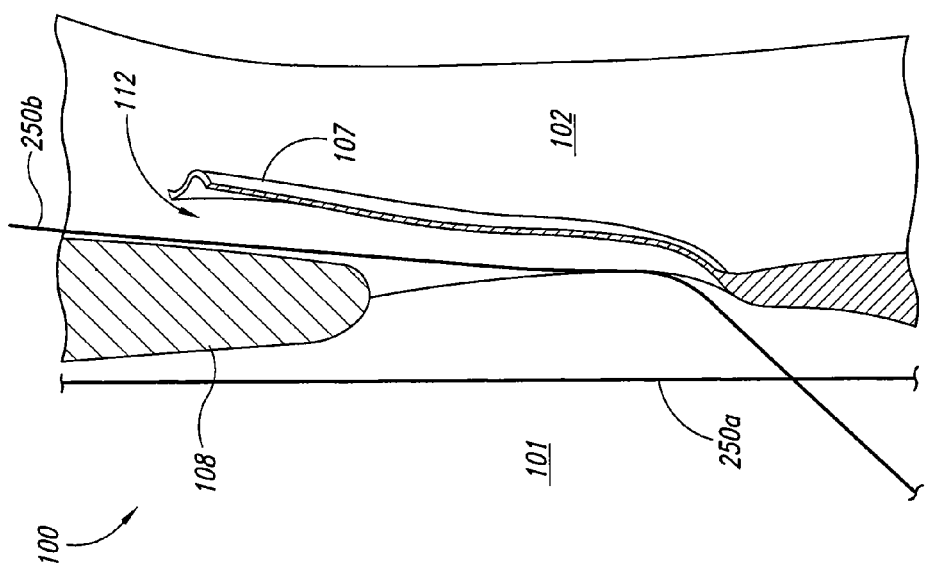

In FIG. 3B, the practitioner has threaded a self-centering guidewire 250c along the left atrial guidewire 250b and into the tunnel 112. Alternatively, the self-centering guidewire 250c can be pre-loaded into the delivery catheter (described later with reference to FIG. 3C) and both can be advanced together along the left atrial guidewire 250b. This latter arrangement, e.g., in combination with pre-loading the right atrial guidewire 250a as described above, can prevent the left atrial guidewire 250b and the right atrial guidewire 250a from becoming twisted. In either embodiment, the self-centering guidewire 250c can include a first branch 251 and a second branch 252 positioned around an enclosed region 249. In a particular aspect of this embodiment, the first branch 251 is hollow so as to receive the left atrial guidewire 250b along which the self-centering guidewire 250c is passed. The first and second branches 251, 252 can be at least somewhat compliant and resilient and can accordingly spread or tighten the primum 107 laterally, as indicated by arrow S, upon being introduced into the tunnel 112. By stretching the primum 107, the self-centering guidewire 250c can draw the primum 107 toward the secundum 108. In addition, the branches 251, 252 can be symmetric relative to a central axis C and can accordingly center the self-centering guidewire 250c within the PFO tunnel 112. Furthermore, the closed shape provided by the first and second branches 251, 252 can provide the guidewire 250c with a degree of lateral rigidity along the axis identified by arrow S. Accordingly, when the guidewire 250c is placed in the tunnel 112, the resilience provided by the primum 107 and/or the secundum 108 can force the guidewire 250c to assume the orientation shown in FIG. 3B, e.g., with the generally flat plane of the enclosed region 249 "sandwiched" between and facing toward the primum 107 on one side and the secundum 108 on the other. The lateral rigidity of the self-centering guidewire 250c when it is deployed can also prevent it from twisting, which in turn can make it easier for the practitioner to accurately seal the tunnel 112.

Turning next to FIG. 3C, the practitioner has threaded a delivery catheter 230a along the right atrial guidewire 250a and the self-centering guidewire 250c, which is in turn threaded along the left atrial guidewire 250b, as discussed above. Or, as discussed above, the right atrial guidewire 250a and the self-centering guidewire 250c can be pre-loaded into the delivery catheter 230a and deployed once the delivery catheter 230a has been threaded along the left atrial guidewire 250b until it is positioned in the right atrium 101. In either embodiment, the delivery catheter 230a can include a right atrial guidewire opening 234a that receives the right atrial guidewire 250a, and a left atrial guidewire opening 234b that receives the self-centering guidewire 250c and the left atrial guidewire 250b over which the self-centering guidewire 250c is passed. In this embodiment, the self-centering guidewire 250c has a generally elliptical cross-sectional shape, and accordingly, the left atrial guidewire opening 234b has a similar shape. With this arrangement, the self-centering guidewire 250c is "keyed" to the delivery catheter 230a. Accordingly, the delivery catheter 230a has a known orientation relative to the self-centering guidewire 250c when the delivery catheter 230a reaches the position shown in FIG. 3C. The upward progress of the delivery catheter 230a can be limited by a "tree crotch effect" provided by the delivery catheter 230a positioned on one side of the septal limbus 117, and the combined left atrial guidewire 250b and self-centering guidewire 250c on the other side of the limbus 117. In addition, radiopaque markers M can be located at the left atrial guidewire opening 234b and the point at which the branches 251, 252 bifurcate. In a particular embodiment, the markers M can therefore be co-located or nearly co-located when the delivery catheter 230a has been properly advanced. Once the delivery catheter 230a has the position shown in FIG. 3C, the right atrial guidewire 250a can optionally be withdrawn, or it can remain in place for additional steps, including for the remainder of the procedure.

As noted above with reference to FIG. 2, the overall system can include a return electrode positioned close to the PFO. FIG. 3C illustrates a return electrode 280b carried by the delivery catheter 230a so as to operate in a bipolar manner with an electrode delivered in accordance with an embodiment of the disclosure. In a particular aspect of this embodiment, the return electrode 280b can include an electrically conductive coating or sleeve positioned at the outside of the delivery catheter 230a, and coupled to an electrical return terminal (e.g., at the controller 221 shown in FIG. 2) via a lead wire (not visible in FIG. 3C). In another embodiment, the return electrode 280b can have other arrangements and/or configurations in which it is positioned close to the primum 107 and/or the secundum 108.

In FIG. 3D, a positioning catheter 230b (which is housed within and movable relative to the delivery catheter 230a) is deployed from the delivery catheter 230a. In this embodiment, the positioning catheter 230b is deployed by applying an axial force to it, causing it to buckle or bend outwardly through a corresponding slot (not visible in FIG. 3D) in the outer surface of the delivery catheter 230a. Accordingly, the positioning catheter 230b can assume the shape shown in FIG. 3D. In one arrangement, the distal end of the positioning catheter 230b is eccentrically connected to a pivot axle 235, which allows the positioning catheter 230b to rotate as indicated by arrow R as it buckles. As the positioning catheter 230b rotates, it can position the exit opening of a lumen 239 to face outwardly from the delivery catheter 230a.

The lumen 239 can also face directly toward the secundum 108, and can be aligned with the central axis C above the limbus 117, as a result of the features of the self-centering guidewire 250c, the delivery catheter 230a and the positioning catheter 230b. In particular, the self-centering guidewire 250c can be centered within the tunnel 112, with the plane defined by the enclosed region 249 facing directly toward the secundum 108. Because the self-centering guidewire 250c has a generally flat shape (and can optionally stretch the primum 107), the primum 107 and the secundum 108 can tend to keep the self-centering guidewire 250c from rotating or twisting about its lengthwise axis relative to the tunnel 112. In addition, the branches 251, 252 of the self-centering guidewire 250 can be secured to each other in a manner that resists twisting. Because the self-centering guidewire 250c is keyed with the delivery catheter 230a, as discussed above with reference to FIG. 3C, the delivery catheter 230a is prevented or at least restricted from rotating about its lengthwise axis relative to the tunnel 112. Accordingly, when the positioning catheter 230b is deployed, the lumen 239 can face directly toward the secundum 108, e.g., at an orientation of from about 80° to about 135°, and in a particular embodiment, about 105°. It is expected that in at least some embodiments, an orientation of about 105° results in a subsequent tissue penetration operation that effectively penetrates the secundum 108 and the primum 107 with a reduced likelihood for penetrating other tissue in the left atrium. In addition, this orientation can increase the likelihood of penetrating the primum 107, e.g., when the tunnel 112 is relatively short. The lumen 239 can also be located at the lateral center or approximate center of the tunnel 112 (e.g., measured laterally along a lateral axis L that is generally transverse to the central axis C). The "tree-crotch effect" described above can act to locate the lumen 239 above the limbus 117, but not so high that the lumen 239 is above the primum 107.

In a particular embodiment, a limbus stop 236 is connected to the positioning catheter 230b. As the positioning catheter 230b rotates, the limbus stop 236 rotates outwardly to the position shown in FIG. 3D. When the practitioner applies an axial (e.g., upward) force to the delivery catheter 230a, the limbus stop 236 can nudge up against the limbus 117. In other embodiments, the limbus stop 236 can be eliminated. In still further embodiments, the delivery catheter 230b can include a limbus marker 236a, in addition to or in lieu of the limbus stop 236. The limbus marker 236a can be a pin or other element made from gold, platinum or another radiopaque material. The limbus marker 236a can help guide the operator to correctly position the delivery catheter 230a relative to the limbus 117 before penetrating the secundum 108. The limbus 117 itself may be illuminated with a contrast agent. In many cases, the delivery catheter 230a and other components illustrated in FIG. 3D may be formed from plastics or other materials that do not readily appear during fluoroscopy processes. Accordingly, the limbus marker 236a can provide a readily visible locater on the delivery catheter 230a to aid the practitioner during a tissue sealing procedure. The limbus marker 236a can be positioned at a known location along the length of the delivery catheter 230a, for example 4 mm below the axis along which a penetrating guidewire is deployed.

Further details of the penetrating guidewire are described below with reference to FIG. 3E.

As shown in FIG. 3E, a penetrating guidewire 250d or other penetrating device or member can be deployed from the positioning catheter 230b. The penetrating guidewire 250d can include a penetrating tip 253 that penetrates through the secundum 108 and the primum 107, so as to cross the entire septum 106 into the left atrium 102. In a particular embodiment, the penetrating tip 253 can include an RF electrode that is advanced through the septum 106 in a stepwise fashion described in further detail below with reference to FIGS. 7A-7F. The electrode can have a generally spherical or ball-type shape, with a diameter of up to about 1.0 mm. In other embodiments, the penetrating tip 253 can have other shapes or configurations, and/or can be advanced using other techniques, and/or can employ other non-RF methods for penetrating the septum 106. Such configurations include, but are not limited to a penetrating tip 253 having a sharp distal end that pierces the septum 106. For example, the penetrating tip can include one or more razor-like elements or blades that score the septum 106. The blades can deploy laterally outwardly, and/or can be deployed from an inflatable balloon. In other embodiments, the tip 253 can include rotoblades, laser energy emitters, and/or ultrasound energy emitters.

In FIG. 3F, the practitioner advances an electrode catheter 230c along the penetrating guidewire 250d from the right atrium 101 into the left atrium 102. The electrode catheter 230c can include a dilator 237 that temporarily stretches the hole initially created by the penetrating guidewire 250d to allow additional components to pass into the left atrium 102. These components can include an inflatable member 270 (shown collapsed) and an electrode device 280. In a particular embodiment, the penetrating guidewire 250d can form a hole having a diameter of about one millimeter, and the dilator 237 can have a diameter of about two millimeters to temporarily stretch the hole to a diameter of about two millimeters. When the electrode catheter 230c and the penetrating guidewire 250d are later withdrawn, the hole can relax back to a diameter of about one millimeter. In other embodiments, these dimensions can have other values. In any of these embodiments, the dilator 237 and/or the penetrating tip 253 can include radiopaque markings for enhanced visibility during fluoroscopic visualization.

Figure 3G:
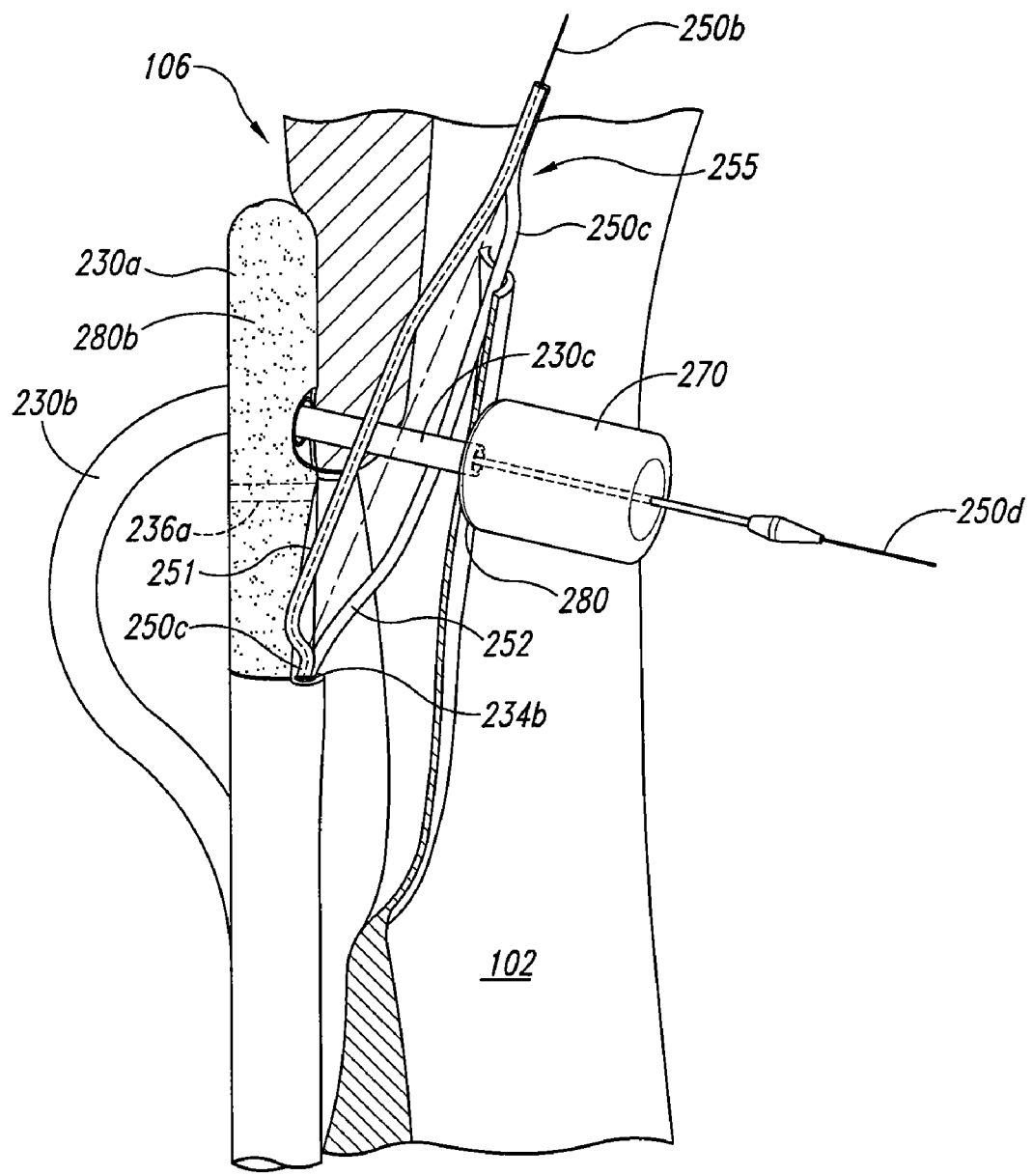

In FIG. 3G, the practitioner has inflated the inflatable member 270 (e.g., with saline or another suitable inflation medium) in the left atrium 102, and has also deployed the electrode device 280. In a particular embodiment, the electrode device 280 includes a conductive coating applied to a proximally facing surface of the inflatable member 270. The inflatable member 270 can be formed from a non-stretch material so that it maintains a predefined shape (e.g., the cylindrical shape shown in FIG. 3G) when inflated. This arrangement can also prevent or restrict the conductive coating from delaminating, flaking, and/or otherwise detaching from the inflatable member 270. Other suitable electrode shapes and configurations are described later with reference to FIGS. 8A-20B and in at least some of these embodiments, the inflatable member 270 is eliminated.

Prior to engaging the electrode device 280 with the septum 106, the practitioner can withdraw the self-centering guidewire 250c and the left atrial guidewire 250b by separating or opening the first and second branches 251, 252 at a separation location 255, allowing them to pass downwardly around opposite sides of the electrode catheter 230c and into the left atrial guidewire opening 234b. Further details of embodiments for performing this task are described later with reference to FIGS. 6A-6K.

Figure 3I:
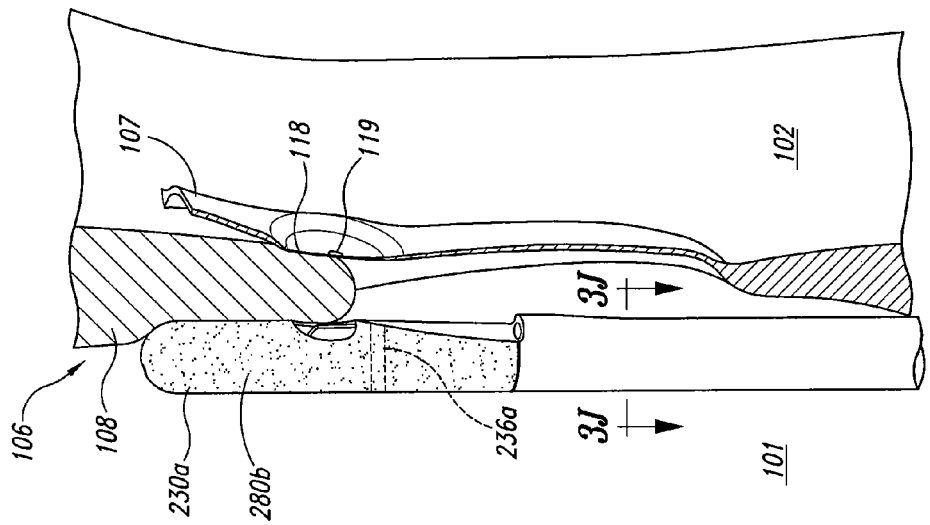
Figure 3H:
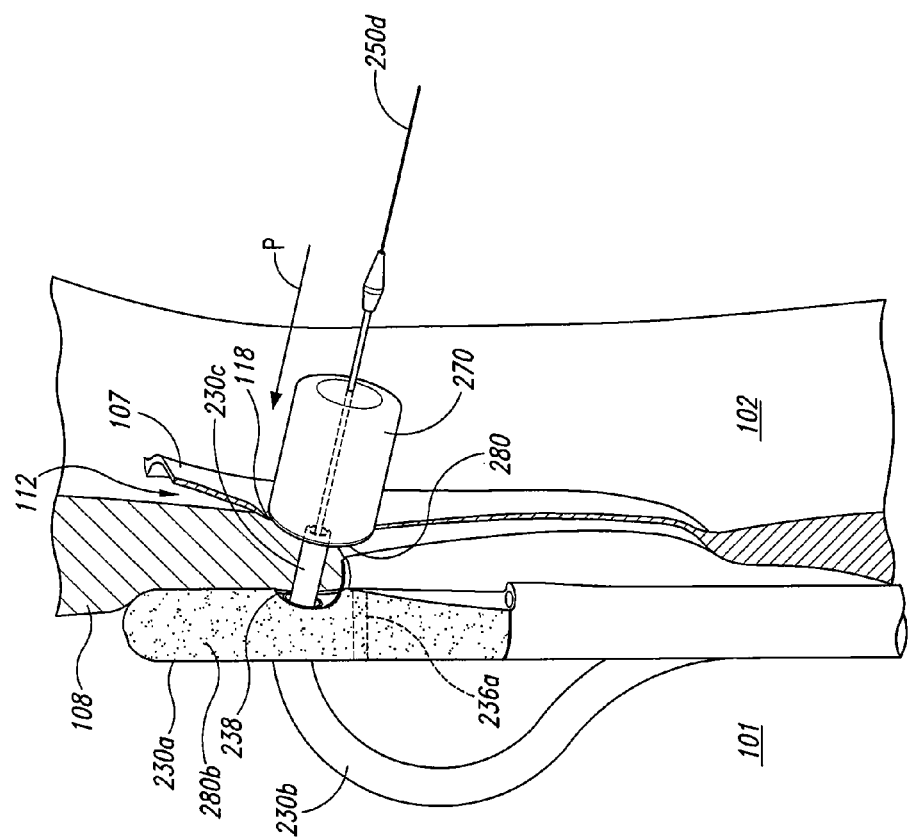

In FIG. 3H, the self-centering guidewire 250c (FIG. 3G) and the left atrial guidewire 250b (FIG. 3G) have been removed, and the practitioner has applied an axial force to the electrode catheter 230c in a generally proximal direction P. The axial force draws the inflatable member 270 and the electrode device 280 snugly up against the primum 107. This force can also clamp the primum 107 against the secundum 108, and can clamp both the primum 107 and the secundum 108 between the electrode device 280 and a backstop surface 238. In an embodiment shown in FIG. 3H, the backstop surface 238 includes the outwardly facing, conductive external surface of the delivery catheter 230a, e.g., the return electrode 280b. Accordingly, the electrode device 280 can operate in a bipolar manner via the return electrode 280b. In other embodiments, the backstop surface 238 can have other locations and/or arrangements. For example, the backstop surface 238 can be separate from the delivery catheter 230a, and/or can be electrically non-conductive, so that the electrode device 280 operates in a monopolar manner.

With the electrode device 280 in the position shown in FIG. 3H, the practitioner can apply electrical energy (e.g., a varying electrical current) to the electrode device 280. In representative embodiments, electrical energy is applied to an electrode device 280 having a diameter in the range of about 3 mm to about 30 mm, at a frequency in the range of about 100 KHz to about 5 MHz for a period of up to 10 minutes (e.g., in a particular embodiment, from about 30-120 seconds). The energy can be provided at a rate in the range of from about 10 Watts to about 500 Watts, and in a particular embodiment, in the range of from about 40 Watts to about 50 Watts. The foregoing ranges are suitable for the electrode device 280 shown in FIG. 3H, and other electrodes as well, including the electrode device 580f described later with reference to FIG. 8J. Different sizes and shapes of the PFO (or other tissue defect) will typically determine the particular electrode device size and/or energy delivery parameters. For example, the electrode device 280 can have a diameter of from about 7 mm to about 20 mm, and in a particular embodiment, about 9 mm. In a particular embodiment, the electrical energy can be applied to a 9 mm diameter electrode device at a frequency of about 450 KHz, for about 5 seconds, at a rate of from about 300 Watts to about 400 Watts. The electrical energy can be applied with a sinusoidal waveform, square waveform, or another periodic waveform shape, generally with a crest factor of from about one to about fifteen. RF energy provided to the electrode device 280 is received by the adjacent tissue so as to heat both the primum 107 and the secundum 108. The heat can at least partially fuse, glue, cement, or otherwise seal, join or connect the primum 107 and the secundum 108 together, forming a seal 118 that partially or completely closes the PFO tunnel 112 between the left atrium 102 and the right atrium 101.

After the tissue fusing and/or sealing process has been completed, the inflatable member 270 can be collapsed and the electrode catheter 230c, the positioning catheter 230b and the penetrating guidewire 250d can be withdrawn into the delivery catheter 230a, as is shown in FIG. 3I. A residual opening 119 may remain in the seal 118 as a result of withdrawing the electrode catheter 230c and penetrating guidewire 250d (FIG. 3H) back through the septum 106 from the left atrium 102 to the right atrium 101. The residual opening 119 is typically very small (e.g., on the order of one millimeter) and is expected to close quickly as a result of the body's normal healing process. The practitioner then withdraws the delivery catheter 230a from the patient's body. In other cases in which the seal 118 may initially be incomplete for other reasons, it is also expected that the seal will be sufficient to allow the body's normal healing processes to complete the closure, generally in a short period of time.

Figure 3J:
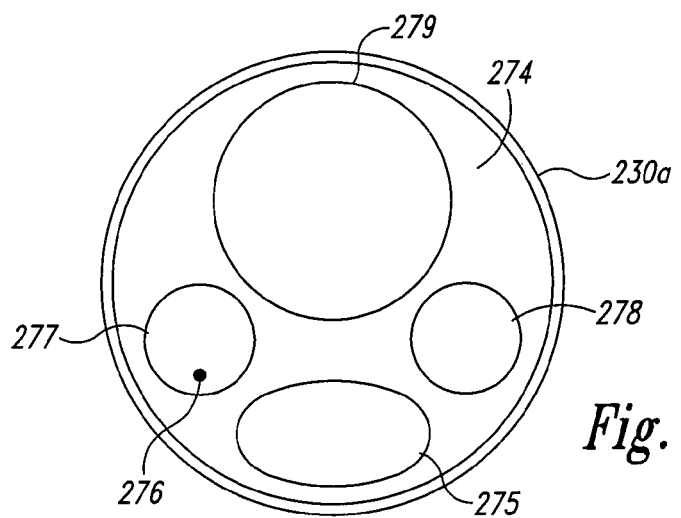
Figure 4:
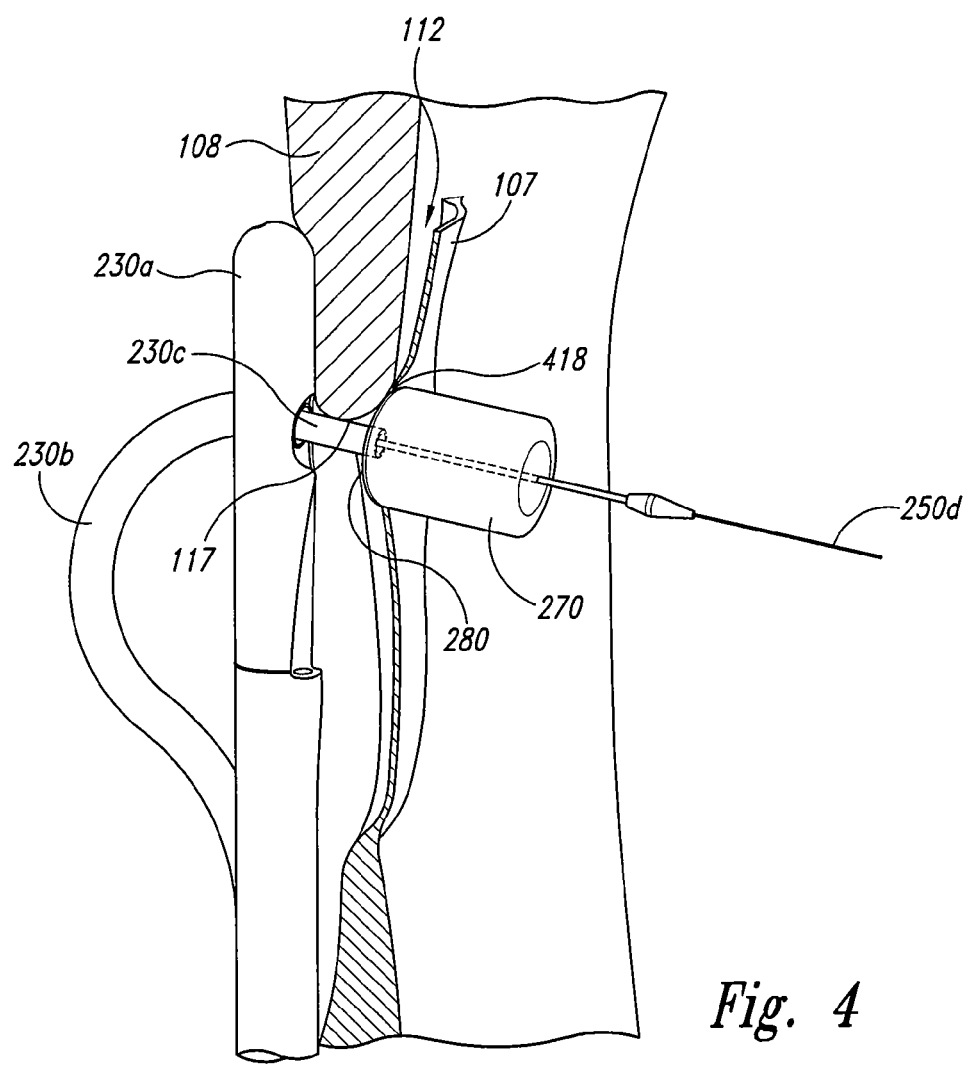
FIG. 4 is a partially schematic, isometric illustration of a process for closing a PFO via a trans-primum procedure in accordance with an embodiment of the disclosure.

FIG. 3J is a partially schematic, cross-sectional illustration of the delivery catheter 230a taken substantially along line 3J-3J of FIG. 3I. As shown in FIG. 3J, the delivery catheter 230a can include multiple lumens, including an electrode catheter lumen 279 that carries the positioning catheter 230b (FIG. 3F) and the electrode catheter 230c (FIG. 3F) housed within it. The delivery catheter 230a can also include a right atrial guidewire lumen 278 that houses the right atrial guidewire 250a (FIG. 3C), and a self-centering guidewire lumen 275 that houses the self-centering guidewire 250c (FIG. 3C). A return electrode lumen 277 houses a return electrode lead 276 that is in turn coupled to the return electrode 280b (FIG. 3C). Contrast agent can be delivered to the PFO region via any of the foregoing lumens (e.g., the return electrode lumen 277), and/or via an interstitial region 274 between neighboring lumens.

In other embodiments, techniques similar at least in part to those described above with reference FIGS. 3A-3I may be used to form tissue seals in different manners. For example, referring now to FIG. 4, the delivery catheter 230a can be located so that the positioning catheter 230b is below the limbus 117 and facing the primum 107, rather than above the limbus 117 and facing the secundum 108, as described above with reference to FIGS. 3A-3I. Accordingly, when the penetrating guidewire 250d and the electrode catheter 230c are deployed, they pass through the primum 107 but not the secundum 108. The resulting tissue seal 418 will typically be smaller than the seal 118 described above with reference to FIG. 3I because a greater portion of the electrode device 280 is located below the limbus 117 and does not face directly toward the secundum 108. However, this arrangement may be suitable where it is expected that the smaller seal 418 will still have the desired effect on the PFO tunnel 112 (e.g., tunnel sealing), and/or where it is undesirable to penetrate the secundum 108.

Figure 5B:
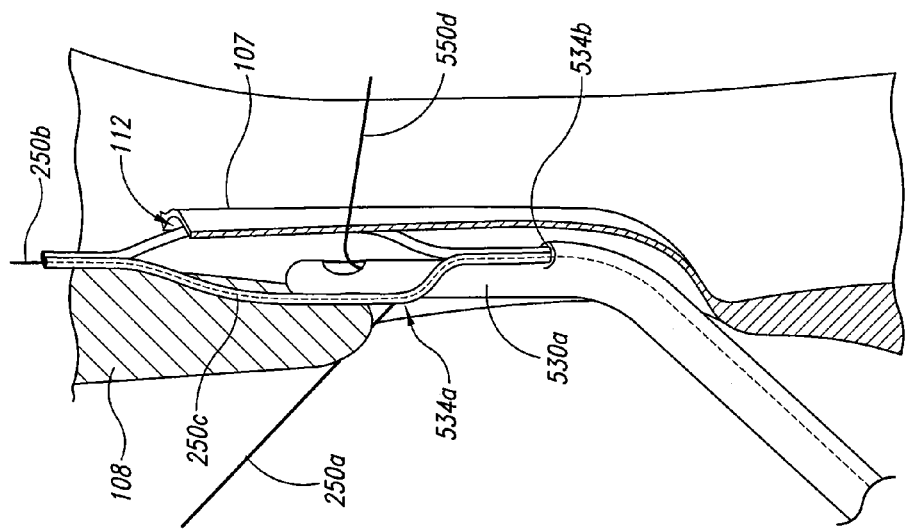
Figure 5A:
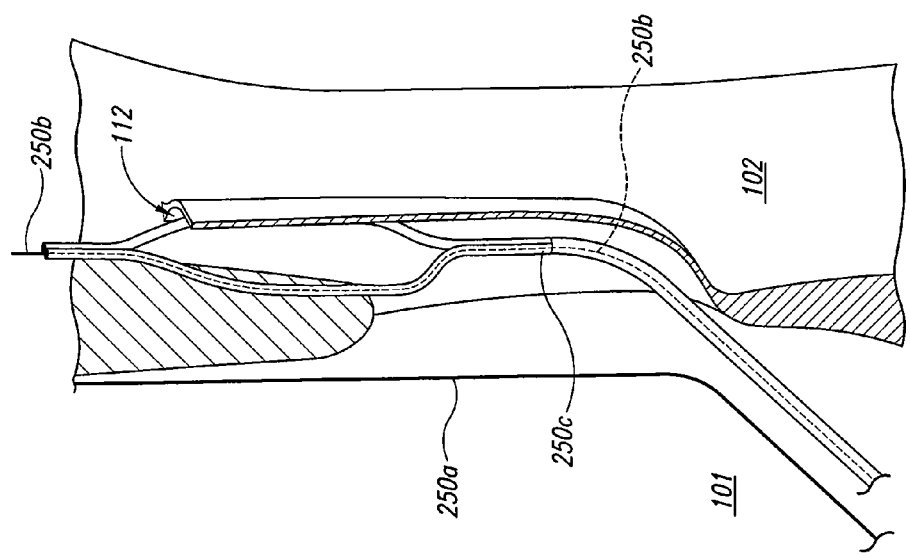

FIGS. 5A-5D illustrate another arrangement for sealing the PFO tunnel 112 without penetrating the secundum 108. As shown in FIG. 5A, the right atrial guidewire 250a is positioned in the right atrium 101, and the left atrial guidewire 250b and the self-centering guidewire 250c are positioned in the tunnel 112 and the left atrium 102. In FIG. 5B, a delivery catheter 530a is threaded along the right atrial guidewire 250a and the self-centering guidewire 250c. A right atrial guidewire opening 534a and a left atrial guidewire opening 534b are positioned so that as the delivery catheter 530a is passed along the guidewires 250a-250c, it enters the PFO tunnel 112. A penetrating guidewire 550d, when deployed, accordingly penetrates only the primum 107 and not the secundum 108.

After the penetrating guidewire 550d has passed through the primum 107, the delivery catheter 530a is removed, as shown in FIG. 5C. The right atrial guidewire 550a is then also removed. In FIG. 5D, the practitioner threads a positioning catheter 530b along the penetrating guidewire 550d, and deploys an electrode catheter 530c from the positioning catheter 530b to pass through the primum 107. The electrode catheter 530c can include an electrode device 280 and an inflatable member 270 generally similar to those described above with reference to FIG. 3G. When drawn up against the primum 107, the electrode device 280 can clamp the primum 107 and the secundum 108 against a backstop surface 538 of the positioning catheter 530b. The resulting seal 518 has a shape and location generally similar to the seal 418 described above with reference to FIG. 4.

C. Self-Centering Guidewires and Associated Systems and Methods

In many of the embodiments described above, a self-centering intravenous guidewire can be used to locate the sides, edges and/or lateral boundaries of the PFO tunnel 112, thus allowing the practitioner to more precisely locate the tissue seal at the center of the tunnel 112, e.g., along an axis transverse or generally transverse to the flow axis of the tunnel 112. FIGS. 6A-6K illustrate representative embodiments of guidewires, generally referred to as self-centering guidewires, suitable for performing this function. Beginning with FIG. 6A, a self-centering guidewire 650a (generally similar to the self-centering guidewire 250c described above) includes a first branch 651a and a second branch 652a that are fixedly secured relative to each other at a first location 654a. When the self-centering guidewire 250c is positioned in a catheter, the first and second branches 651a, 652a are squeezed toward each other. The first and second branches 651a, 652a can be formed from a flexible, resilient material, e.g., Nitinol or another material that tends to assume the shape shown in FIG. 6A when the self-centering guidewire 650a is deployed. When in the deployed position, the first and second branches 651a, 652a can be located in the same generally flat plane. The first branch 651a can have a hollow or tubular construction, which allows it to be threaded along the left atrial guidewire 250b. The practitioner advances the self-centering guidewire 650a along the left atrial guidewire 250b by applying an axial force to a distal portion of the self-centering guidewire 650a while the left atrial guidewire 250b is held in place. The delivery catheter 230a (FIG. 3C) is then passed along the self-centering guidewire 650a.

Figure 6A:
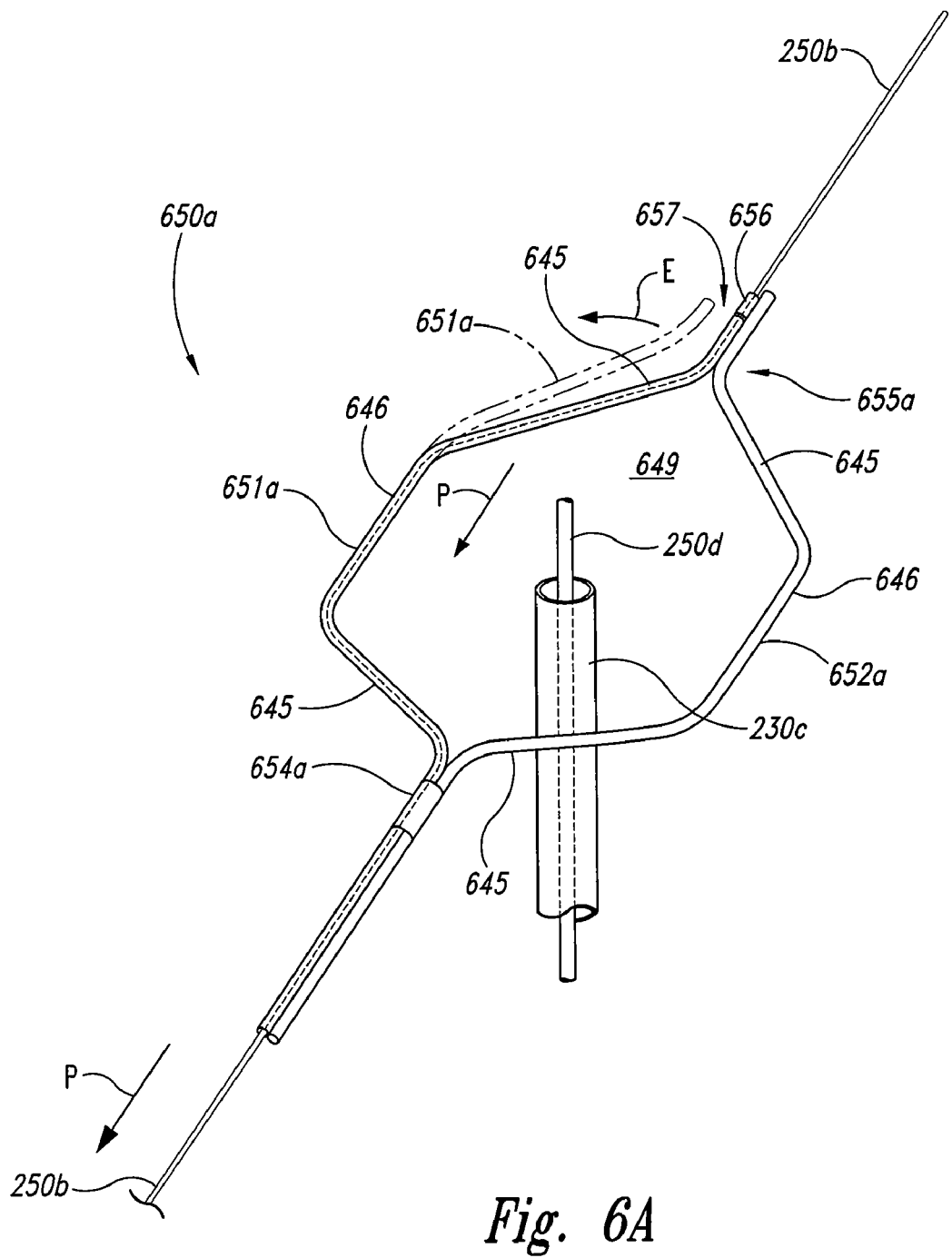
FIGS. 6A-6M illustrate guidewires configured to center in a PFO tunnel in accordance with embodiments of the disclosure.

The self-centering guidewire 650a can also include a connector tube 656 at a second location 655a. The connector tube 656 can be fixedly attached to the second branch 652a, but not to the first branch 651a. The left atrial guidewire 250b can pass through both the tubular first branch 651a and the connector tube 656, so that the first branch 651a and the second branch 652a form a generally closed shape around an enclosed region 649. The left atrial guidewire 250b can accordingly prevent the branches 651a, 652a from separating at the second location 655a. The practitioner then directs the penetrating guidewire 250d through the septum (as described above with reference to FIG. 3E) and through the enclosed region 649 between the first and second branches 651a, 652a. Next, the practitioner can pass the electrode catheter 230c (a portion of which is shown in FIG. 6A) over the penetrating guidewire 250d, as was discussed above with reference to FIG. 3F, and through the enclosed region 649.

To remove the self-centering guidewire 650a without disturbing the electrode catheter 230c, the practitioner can withdraw the left atrial guidewire 250b from the connector tube 656 by moving the left atrial guidewire 250b in a proximal direction P. Without the left atrial guidewire 250b securing the first branch 651a to the connector tube 656, the first branch 651a can at least disengage from the connector tube 656, and in a particular embodiment, can spring away from the second branch 652a as indicated by arrow E, and as shown in dashed lines in FIG. 6A. Accordingly, the first branch 651a and the second branch 652a can form an open shape having a gap 657. With this configuration, the self-centering guidewire 650a can be withdrawn in a proximal direction P so that the first branch 651a passes along one side of the electrode catheter 230c and the second branch 652a, separated from the first branch by the gap 657, passes along the opposite side of the electrode catheter 230c. The practitioner can then withdraw the self-centering guidewire 650a and the left atrial guidewire 250b into the delivery catheter 230a (FIG. 3H) while the electrode catheter 230a remains in position. In another embodiment, the first branch 651a can disengage from the connector tube 656 without initially moving to form the gap 657. In this case, the first branch 651a can contact the electrode catheter 230c as the self-centering guidewire 650 is drawn proximally, causing the first branch 651a to deflect away from and around the electrode catheter 230c.

In a particular embodiment, the first and second branches 651a, 652a can enclose a generally hexagonally-shaped enclosed region 649 having rounded or arcuate corners. Accordingly, the first and second branches 651a, 652a can move smoothly into and out of the PFO tunnel 112 (FIG. 3H). The rounded or arcuate portions of the first branch 651a can also accommodate the left atrial guidewire 250b positioned within it without causing the left atrial guidewire 250b to kink or bind. Each of the first and second branches 651a, 651b can have generally parallel side portions 646 toward the center of the self-centering guidewire 650a, and converging end portions 645 toward the first and second locations 654a, 655a. This arrangement can be particularly suitable when the opposing edges of the PFO tunnel 112 are generally parallel. In other embodiments, other shapes (e.g., elliptical shapes and/or other arcuate shapes) can also be suitable for such tunnel topologies. In still further embodiments, the enclosed region 649 can have other shapes, e.g., shapes with non-parallel side portions 646, depending on the particular patient's tunnel characteristics. In any of these embodiments, the first and second locations 654a, 654b (and/or other locations of the self-centering guidewire 650a) can include radiopaque markings for enhanced visibility during fluoroscopic visualization.

Figure 6B:
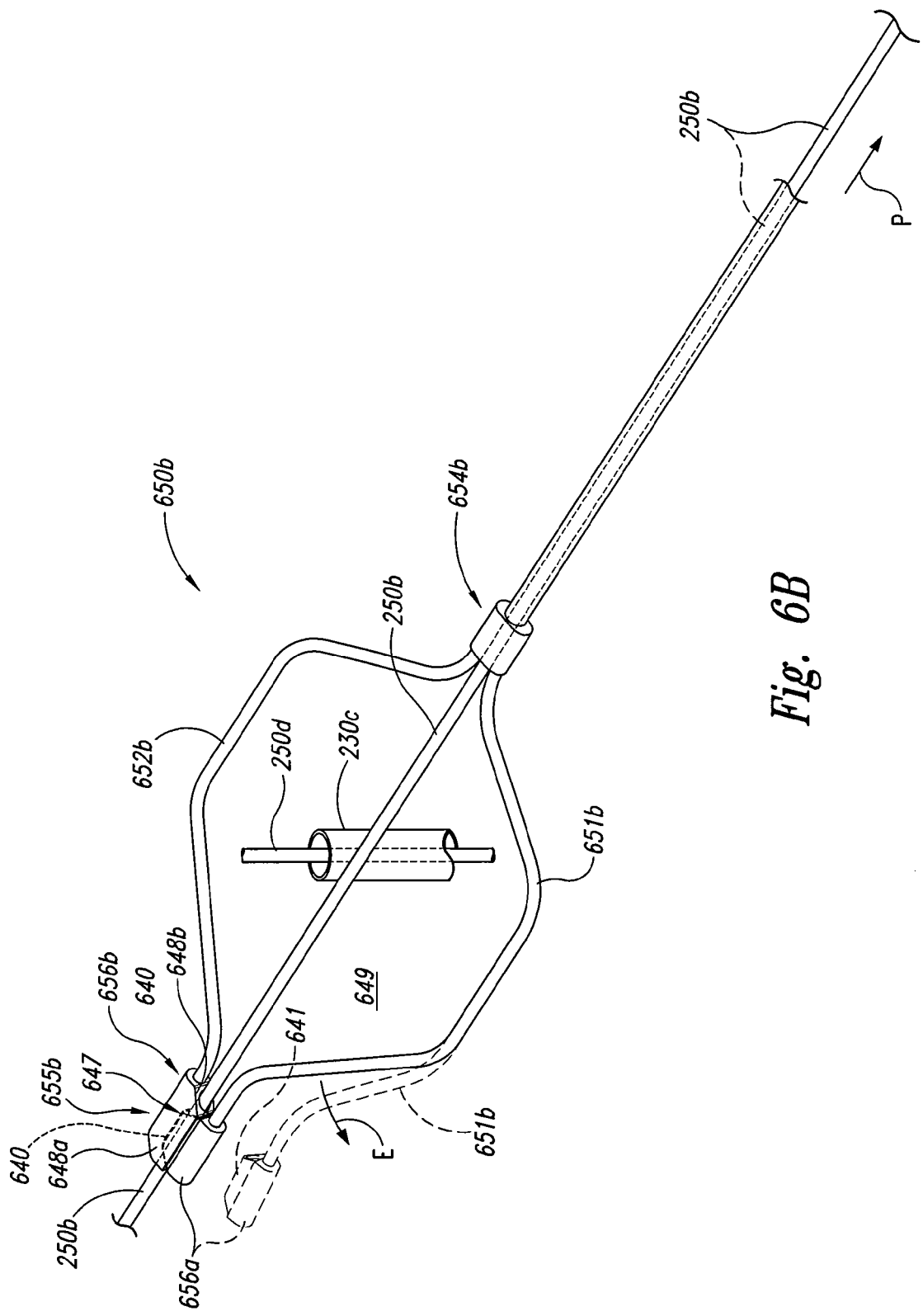

FIG. 6B illustrates a self-centering guidewire 650b having a central enclosed region 649 formed by a first branch 651b and a second branch 652b, with the left atrial guidewire 250b passing through, rather than around, the enclosed region 649, in accordance with another embodiment. In a particular aspect of this embodiment, the first and second branches 651b, 652b are fixedly secured relative to each other at a first location 654b, and are releasably secured relative to each other by the left atrial guidewire 250b at a second location 655b. At the second location 655b, the first branch 651b includes a first connector tube 656a, and the second branch 652b includes a second connector tube 656b having two portions 648a, 648b separated by a space 647 (e.g., in the form of a slot or other receptacle 640). The first connector tube 656a is removably received in the space 647, e.g., in a tab-and-slot arrangement. In particular, the first connector tube 656a can include a tab 641 having surfaces generally parallel to the plane of the enclosed region 649, and the second connector tube 656b can have receptacle or slot surfaces that are also generally parallel to the plane of the enclosed region 649. Accordingly, the first and second branches 651b, 652b can interlock at the second location 655b when the tab 641 is received in (e.g., snugly engaged with) the receptacle 640. The tab-and-slot arrangement can restrict or eliminate relative twisting between the two branches 651b, 652b, thus maintaining the generally flat, planar shape of the enclosed region 649. The left atrial guidewire 250b passes through both the first and second connector tubes 656a, 656b when the self-centering guidewire 650b forms the enclosed region 649. To remove the self-centering guidewire 650b without disturbing the electrode catheter 230c, the practitioner can withdraw the left atrial guidewire 250b proximally (as indicated by arrow P) from the first connector tube 656a, allowing the first branch 651b to release and, in at least one embodiment, spring outwardly, as indicated by arrow E. The first and second branches 651b, 652b can then be passed around the electrode catheter 230a and out of the patient's body without disturbing the electrode catheter 230c.

Figure 6C:
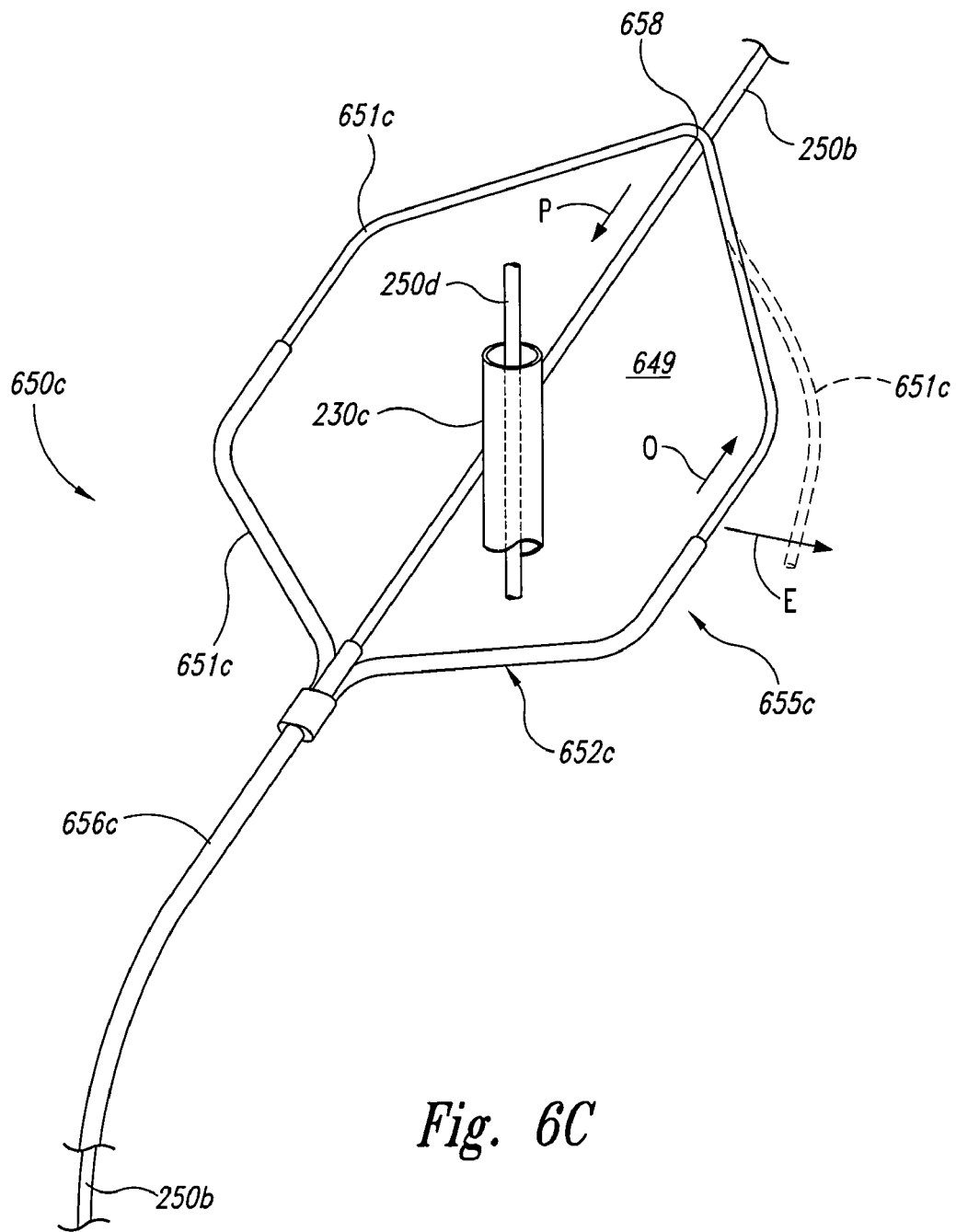

FIG. 6C illustrates a self-centering guidewire 650c configured in accordance with another embodiment in which the electrode catheter 230c is used to separate a first branch 651c from a second branch 652c at a second location 655c. The self-centering guidewire 650c can include a tube 656c that is threaded along the left atrial guidewire 250b as the self-centering guidewire 650c is advanced into the heart. Prior to separating the first and second branches 651c, 652c, the first branch 651c extends around most of the enclosed region 649 and is received in an opening at the end of the second branch 652c, at the second location 655c. When the self-centering guidewire 650c is moved in a proximal direction P toward the electrode catheter 230c, a contact portion 658 of the first branch 651c contacts the electrode catheter 230c. As the practitioner applies an additional axial force to the self-centering guidewire 650c, the electrode catheter 230c forces the end of the first branch 651c out of the opening at the end of the second branch 652c, as indicated by arrow O, causing the first branch 651c to disengage, and in at least one embodiment, spring outwardly as indicated by arrow E. With the self-centering guidewire 650c in this configuration, it can be removed from around the electrode catheter 230c. In other embodiments, mechanisms other than the opening at the end of the second branch 652c can be used to releasably connect the first and second branches 651c, 652c at the second location 655c. For example, magnets carried by each of the first and second branches, 651c, 652c can be used to perform this function.

Figure 6D:
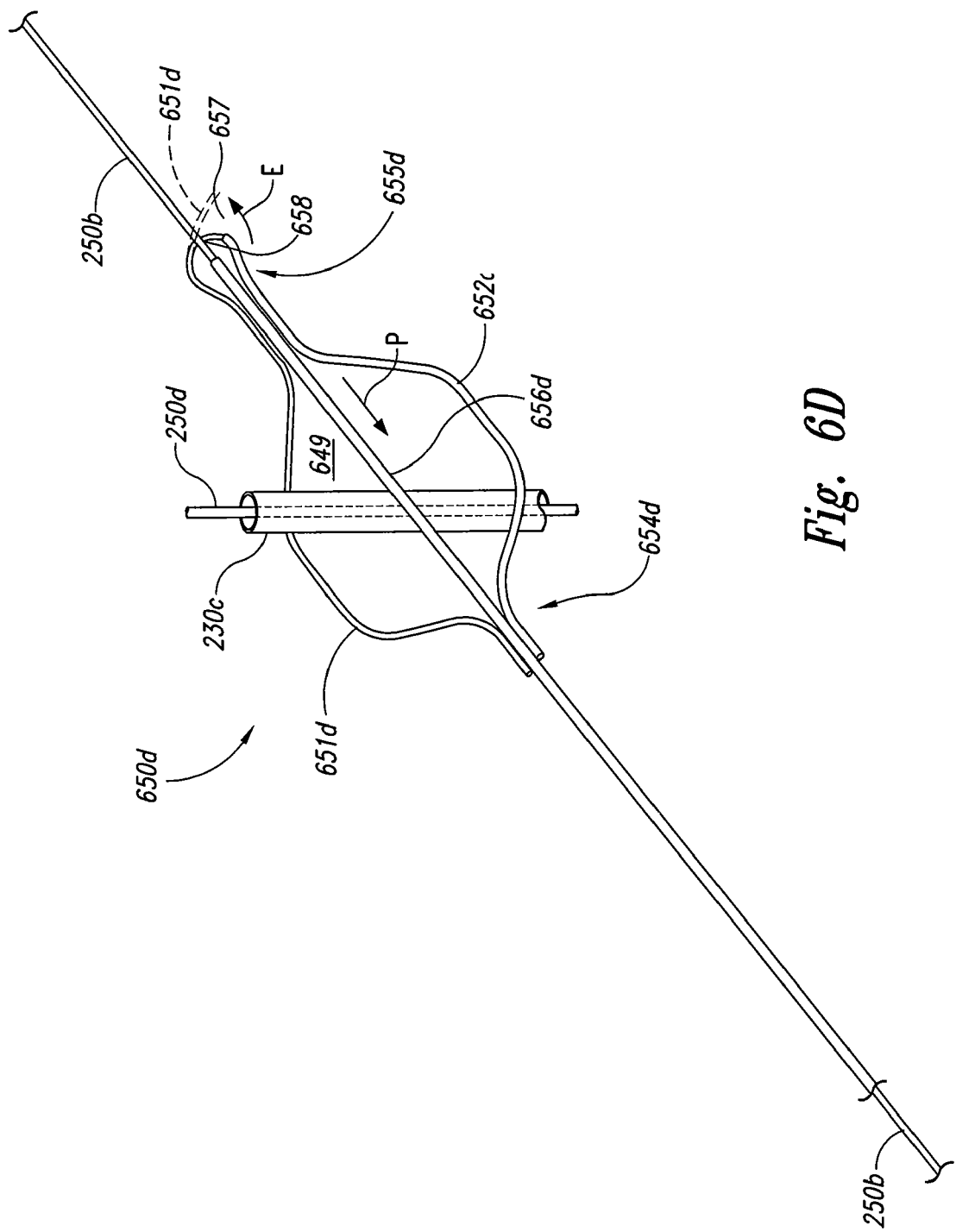

FIG. 6D illustrates a self-centering guidewire 650d that is similar in some respects to the self-centering guidewire 650c described above with reference to FIG. 6C. In particular, an embodiment of the self-centering guidewire 650d includes a first branch 651d attached to a second branch 652d at a first location 654d. The first branch 651d includes an end that is removably received in a tubular portion of the second branch 652d at a second location 655d. A central tube 656d is threaded along the left atrial guidewire 250c and extends generally across the enclosed region 649, but is not attached to the first and second branches 651d, 652d, except at the first location 654d. The increased axial length of the tube 656d can further guide and align the self-centering guidewire 650d relative to the left atrial guidewire 250c. When the self-centering guidewire 650d is to be removed, the practitioner can move it in a proximal direction P until a contact portion 658 contacts the electrode catheter 230c. When the practitioner moves the self-centering guidewire 650d by an additional amount in the proximal direction P, the first branch 651d pulls out of the second branch 652d, separating and/or springing open as indicated by arrow E and opening a gap 657 through which the electrode catheter 230c passes as the self-centering guidewire 650d is removed.

Figure 6E:
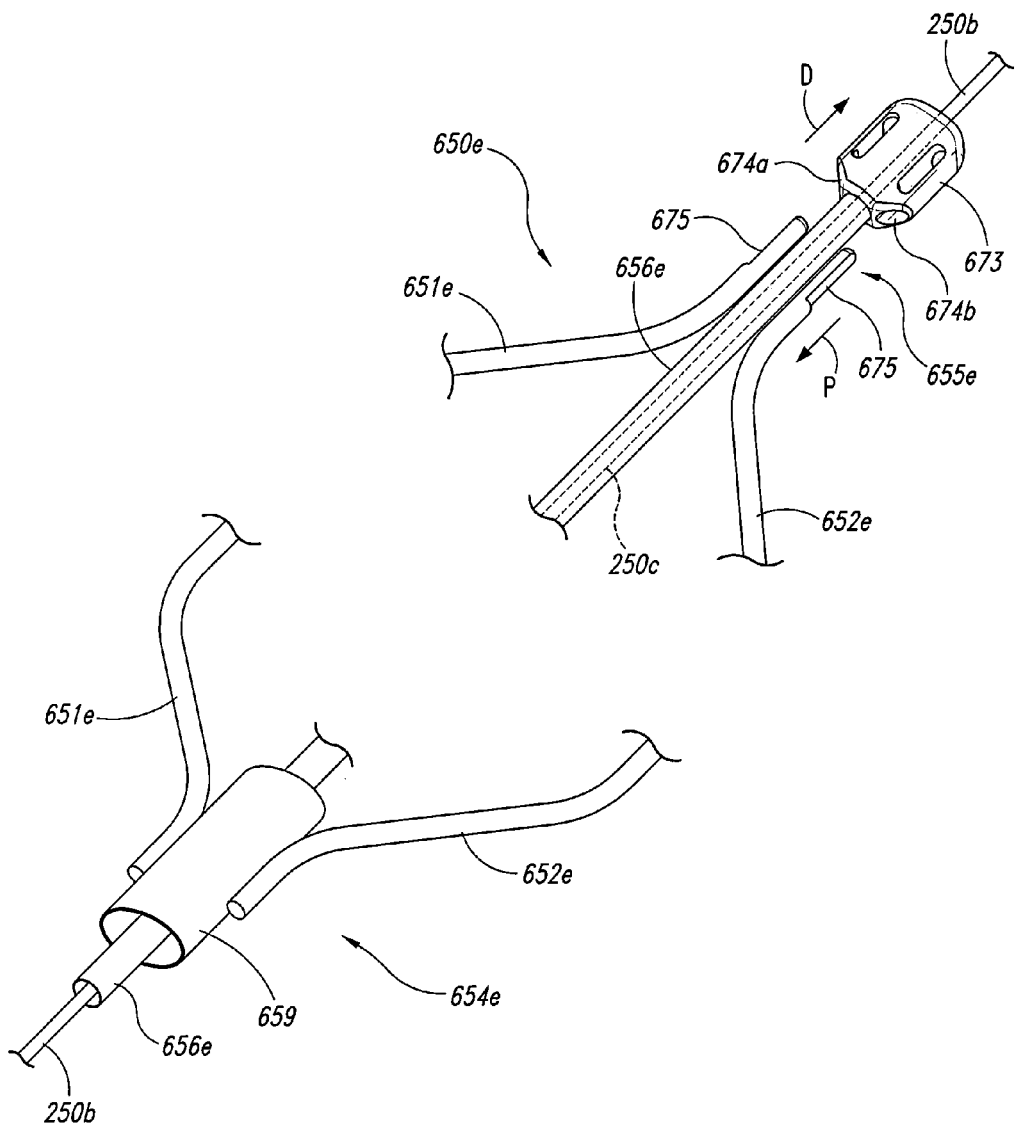

FIG. 6E is a partially broken illustration of a self-centering guidewire 650e configured in accordance with still another embodiment. In one aspect of this embodiment, the guidewire 650e includes a first branch 651e and a second branch 652e that each have a fixed position relative to the other at a first location 654e and are removably secured relative to each other at a second location 655e. At the first location 654e, the first and second branches 654e, 655e can be connected to a ferrule 659 that slideably receives a connector tube 656e which is in turn threaded along the left atrial guidewire 250c. The connector tube 656e can include a connector 673 toward its distal end. The connector 673 can include a first aperture 674a that receives the first branch 651e, and a second aperture 674b that receives the second branch 652e. Flat surfaces 675 on the ends of the branches 651e, 652e snugly mate with corresponding surfaces within the connector 673 to resist the tendency for the branches 651e, 652e to twist out of the plane shown in FIG. 6E. When the self-centering guidewire 650e is deployed into the patient's PFO, the connector tube 656e and the attached connector 673 have a position that is proximal (as indicated by arrow P) from the position shown in FIG. 6E, so that the end of the first branch 651e is received in the first aperture 674a, and the end of the second branch 652e is received in the second aperture 674b. Accordingly, the first and second branches 651e, 652e are temporarily secured in position relative to each other at the second location 655e. When the self-centering guidewire 650e is to be removed, the practitioner can slide the connector tube 656e and the connector 673 in a distal direction relative to the ferrule 659 and along the left atrial guidewire 650c (as indicated by arrow D) to disengage the connector 673 from the first and second branches 651e, 652e. The self-centering guidewire 650e can then be removed from the patient in a manner generally similar to that described above.

FIGS. 6F-6J illustrate an overall arrangement for a self-centering guidewire and a controller in accordance with a particular embodiment of the disclosure. Aspects of the embodiment can facilitate deploying the self-centering guidewire (and the right atrial guidewire) from the delivery catheter once the delivery catheter is located in the patient's heart to reduce or eliminate the likelihood for these guidewires to interfere with each other (e.g., twist together). This arrangement is also expected to be less likely to disturb the position of the self-centering guidewire once it is in the PFO because the (stiffer) delivery catheter is advanced along the self-centering guidewire for only a short distance, e.g., the distance between (a) the entrance of the vena cava to the heart, and (b) the PFO tunnel.

Figure 6F:
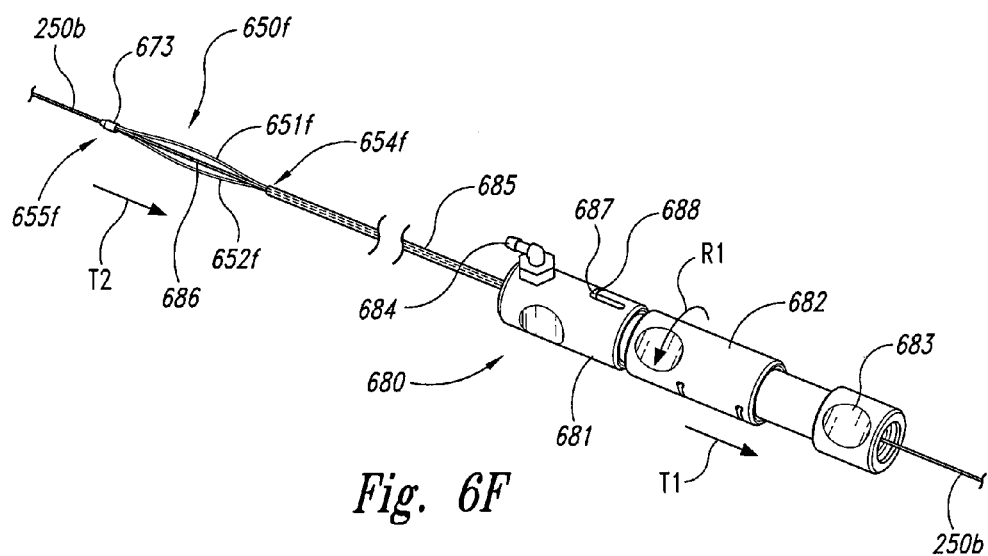

Beginning with FIG. 6F, the self-centering guidewire 650f can include a first branch 651f and a second branch 652f fixedly secured relative to each other at a first location 654f. For example, both branches 651f, 652f can be fixedly connected to a shaft 685. The first and second branches 651f, 652f can be releasably secured relative to each other at a second location 655f by a connector 673. A deployment tube 686 is attached to the connector 673 and slides within the shaft 685 to change the configuration of the self-centering guidewire 650f from a stowed position (shown in FIG. 6F) in which the guidewire 650f is configured to be carried in a delivery catheter, to a deployed position described in further detail below with reference to FIG. 6G.

The operation of the self-centering guidewire 650f can be controlled by a guidewire controller 680 that includes a housing 681, a deployment knob 682, and a connector knob 683. The deployment knob 682 is manipulated to change the self-centering guidewire 650f from the stowed position shown in FIG. 6F to the deployed position. The connector knob 683 is manipulated to release the first and second branches 651f, 652f at the second location 655f. The shaft 685 and the guidewire controller 680 are threaded over the left atrial guidewire 250b, and a lubricant fitting 684 can provide saline or another suitable, biocompatible lubricant to facilitate relative motion between the various components of the guidewire 650f and the guidewire controller 680. The guidewire is typically threaded through a catheter (e.g., the delivery catheter 230a shown in FIG. 3C), but for purposes of clarity, the catheter is not shown in FIGS. 6F-6K.

The housing 681 can include an L-shaped deployment slot 687 which receives a deployment pin 688 carried by the deployment knob 682. To deploy (e.g., expand) the self-centering guidewire 650f, the operator rotates the deployment knob 682 as indicated by arrow R1 so that the deployment pin 688 moves circumferentially within the deployment slot 687. An internal spring then forces the deployment knob 682 away from the housing 681 so that the deployment pin 688 moves axially within the deployment slot 687. The deployment knob 682 is connected to the deployment tube 686, which is in turn connected to the connector 673. Accordingly, when the deployment knob 682 moves axially as indicated by arrow T1, the connector 673 moves axially as indicated by arrow T2.

Figure 6G:
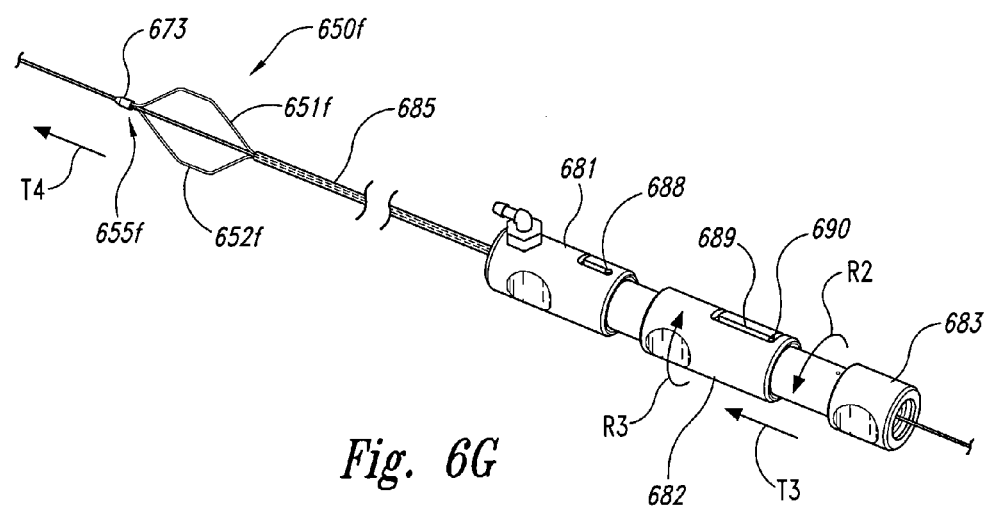

FIG. 6G illustrates the self-centering guidewire 650f in its deployed position, after the deployment knob 682 has been manipulated in the manner described above with reference to FIG. 6F. The first and second branches 651f, 652f can be formed from a shape-memory material (e.g., Nitinol) so as to bend toward the shape shown in FIG. 6G in the absence of an external force. In this configuration, the first and second branches 651f, 652f can spread and/or tighten the tissue of the primum in a manner generally similar to that described above, and an electrode can be moved through the atrial septum into the left atrium so as to seal or at least partially seal the PFO tunnel, also in a manner generally similar to that described above.

One aspect of an embodiment shown in FIGS. 6F-6G is that the deployment knob 683 is spring loaded and is not locked once it is released. As a result, the self-centering guidewire 650f will automatically adjust to PFO tunnels having different widths. For example, if the tunnel is relatively narrow, the branches 651f, 652f may not spread apart to the fullest possible extent, and the deployment knob 683 may not travel axially to the fullest possible extent. In this manner, the self-centering guidewire can automatically adjust to any tunnel having a width greater than or equal to the spread of the branches 651f, 652f in the undeployed position (FIG. 6F), and less than or equal to the spread of the branches 651f, 652f in the fully deployed position (FIG. 6G).

After the electrode has been positioned for tissue sealing (e.g., as discussed above with reference to FIG. 3H), the first and second branches 651f, 652f can be released at the second location 655f to allow the self-centering guidewire 650f to be withdrawn from the patient's body. To release the first and second branches 651f, 652f, the operator rotates the connector knob 683 as indicated by arrow R2, causing a connector pin 690 (which depends from the connector knob 683) to rotate circumferentially within a corresponding C-shaped connector slot 689 carried by the deployment knob 682. This motion can unlock the connector knob 683 and allow it to move axially. The practitioner then moves the connector knob 683 axially relative to the deployment knob 682 and the housing 681, as indicated by arrow T3, against a resistance force provided by an internal spring. The locking function provided by the connector slot 689 and the resistance provided by the internal spring can prevent the connector knob 683 from being operated inadvertently. As the connector knob 683 is advanced axially, the connector 673 moves axially away from the branches 651f, 652f, as indicated by arrow T4. Once the connector knob 683 has been advanced axially as indicated by arrow T3, it is rotated as indicated by arrow R3 so as to move the connector pin 690 circumferentially clockwise within the connector slot 689. Once the practitioner has rotated the connector knob 683 as indicated by arrow R3, the connector 673 is secured in an unlocked position, described below with reference to FIG. 6H.

Figure 6H:
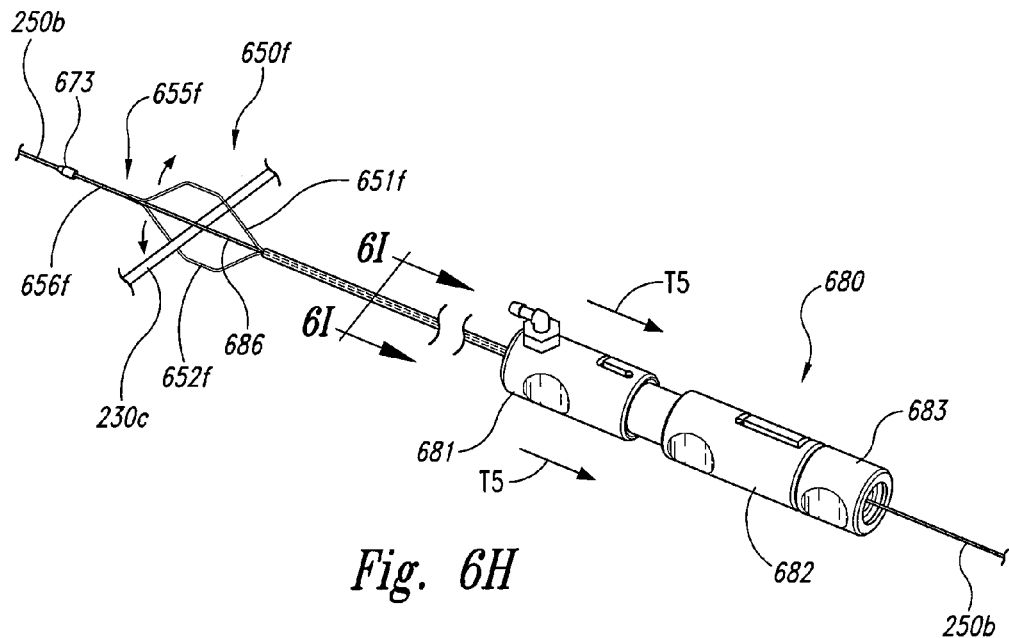

FIG. 6H illustrates the self-centering guidewire 650f and the guidewire controller 680 with the self-centering guidewire 650f in an unlocked configuration. In this configuration, a connector tube 656f, which is slideably housed within the deployment tube 686, and which is connected to the connector knob 683, has pushed the connector 673 axially along the left atrial guidewire 250b to release the first and second branches 651f, 652f at the second location 655f. Once in this configuration, the entire self-centering guidewire 650f can be removed from the patient's body by moving the guidewire controller 680 as a unit in an axial distal manner as indicated by arrows T5. Because the first and second branches 651f, 652f are no longer secured at the second location 655f, they can readily pass around the electrode catheter 230c, in a manner generally similar to that described above. The branches 651f, 652f can then collapse as they are pulled proximally through a catheter, e.g., the delivery catheter 230a shown in FIG. 3C.

Figure 6I:
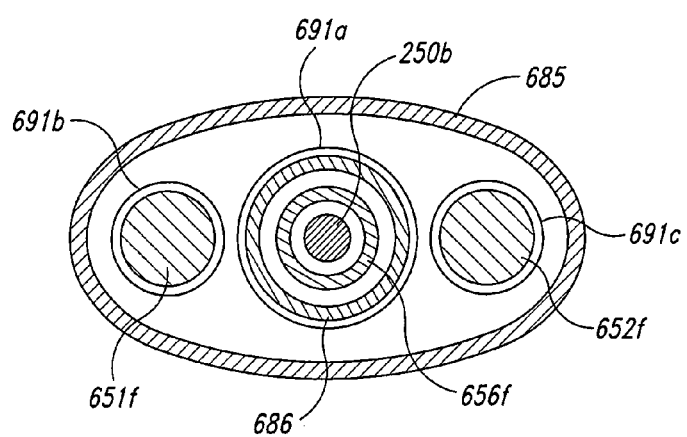

FIG. 6I is a partially schematic, cross-sectional illustration of the shaft 685, taken generally along lines 6I-6I of FIG. 6H. As discussed above with reference to FIG. 3C, the shaft can have an elliptical or other non-round cross-sectional shape so as to maintain its orientation relative to the catheter from which it extends (e.g., the delivery catheter 230a shown in FIG. 3C). The shaft 685 can be formed from a flexible material (e.g., a plastic) and can include multiple lumens that house corresponding components of the self-centering guidewire 650f. For example, the shaft 685 can include a control lumen 691a that houses the deployment tube 686, the connector tube 656f, and the left atrial guidewire 250b in a generally concentric, annular fashion. Each of these components can move relative to the other within the control lumen 691a. The shaft 685 can further include a first branch lumen 691b that houses the first branch 651f of the self-centering guidewire 650f, and a second branch lumen 691c that houses the second branch 652f. The branches 651f, 652f can be secured to the inner surfaces of the corresponding lumens 691b, 691c, so that they do not move relative to the shaft 685.

Figure 6J:
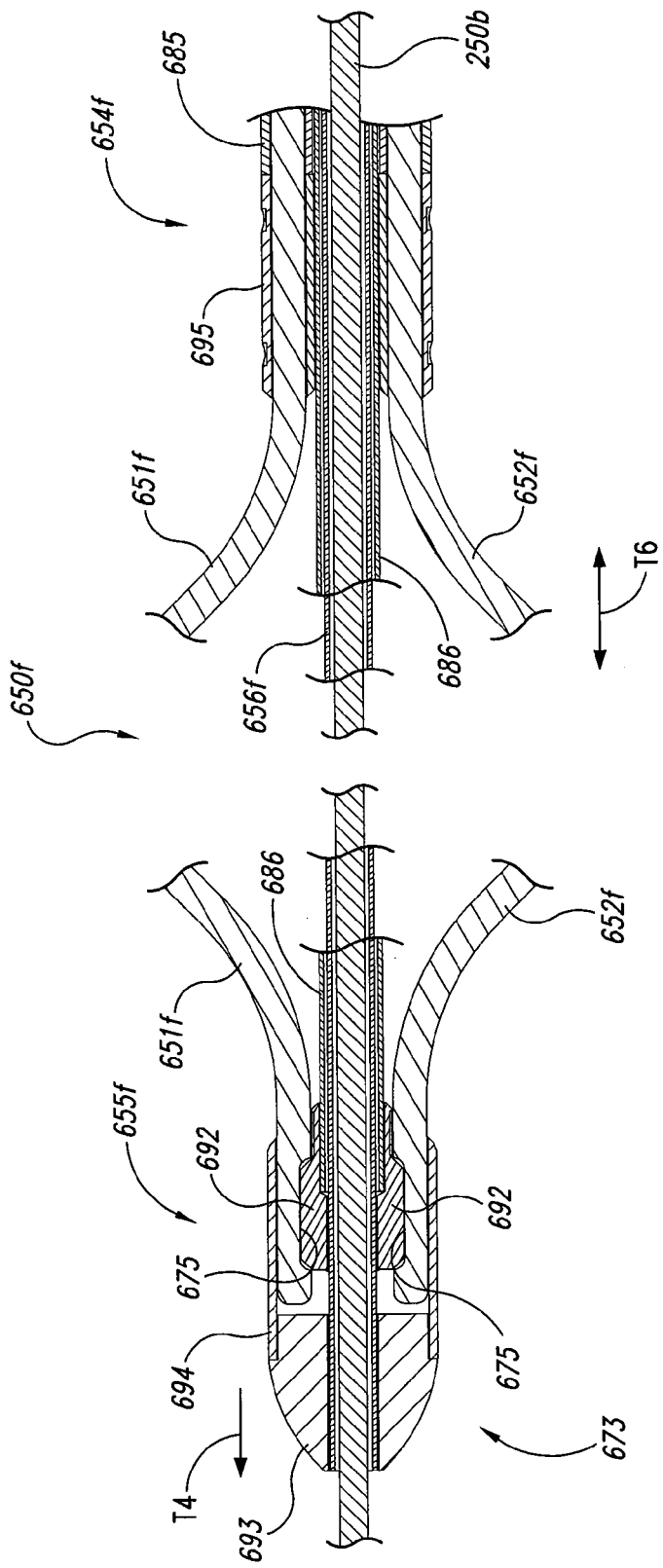

FIG. 6J is a partially schematic, partially broken illustration of the self-centering guidewire 650f illustrating details of particular components. At the first location 654f, the self-centering guidewire 650f includes a ferrule 695 that fixedly secures the first and second branches 651f, 652f to each other, e.g., via one or more spot welds. The generally rigid ferrule 695 abuts and/or is attached to the generally flexible shaft 685. The deployment tube 686 can slide relative to the shaft 685 at the first location 654f, and is connected to a pair of tabs 692 at the second location 655f. The tabs 692 snugly engage with corresponding flat surfaces 675 of the first and second branches 651f, 652f. The connector tube 656f, which is slideably positioned within the deployment tube 686, is attached to the connector 673, which in turn includes a tip 693 and a sleeve 694. The tip has an opening (e.g., a through-hole) to accommodate the left atrial guidewire 250b. The sleeve 694 fits around the distal ends of the first and second branches 651f, 652f to keep the flat surfaces 675 engaged with the tabs 692. This arrangement can significantly reduce the tendency for the branches 651f, 652f to twist out of the plane of FIG. 6J. When the deployment tube 686 is moved axially in either direction indicated by arrow T6, the connector 673, the connector tube 656f, and the first and second branches 651f, 652f at the second location 655f move as a unit relative to the first location 654f. When the connector tube 656f is moved axially as indicated by arrow T4, the sleeve 694 slides off the first and second branches 651*f*, 652*f*, allowing the first and second branches 651*f*, 652*f* to disengage from the tabs 692 so that the self-centering guidewire 650*f* can be removed from around the electrode catheter 230*c* (FIG. 6H) and removed from the patient's body, as described above with reference to FIG. 6H. In other embodiments, the self-centering guidewire 650*f* can include other arrangements that selectively lock the branches 651*f*, 652*f* at the second location 655*f*, and resist twisting when locked, and that selectively unlock the branches 651*f*, 652*f* to allow the guidewire 650*f* to be withdrawn.

Figure 6K:
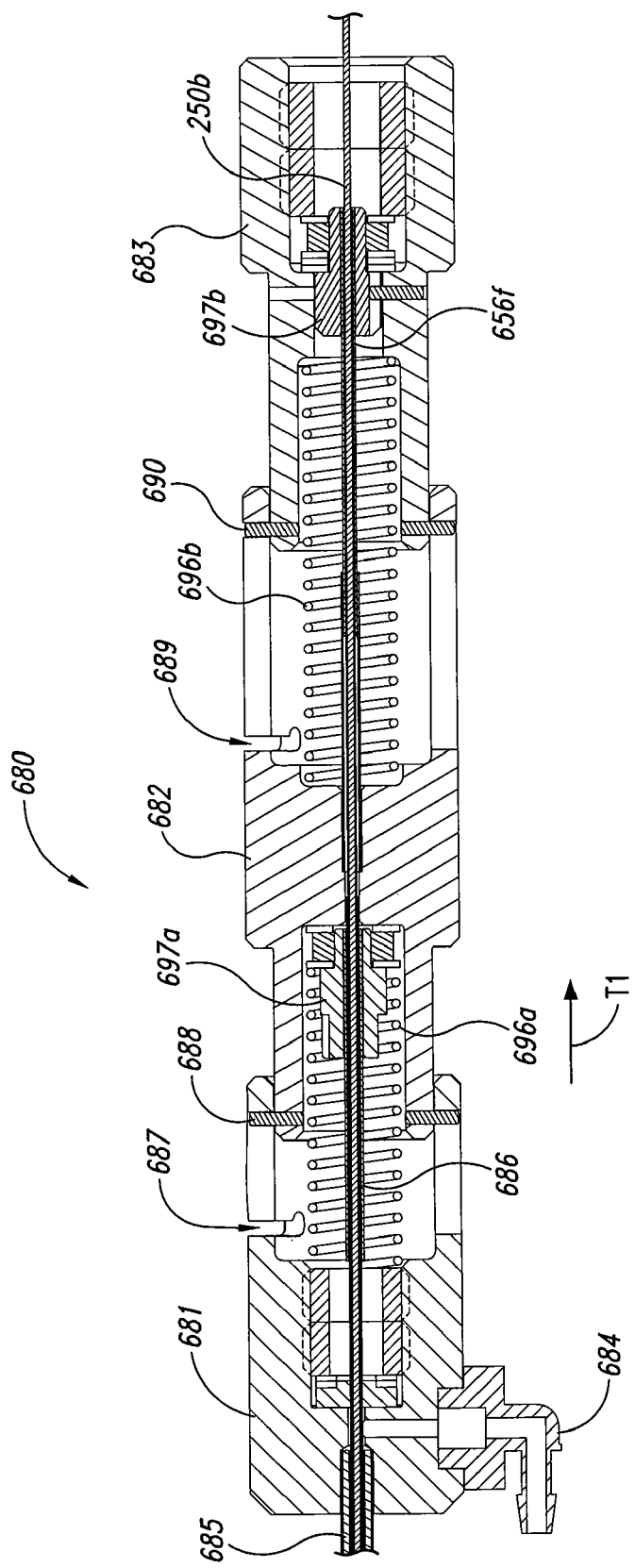

FIG. 6K is a partially schematic, cross-sectional illustration of the guidewire controller 680. The housing 681 of the guidewire controller 680 is rigidly attached to the shaft 685, and both the guidewire controller 680 and the shaft 685 are threaded over the left atrial guidewire 250*b*. The deployment tube 686 is attached to a first fitting 697*a* which is in turn forced by a deployment knob spring 696*a* into engagement with the deployment knob 682. Accordingly, the deployment knob spring 696*a* can facilitate the axial motion of the deployment knob 682 as indicated by arrow T1, and as described above with reference to FIG. 6F.

The connector tube 656*f*, which is slideably positioned within the deployment tube 686, is connected to a second fitting 697*b* which is in turn connected to the connector knob 683. A connector knob spring 696*b* forces the connector knob 683 to the position shown in FIG. 6K, so that the practitioner must overcome this force to move the connector tube 656*f* (and the associated connector 673), as described above with reference to FIG. 6G.

One feature of at least some of the foregoing embodiments is that they include a guidewire having two resilient separable portions (e.g., branches). An advantage of this feature is that it allows each portion to apply a relatively small, moderate, or otherwise non-tearing force against opposite sides or edges of the PFO tunnel, which can both stretch the tunnel and center the guidewire. When the practitioner then penetrates the septum with the penetrating guidewire and the electrode catheter, he or she can do so with greater assurance that the electrode or other energy delivery device is centered or approximately centered laterally in the tunnel. Because the branches of the self-centering guidewire are separable, the guidewire can be removed from its centered position without disturbing the electrode catheter or the tissue bond formed by the electrode catheter.

Another feature of at least some of the foregoing embodiments is that the branches, when connected, can define a generally planar enclosed shape. This shape can tend to sandwich directly between the primum and the secundum, as discussed above with reference to FIG. 3D, so that the guidewire tends not to rotate or twist once in position in the PFO tunnel. This is unlike existing guidewires having separate prongs, which may allow the guidewire to twist once it is in the PFO tunnel. In addition, at least some of the foregoing embodiments include connectors that snugly yet releasably secure the distal ends of the branches relative to each other. This is also unlike some existing guidewires having prongs with distal ends that are partially captured, but are not constrained in a manner that adequately resists twisting. For example, the flat surfaces 675 securely mated with the corresponding surfaces of the connector shown in FIG. 6E are expected to significantly stiffen the guidewire 650*f* against twisting about its major axis. The flat surfaces 675 and corresponding tabs 692, in combination with the surrounding sleeve 694 are also expected to achieve this result. In addition, the connector 673 can prevent the distal ends from inadvertently being released as the guidewire 650*f* is moved axially, proximally and/or distally, during a positioning procedure.

Accordingly, embodiments of the guidewire described above can allow the practitioner to more accurately position additional devices, e.g., penetrating guidewires and/or energy transmitters.

Figure 6M:
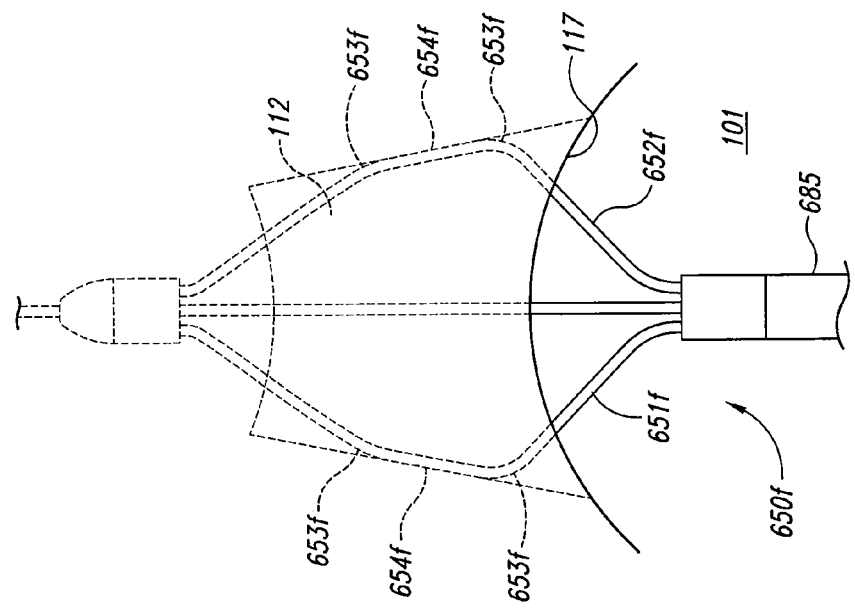
Figure 6L:
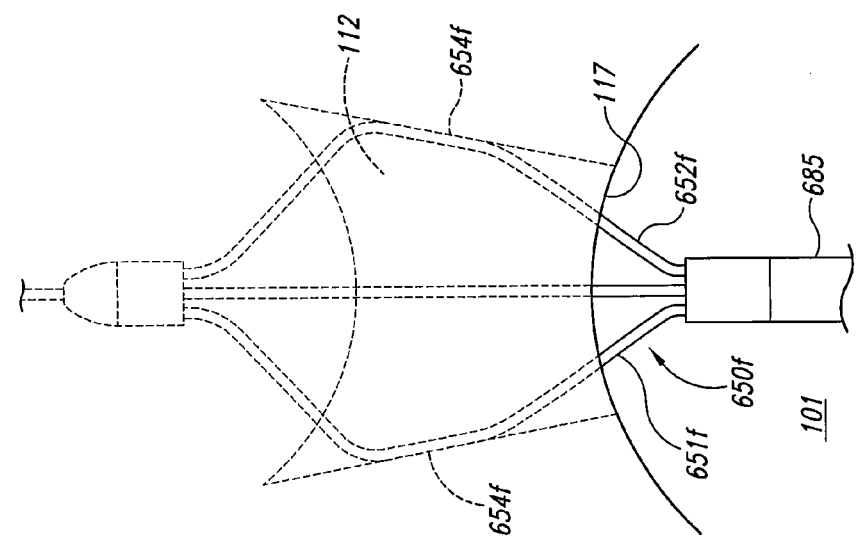

Another feature of at least some of the foregoing embodiments is that the self-centering guidewire can automatically align with the main axis of the tunnel (e.g., the axis running the length of the tunnel, from entry to exit), even if the cross-section of the tunnel varies. For example, FIG. 6L illustrates a right atrial view of the self-centering guidewire 650*f* in a PFO tunnel 112 having diverging tunnel walls. The flexible nature of the branches 651*f*, 652*f* allows them to conform to the orientation of the diverging walls, while flat portions 654*f* of the branches 651*f*, 652*f* maintain contact with the walls. Because the flat portions 654*f* are pre-formed to be flat, they will generally remain flat when the guidewire 650*f* assumes the shape shown in FIG. 6L in a diverging tunnel. FIG. 6M illustrates a right atrial view of the self-centering guidewire 650*f* in a PFO tunnel having converging walls. Again, the flexible nature of the branches 651*f*, 652*f* can allow them to conform to the converging orientation of the walls, while the flat portions 654*f* of the branches maintain contact with the tunnel walls. In particular embodiments, the branches 651*f*, 652*f* can include features that enhance this capability. For example, the branches 651*f*, 652*f* can include bends 653*f* on either side of the flat portions 654*f* that preferentially allow the flat portions 654*f* to pivot relative to the distal and proximal portions of the branches 651*f*, 652*f*. The bends 653*f* can include pivot joints, weaker (e.g., smaller diameter) regions of the branches 651*f*, 652*f*, or other suitable arrangements.

D. Devices and Methods for Penetrating Tissue

In many of the foregoing embodiments, the self-centering guidewire is used to locate the penetrating guidewire (or other penetrating member) and the electrode catheter (or other energy transmitter) relative to the PFO tunnel. In many cases, it is desirable to advance the penetrating guidewire incrementally so as to control the motion of the penetrating tip and the rate at which the tip passes through the septum. Several embodiments are described below in the context of penetrating guidewires that deliver RF energy to perform tissue penetration. In other embodiments, the penetrating guidewire can deliver other types of energy, e.g., ultrasound energy, microwave energy, laser energy and/or physical force (e.g., via a sharpened tip).

Figure 7A:
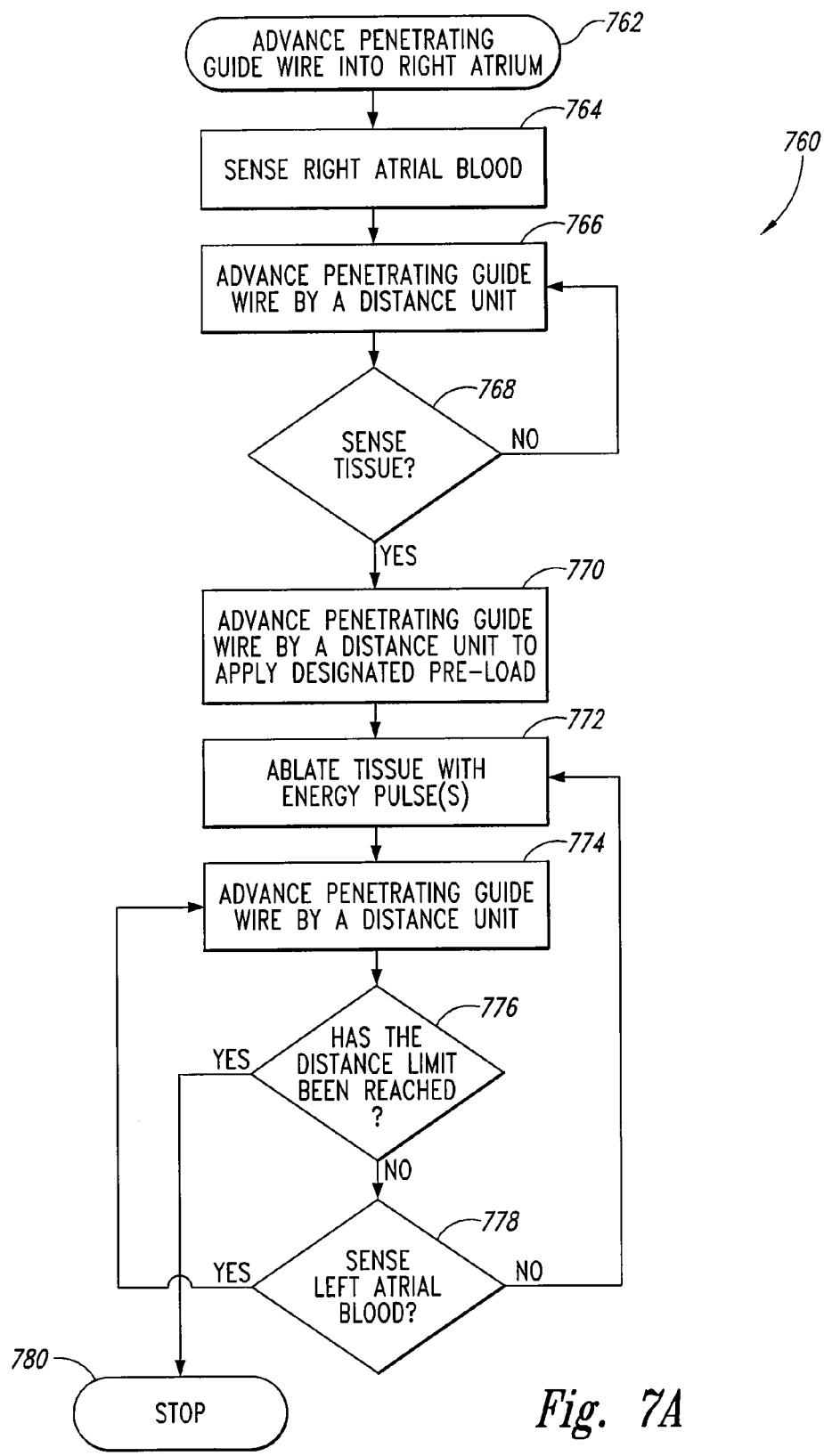
FIG. 7A is a flow diagram illustrating a process for preloading a penetrating guidewire in accordance with an embodiment of the disclosure.

FIG. 7A illustrates a process 760 for performing this technique in accordance with a particular embodiment. Process portion 762 includes advancing the penetrating guidewire into the right atrium. In process portion 764, one or more characteristics of the right atrial blood are sensed. For example, in a particular embodiment, process portion 764 includes sensing an impedance of an electrical circuit that includes the penetrating guidewire and the right atrial blood. The impedance value can then be used as a basis for comparison to the circuit impedance when the penetrating guidewire is (a) within the septal tissue and/or (b) through the septal tissue.

In process portion 766, the penetrating guidewire is advanced by a preselected or predetermined distance unit. In a particular embodiment, the distance unit can be one millimeter, and in other embodiments, the distance unit can have other values. In any of these embodiments, the distance unit can be less (and in some cases, significantly less) than the thickness of the tissue through which the guidewire will pass.

The distance unit can be measured outside the patient's body, e.g., at the proximal end 231 of the catheter 230 shown in FIG. 2.

Process portion 768 includes sensing the environment adjacent to the penetrating guidewire, and determining whether the adjacent environment is tissue, rather than blood. This process can include determining the impedance of the electrical circuit described above, and comparing the impedance to a predetermined value, for example, the impedance determined in process portion 764. In at least some cases, the penetrating guidewire will exit the delivery catheter directly into the septal tissue, and so the tissue will be sensed without advancing the penetrating guidewire any further. However, if tissue is not sensed in process portion 768, the penetrating guidewire is advanced an additional distance unit (process portion 766).

If tissue is sensed, then the penetrating guidewire is advanced by a distance unit to place a designated preload on the penetrating guidewire (process portion 770). For example, once the penetrating guidewire has encountered tissue, advancing the penetrating guidewire by an additional distance unit can cause the wire to bow and/or stretch the tissue against which it is abutted. In a particular embodiment, the distance unit by which the penetrating guidewire is advanced can be the same, whether the penetrating guidewire is passing through right atrial blood, or through tissue. In other embodiments, the distance units can be different, depending on whether the penetrating guidewire is approaching the tissue, up against the tissue, or within the tissue. For example, the distance unit can be greater when the penetrating guidewire is approaching the tissue than when it is against and/or within the tissue. The preload can have a value selected based on parameters that include patient physiology and/or characteristics of the penetrating guidewire. In particular embodiments, the preload can have a value in the range of from about 0.01 pounds to about 0.5 pounds. In a particular embodiment in which the penetrating guidewire has a diameter of about 0.013 inch and a generally spherical tip with a diameter of about 0.030 inches, the preload can be about 0.15 pounds.

In process portion 772, an energy pulse or a series of pulses is applied to the penetrating guidewire to ablate the tissue against which the penetrating guidewire abuts. The pulses can include a single pulse, a burst of pulses, and/or a series of pulse bursts. The pulses can be RF energy pulses, or pulses of other types of energy, for example, ultrasound energy. As the penetrating guidewire advances into the ablated hole made in process portion 772, the preload placed upon the guidewire in process portion 770 is released. In process portion 774, the penetrating guidewire is advanced an additional distance unit e.g., to place a new preload on the guidewire prior to ablating additional tissue.

Process portion 776 includes determining whether a distance limit has been reached, e.g., whether the guidewire has been advanced by or to a target value. In particular embodiments, the distance limit can correspond to a maximum expected thickness of the septum, or a maximum lateral dimension of the left atrium. Accordingly, process portion 786 can be used to prevent the penetrating guidewire from passing through the left atrium and into the left wall of the heart. If the distance limit has been reached, the process 760 stops at process portion 780. If not, then process portion 768 includes determining whether left atrial blood is sensed, e.g., by sensing the impedance of the circuit described above. If so, this indicates that the penetrating guidewire has passed entirely through the septum. The penetrating guidewire can then be advanced to the distance limit to provide room for additional devices deployed along the penetrating guidewire in the left atrium. Accordingly, the process 700 can return to process portion 774. If left atrial blood is not sensed, then the process returns to process portion 772, and additional tissue is ablated in an incremental manner until left atrial blood is sensed.

Figure 7B:
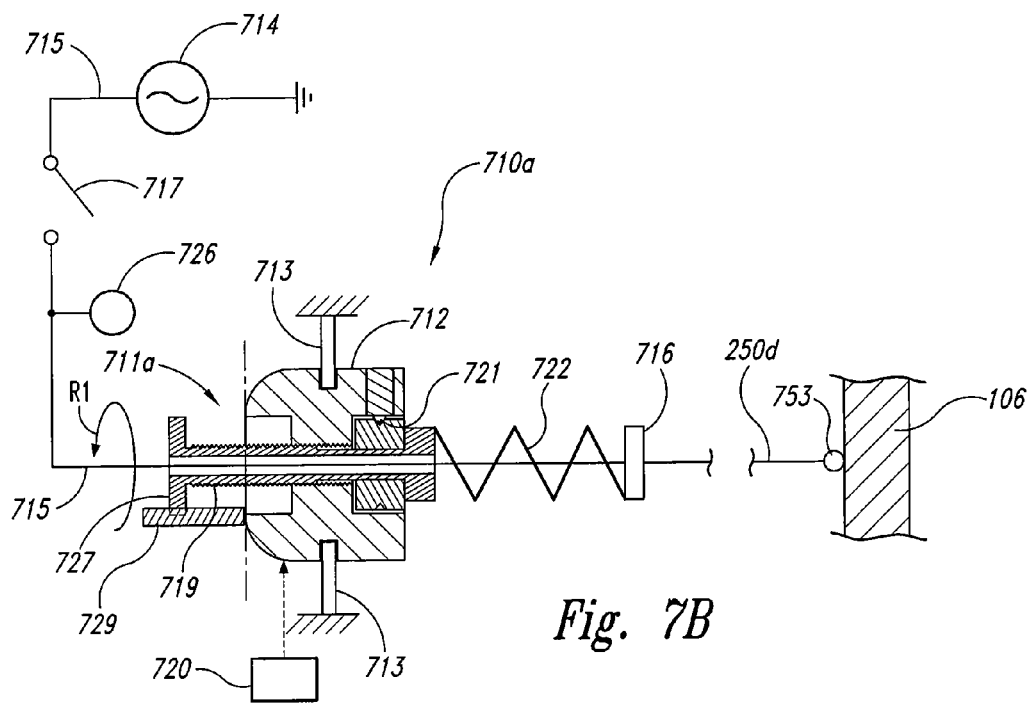
FIG. 7B-7G illustrate devices suitable for applying a preload to a penetrating guidewire in accordance with several embodiments of the disclosure.

FIG. 7B schematically illustrates a representative apparatus suitable for advancing the penetrating guidewire in accordance with an embodiment of a method described above with reference to FIG. 7A. The apparatus can include a guidewire advancer 710a that incrementally advances the penetrating guidewire 250d into and through the septum 106, e.g., through the primum, the secundum, or both. The guidewire advancer 710a can include an actuator 711a that is operatively coupled to the penetrating guidewire 250d. In a particular arrangement, the actuator 711a can include a screw 719 that slides along an axial guide 729 (e.g., a keyway). The screw 719 is connected to a spring 722 which is in turn connected to the guidewire 250d with a coupling 716. The coupling 716 can transmit electrical energy to and/or from the guidewire 250d, and accordingly can be connected to a connecting lead 715, which is in turn connected to a power source 714 via a switch 717. The power source 714 can have a relatively high output impedance (e.g., 400-1000 ohms), which can allow the penetrating tip 753 to readily begin a spark erosion process when in contact with the septal tissue. This feature can also allow the tip 753 to rapidly quench when in a blood pool. Still further, the high output impedance is expected to reduce the likelihood for the tip 753 to arc when in a blood pool, thus reducing the likelihood for forming a thrombus. A sensor 726 (e.g., an impedance sensor) can detect a characteristic of the environment in which a penetrating tip 753 of the guidewire 250d is positioned, as discussed above with reference to FIG. 7A.

In a particular aspect of the arrangement shown in FIG. 7B, the actuator 711a further includes a rotatable knob 712 that threadably engages the screw 719 and is restricted from axial movement by a retainer 713. Accordingly, the operator can rotate the knob 712 in a counterclockwise direction (indicated by arrow R1), which causes the screw 719 to axially advance along the axial guide 729 while the knob 712 is held in a fixed axial position by the retainer 713. One or more detents 721 can control the motion of the screw 719. For example the detents 721 can provide temporary and/or intermediate stops for the screw 719 as it is advanced by predetermined distances. A head 727 of the screw 719 can provide a final stop by contacting the knob 712 when the maximum number of distance units has been reached.

In a particular embodiment, the knob 712 can be rotated manually by a practitioner. In other embodiments, a motor 720 or other powered device can rotate the knob 712 to automate or at least partially automate the process of advancing the penetrating guidewire 250d. In such embodiments, the motor 720, the switch 717, and the sensor 726 can be operatively coupled together (e.g., under the direction of the controller 221 shown in FIG. 2) so that the guidewire 250d can be automatically advanced until the tip 753 penetrates through the septum 106. In further embodiments the actions of the knob 712 and the screw 719 can be reversed, e.g., the knob 712 can slide axially, and the screw 719 can rotate.

Figure 7C:
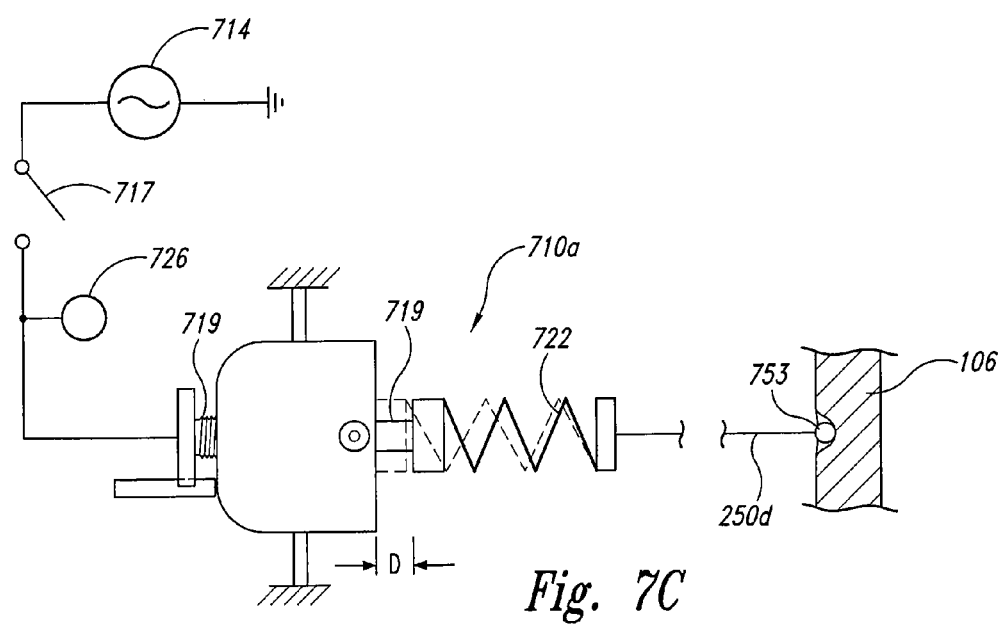

FIG. 7C illustrates the guidewire advancer 710a after the screw 719 has been advanced by a representative distance unit D. At this point, a preload has been applied to the guidewire 250d, for example, by compressing the spring 722 and/or by deforming the septum 106. The switch 717 can remain open while the preload is applied to the guidewire 250d.

Figure 7D:
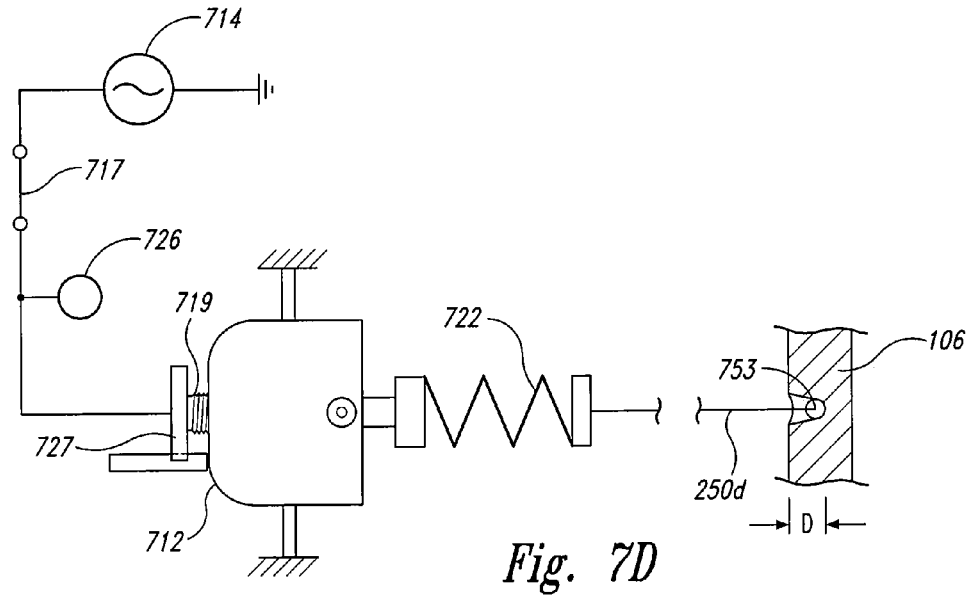

When the guidewire 250d has been advanced far enough to contact the septum 106, as indicated in FIG. 7C, and as detected by the sensor 726, the switch 717 can be closed, as shown in FIG. 7D. As electrical power is provided to the tip 753, the tip 753 ablates the septal tissue and advances by a distance unit D, relieving the compressive force (e.g. the preload) on the tip 753 provided by the septum 106 and/or the spring 722. The process shown in FIGS. 7B-7D can be repeated until the septum 106 is penetrated and/or until the head 727 engages the knob 712.

Figure 7E:
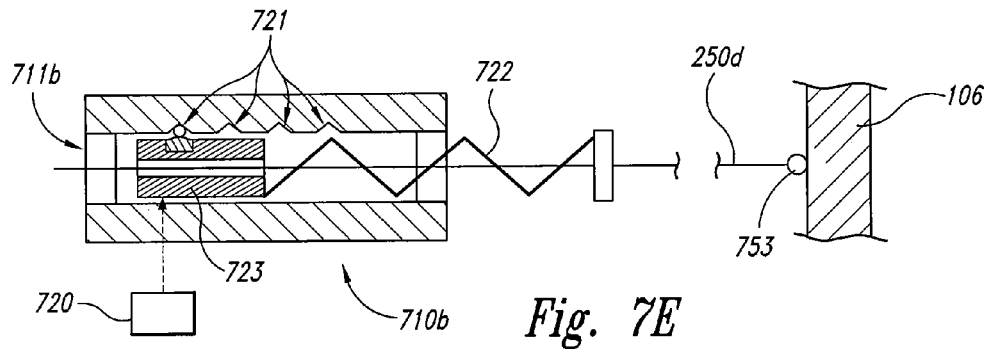

FIG. 7E illustrates a guidewire advancer 710b and associated actuator 711b configured in accordance with another embodiment of the disclosure. In one aspect of this embodiment, the actuator 711b can include a slider 723 that is coupled to the spring 722 and the guidewire 250d to advance the guidewire tip 753. The slider 723 can be operated manually or via the motor 720. In either arrangement, the guidewire advancer 710b can include one or more detents 721 to control the motion of the slider 723. For example, the detents 721 can be positioned one distance unit apart to allow the guidewire 250d to be advanced incrementally into and through the septum 106.

Figure 7F:
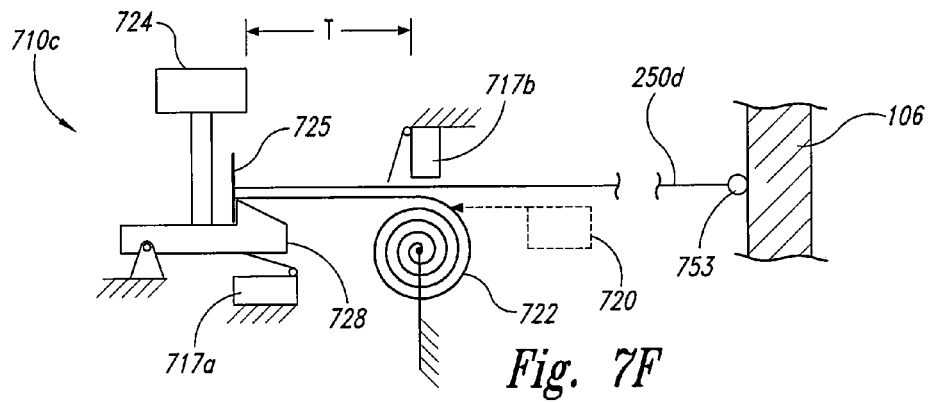

FIG. 7F illustrates a guidewire advancer 710c configured for automated operation in accordance with another embodiment of the disclosure. The guidewire advancer 710c can include a constant force spring 722 and/or a motor 720, operatively coupled to the guidewire 250d. Before the tissue penetration feature of the guidewire 250d is operated, a catch 728 is engaged with a wire stop 725 to prevent inadvertent movement of the penetrating tip 753. To begin operation, the practitioner can press a start button 724 which both releases the wire stop 725 from the catch 728, and closes an energy delivery "on" switch 717a. At this point, the spring 722 and/or the motor 720 apply an axial force to the penetrating guidewire 250d while the power source 714 (FIG. 7B) applies an electrical current to the guidewire 250d. In a particular embodiment, the tip 753 can be positioned against the septum 106 before the start button 724 is engaged, but in other embodiments, the tip 753 can be automatically advanced into contact with the septum 106 using a feedback arrangement as was discussed above with reference to FIGS. 7A-7B.

As the penetrating tip 753 presses against and ablates the septal tissue, it advances into the septum 106 while the constant force spring 722 and/or the motor 720 continue to apply an axial force that moves the tip 753 forward. In a particular aspect of this embodiment, the motion of the tip 753 can be generally continuous until the tip 753 penetrates through the septum 106 and/or until the wire stop 725 engages an energy delivery "off" switch 717b, e.g., after traveling a full travel distance T as shown in FIG. 7F. In other embodiments, the motion of the tip 753 can be controlled to be stepwise or incremental, as discussed above with reference to FIGS. 7A-7E. In still further embodiments, devices other than a constant force spring can be used to apply a generally constant force to the tip 753. Such devices include, but are not limited to, pneumatic devices and hydraulic devices.

Figure 7G:
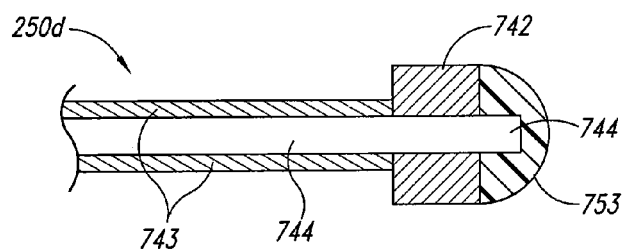

FIG. 7G is a detailed cross-sectional illustration of the penetrating guidewire 250d in accordance with a particular embodiment. The penetrating guidewire 250d can include a flexible, electrically conductive core 744 enclosed by a sheath of flexible, electrical insulation 743. The tip 753 is in electrical communication with the conductive core 744. A collar 742 or other electrically and thermally insulating member can be located between the tip 753 and the flexible electrical insulation 743. In a particular embodiment, the penetrating guidewire 250d can include features to enhance fluoroscopic visualization (or other visualization) during operation. For example, the penetrating guidewire 250d can include one or more bands or other regions of plating (e.g., a 7µ layer of gold plating) at points in a proximal direction from the tip 753. In a particular embodiment, the plating can be a continuous coating that extends from the tip 753 proximally by a distance of about two inches.

In operation, the penetrating guidewire 250d can perform as a spark erosion or spark discharge device. Accordingly, sparking produced at the tip 753 can produce microscopic explosive steam vesicles that open a region in the tissue ahead of the tip 753 and allow the guidewire 250d to penetrate. The materials for the components of the penetrating guidewire 250d can be selected to enhance this operation. For example, the tip 753 can include a thermally refractory, radio-dense or radiopaque material, such as a platinum-iridium alloy, that resists pitting and/or other types of degradation that occur in metals with lower melting points, such as steel and Nitinol. Platinum-iridium alloys are also readily machinable and swageable, and can show up well during fluoroscopic surveillance of the penetrating procedure. The conductive core 744 can be formed from a more flexible material, such as Nitinol, and the insulation 743 can reduce or prevent the loss of electrical energy along the length of the conductive core 744. The collar 742 can include a ceramic material that provides a thermal buffer between the tip 753 and the electrical insulation 743, which might otherwise suffer melting and/or other damage as a result of the sparking action at the tip 753.

One feature of particular embodiments described above with reference to FIGS. 7A-7G is that the penetrating guidewire is advanced incrementally. Accordingly, the likelihood for over-advancing the penetrating guidewire can be eliminated or significantly reduced. Another advantage associated with particular embodiments is that the process of advancing the penetrating guidewire can include applying a compressive preload on the guidewire. This arrangement can increase the efficiency with which the guidewire penetrates the septal tissue. Still another advantage associated with at least some of the foregoing embodiments is that some or all aspects of the guidewire motion can be automated or semi-automated. For example, the practitioner can manually place the guidewire 250d at or close to the septum 106, and the automated procedure can be used to penetrate the septum. This arrangement can, in at least some cases, provide for increased consistency of operation and/or increased penetration accuracy.

In at least some embodiments, selected aspects of the penetrating guidewire can be modified or eliminated. For example, in some embodiments, the final "stop" feature of the foregoing embodiments can be included, but the discrete stepwise advancement feature can be eliminated. Imaging/visualization techniques can instead be used to determine the progress of the penetrating guidewire and can optionally supplement the function of the final stop.

Returning now to FIG. 3E, the penetrating guidewire 250d can be operated in a bipolar manner, as indicated by field lines F, independently of whether or not it is controlled in accordance with the method described above with references to FIGS. 7A-7G. In particular, electrical power can be provided to the electrode tip 253 shown in FIG. 3E, and the return electrode 280b can operate as a return path for electrical current provided to both the tip 253 and a treatment electrode, e.g., the electrode 280 shown in FIG. 3F. In other embodiments, the penetrating guidewire 250d can use other return electrodes, but in an aspect of the embodiment shown in FIG. 3E, the shared return electrode 280b can reduce the overall complexity of the system.

In a particular embodiment, power can be supplied to the penetrating guidewire 250d at from about 150 volts rms to about 250 $V_{rms}$ (e.g., about 200 $V_{rms}$) and a frequency of from about 100 KHz to about 5 MHz (e.g., about 480 KHz). The power can be applied for about 2 seconds continuously in one embodiment, and another embodiment, the power can be applied over a time period that ranges from about 1 second to about 5 seconds. In still further embodiments, the power can be applied for time periods of less than 1 second. For example, from about 0.01 seconds to about 0.1 seconds.

In any of the foregoing embodiments, the motion of the penetrating guidewire 250d can be constrained, for example, via a stop device carried by the penetrating guidewire 250d and/or the delivery catheter 230b. In particular embodiments, the motion of the penetrating guidewire 250d can be constrained so that the tip 253 (at maximum displacement) is no further than five centimeters from the return electrode 280b. In other embodiments, this distance can be three centimeters or less. In any of these embodiments, the distance between the tip 253 and the return electrode 280b is relatively small, so that the electric field emanating from the tip 253 loops back to the return electrode 280b.

One feature of the foregoing bipolar arrangement for the penetrating guidewire 250d is that it can improve patient safety because the electric fields are more tightly constrained to the region of interest (e.g., the septum 106). In addition, the bipolar arrangement eliminates the need for a patient pad, which can simplify the patient treatment procedure and provide for more consistency from one patient to another. Further features of bipolar electrode arrangements are described later with reference to FIG. 6J.

E. Electrode Devices and Associated Methods

Figure 8A:
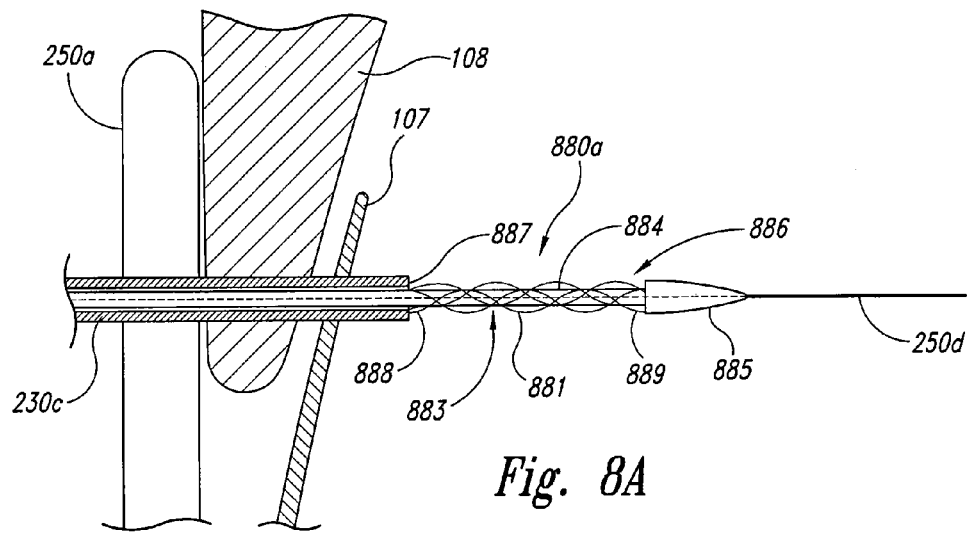

After the penetrating guidewire is inserted through the septal tissue, an electrode device or other energy delivery device can be passed along the penetrating guidewire to seal the PFO tunnel. FIG. 8A is a partially schematic, cross-sectional illustration of an electrode device 880a configured in accordance with a particular embodiment of the disclosure. The electrode device 880a can be carried by the electrode catheter 230c described above, or by another catheter. The electrode device 880a can include an electrically conductive material 881 formed from a plurality of flexible fibers. In a particular embodiment, the fibers are wrapped in a generally spiral and/or braided fashion with first ends 888 connected to a support 887 (e.g., a distal end of the electrode catheter 230c, or a ferrule carried at the distal end), and second ends 889 attached to an actuator 883. The actuator 883 can include an actuator cap 885 connected to an actuator tube 884 that fits within the electrode catheter 230c and has an axial opening through which the penetrating guidewire 250d passes. The actuator cap 885 can be formed from an electrically insulating material, e.g., a ceramic material or polymer. In some embodiments, the actuator tube 884 can extend (as a tube) through the entire electrode catheter 230c and outside the patient's body for actuation. In other embodiments, the actuator tube 884 can extend for a short distance and then connect to an actuator cable that extends alongside the penetrating guidewire 250d and outside the patients' body. In still further embodiments, the actuator tube 884 can be eliminated and replaced with a cable that attaches directly to the actuator cap 885.

The conductive material 881 forming the electrode device 880a can include a Nitinol material, another shape memory material, and/or another suitable fibrous electrically conductive material. The electrode device 880a can include a suitable number of fibers or strands (e.g., from about 16 to about 128), having a suitable diameter (e.g., from about 0.001 inches to about 0.010 inches). In a particular embodiment, the electrode device 880a can include 48 strands, each having a diameter of about 0.004 inches. In a particular embodiment, the conductive material 881 has the configuration shown in FIG. 8A when in its relaxed state. When the actuator tube 884 (and/or cable) is withdrawn proximally into the electrode catheter 230c, the actuator cap 885 draws the second ends 889 of the conductive material 881 toward the first ends 888, causing the conductive material 881 to splay outwardly from the penetrating guidewire 250d.

Electrical power is provided to the conductive material 881 via an electrical energy path 886. In a particular embodiment, the actuator 883 itself can be electrically conductive and can provide the electrical energy path 886 to the conductive material 881. In other embodiments, a separate electrical lead or other conductive member can provide the electrical energy path.

Figure 8B:
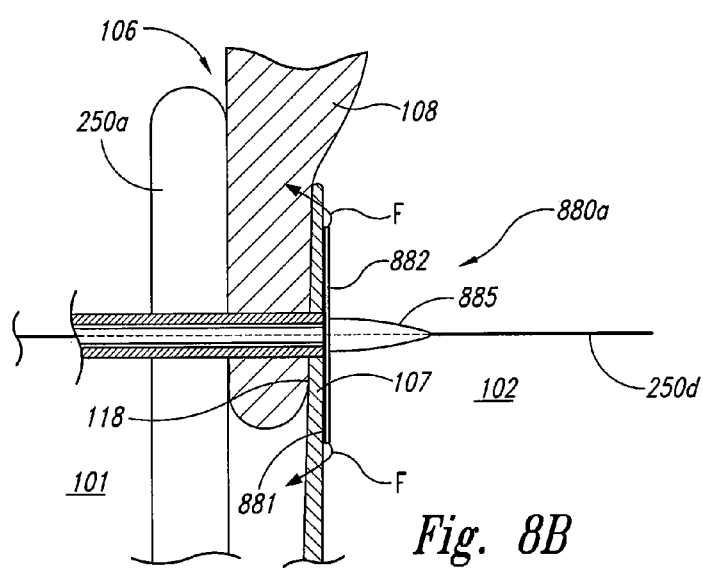

FIGS. 8B and 8C illustrate the electrode device 880a in its deployed configuration. In this configuration, the conductive material 881 can be flattened or partially flattened up against the primum 107 (as shown in FIG. 8B), and can form a petal-like configuration when seen in end view (as shown in FIG. 8C). Accordingly, the electrode device 880a includes gaps or spaces between the strands or filaments of conductive material 881. In general, the electrode device 880a can have a diameter in the range of from about 2 mm to about 30 mm (e.g., about 12 mm) when deployed. The particular diameter selected by the practitioner can depend on features that include the geometry of a given patient's PFO.

Referring now to FIG. 8B, the distal-facing surfaces of the conductive material 881 may be coated with an insulating material 882 in a particular embodiment to prevent or restrict electrical signals from being directed distally into the blood in the left atrium 102. Instead, the insulating material 882 can limit the delivery of electrical energy so as to be delivered to the septum 106 rather than throughout the left atrial region, which would otherwise provide an electrical pathway to ground. In another embodiment, the insulating material 882 can be eliminated. It is expected that eliminating the insulating material 882 may improve the manufacturability of the electrode device 880a, and in many cases may enhance the energy delivery to the primum 107 when compared to an electrode device that includes the insulating material 882. In particular, as the electrode device 880a directs energy into the septum 106, the impedance of the tissue in the septum 106 (e.g., in the primum 107) directly adjacent to the electrode device 880a increases. Accordingly, the path of least electrical resistance may move laterally away from this region. For example, the path of least electrical resistance may be through the blood located adjacent to the distal surface of the conductive material 881 in the left atrium 102, and then back into a portion of the septum located laterally from the electrode device 880a, as indicated by arrows F in both FIGS. 8B and 8C. It is expected that in at least some embodiments, the effect of the spreading current path will be to increase the radial dimension of the seal 118 formed between the primum 107 and the secundum 108 in spite of the increasing impedance of the tissue close to the conductive material 881. Accordingly, this arrangement can provide a more secure and/or more complete tissue seal 118 between the primum 107 and the secundum 108.

The foregoing effect (e.g., directing the electrical field radially outwardly) can apply to the electrode device 880a as a whole, as discussed above, and also to individual fibers or strands of the electrode device 880a. For example, FIG. 8D is a cross-sectional view of one of the fibers or strands of conductive material 881 shown in FIG. 8C, positioned against the primum 107. As energy is applied to the conductive material 881, a tissue desiccation zone 816 typically forms in the primum 107 adjacent to the conductive material 881, depending upon the density of the current at the strand. The increased impedance in the tissue desiccation zone 816 reduces current flow (and resultant heat production) therein; however, the ongoing current flow in the blood-to-tissue circuit continues, as shown by arrows F. Without the ability of the current to flow from the distal-facing surfaces of the electrode device filaments or strands (which are in contact with circulating blood), the tissue may not reach temperatures adequate to cause tissue sealing in the regions between individual strands. Accordingly, making the distal surfaces uninsulated can increase the amount of heated tissue between individual strands of conductive material 881. This in turn can improve the uniformity of the seal formed by the electrode device 880a even though it includes individual strands rather than a continuous conductive plate. This effect can be important, particularly for larger electrode devices 880a (e.g., having a diameter of 12 mm and used for sealing larger regions of tissue), for which there may exist larger spaces between individual strands.

In particular embodiments, the entire distal surface of the electrode device 880a can be uninsulated, and in other embodiments, selected portions of the distal surface can be uninsulated, and other portions can be insulated. For example, referring now to FIG. 8B, the lower or inferior portion of the distal surface can be insulated and the upper or superior portion can be uninsulated. In this manner, the heating effect produced by the electrode device 880a can preferentially be projected radially outwardly in the superior direction. Because the primum 107 may overlap the secundum 108 to a greater extent in the superior region than in the inferior region, this arrangement can concentrate the heating effect in the region(s) where a tissue seal is most likely to form (e.g., the superior region), while reducing power loss to the left atrial blood in other regions (e.g., the inferior region). This result can be particularly beneficial for larger electrode devices, e.g., those having a diameter in the range of from about 12 mm to about 18 mm.

In other embodiments, the distribution of insulation on the distal surface of the electrode device may be selected in other manners. For example, selected inferior portions of the electrode device 880a may remain uninsulated to promote primum heating even where the primum 107 does not overlap the secundum 108 so as to shrink the primum in such regions. This arrangement can reduce septal tissue "floppiness" and/or improve the tissue seal.

In particular embodiments, the practitioner may wish to monitor the temperature in the region of the tissue seal. Accordingly, the electrode device 880a can include a thermocouple 879 or other temperature sensor to provide feedback. The feedback information can be used to update energy delivery parameters, either with the practitioner "in the loop," or automatically in a closed loop fashion.

As discussed above, embodiments of the electrode device 880a include a filamentous, fibrous, stranded and/or otherwise porous and/or fluid transmissible conductive material 881. As a result, the filaments can be exposed to and cooled by blood circulating in the left atrium 102. An expected advantage of this arrangement is that the filaments can be less likely to overheat by virtue of heat conduction from the adjacent cardiac tissue, which is in turn heated by the RF energy produced by the electrode device 880a. This arrangement can also be less likely to overheat the adjacent cardiac tissue. Accordingly, the filaments can be less likely to stick to the adjacent cardiac tissue, and the tendency for clot formation can be reduced. Blood desiccation and/or coagulation might otherwise adversely affect the uniformity and/or strength of the electric field provided by the electrode device 880a. In addition, this arrangement can allow the electrode device 880a to be operated at higher powers and/or for longer periods of time without coagulating, which gives the practitioner additional flexibility and safety when performing procedures.

FIGS. 8E and 8F illustrate electrode devices having filamentous and/or fibrous conductive material 881 arranged in accordance with other embodiments of the disclosure. For example, FIG. 8E illustrates an electrode device 880b having conductive material arranged in a woven pattern and flattened in its relaxed state. In a further aspect of this embodiment, the flattened sheet of conductive material 881 can further be folded on itself, as indicated by arrows G, so as to more easily fit within the electrode catheter 230c. In an embodiment shown in FIG. 8F, an electrode device 880c includes a filamentous electrically conductive material 881 that is arranged more or less randomly, rather than in a regular pattern. When deployed, the electrode device 880c can form a shape (e.g., a "ball") that is more three-dimensional than the generally flat, petal-shaped configuration shown in FIG. 8C. An advantage of this arrangement is that it may be easier to manufacture, and/or the level of care required to place the electrode device 880c in the electrode catheter 230c may be less than is required for the electrode device 880a shown in FIGS. 8A-8D.

Figure 8G:
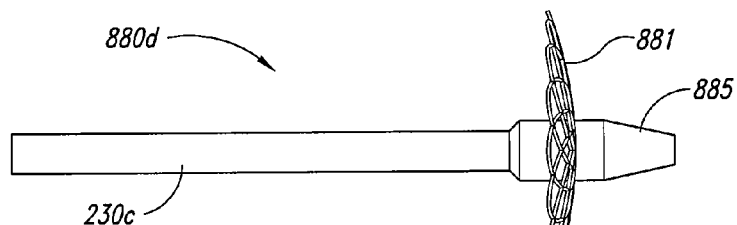

FIG. 8G illustrates an electrode device 880d having electrically conductive material 881 in the form of one or more fibers arranged in a petal configuration. The conductive material 881 can have a preformed shape once the electrode device 880d has been deployed, and in a particular embodiment, the preformed shape can include a generally concave, disk-type shape, as shown in FIG. 8G. This shape can flatten out when the electrode device 880d is pulled against the septal tissue. In particular embodiments, depending for example on the flexibility of the conductive material 881, this arrangement can result in a more uniform distribution of force on the septal tissue. The preformed shape can be formed in any of a variety of suitable manners, including heat setting the conductive material 881, permanently deforming the conductive material fibers during the assembly process, varying the helix angle of the braid along the length of the braid, and/or varying the way the braid is constrained during the assembly process and/or during the process of deploying the electrode device 880d.

Figure 8H:
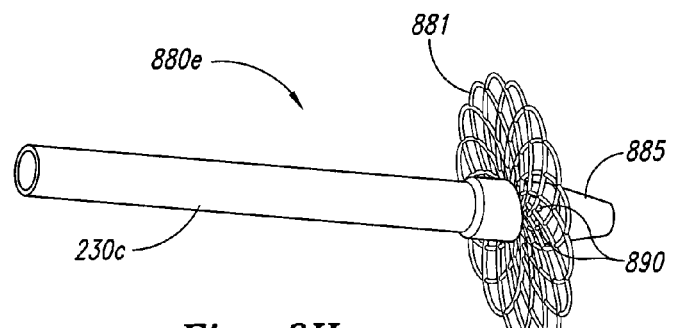
Figure 8I:
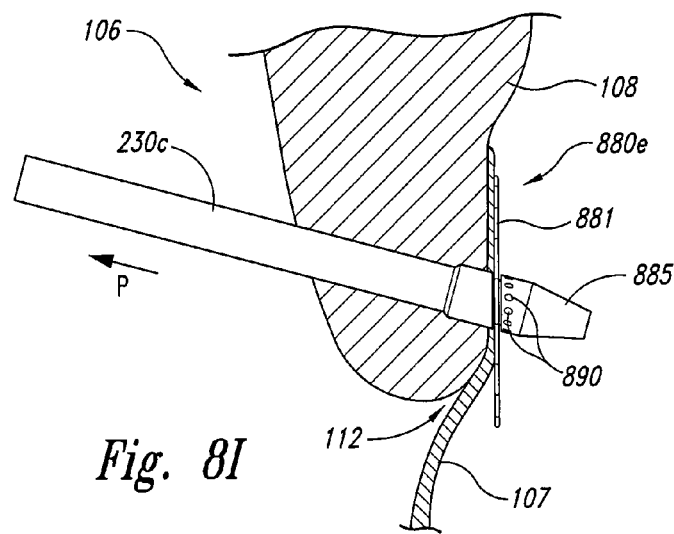

FIG. 8H illustrates an electrode device 880e configured in accordance with yet another embodiment of the disclosure. In this embodiment, the conductive material 881 can have a petal configuration positioned in a plane that is generally flat, as shown in FIG. 8C, or concave, as shown in FIG. 8G, or shaped in another manner. In any of these embodiments, the general plane in which the conductive material 881 is positioned can be tilted relative to the axis of the electrode catheter 230c at a non-orthogonal angle. When the electrode device 880e is deployed at the septum 106, as shown in FIG. 8I, the degree of tilt between the plane of the electrode device 880e and the axis of the electrode catheter 230c can help to ensure that the upper edge of the electrode device 880e makes good contact with the primum 107 and holds the primum 107 firmly against the secundum 108 in this area. The tilt angle can be selected in concert with the tissue penetration angle, which is about 105° in FIG. 8I and was discussed further above with reference to FIG. 3D. This arrangement can align the electrode device 880e with the septum 106 and provide good coaption between the primum 107 and the secundum 108.

When the electrode device 880e has an initially concave preformed shape, as discussed above with reference to FIG. 8G, applying a proximal force (as indicated by arrow P) on the electrode device 880e can cause it to flatten and provide a generally uniform compression force against the septum 106.

In other embodiments, the electrode devices can have shapes and/or configurations other than those that are explicitly shown and described above. In at least some cases, these electrode devices are shaped and/or configured to increase the uniformity with which coaption forces are applied to the septum 106, and in other cases, these electrode devices are shaped and/or configured to concentrate the coaption force in one or more areas of the septum.

Another feature of an embodiment of the electrode device 880e shown in FIGS. 8H and 8I is that it can include fluid delivery ports 890 that are in fluid communication with a fluid delivery lumen internal to the electrode catheter 230c. In operation, an electrolyte (e.g., an electrolytic fluid) can be delivered radially outwardly through the fluid delivery ports 890 to cool the distal, exposed surfaces of the electrode device 880e, and/or to prevent the accumulation of proteins or other substances at these surfaces. In another embodiment, the fluid delivery ports 890 can be positioned at the proximal side of the conductive material 881 to infuse the region between the electrode device 880e and the septum 106. In still a further embodiment, the fluid delivery ports 890 can be positioned axially between proximal and distal portions of the conductive material 891, as described further with reference to FIG. 8J. The fluid can be delivered manually or automatically. In particular embodiments, the electrolyte can include a hypertonic saline, or another biocompatible, electrically conductive fluid. Accordingly, the fluid can both cool the septal tissue at the interface with the electrode device 880e (e.g., to prevent or restrict the septal tissue from sticking to the electrode device 880e), while still allowing electrical energy to pass deeper into the septal tissue to heat the tissue and seal the PFO 112. In particular embodiments, the fluid can be chilled (e.g. to a suitable temperature below normal body temperature) to enhance the cooling effect. Whether the fluid is chilled or not, it can pass through a thermally insulated channel in the electrode catheter 230c so as to reduce or eliminate the likelihood that it will cool the septum 106 (the secundum 108 and/or the primum 107) before exiting through the delivery ports 890. Another approach is to preheat the fluid (e.g., in a range of from about 40° C. to about 90° C., or about 65° C. to about 70° C.) so that it does not chill the septum 106. It is expected that in at least some of the foregoing embodiments, the electrolytic fluid can more readily cool and/or flush the electrode device/tissue interface than can the blood in the left atrium.

In another embodiment, the fluid dispensed from the fluid delivery ports 890 can have characteristics other than those described above. For example, the fluid can include D5-W water (e.g., 5% dextrose in water), or another electrically non-conductive, or generally non-conductive, fluid that can provide cooling for the electrode device 880e. In this embodiment, the electrically non-conductive nature of the fluid can prevent the loss of electrical power to the adjacent blood field. In either embodiment, the fluid can act to prevent or reduce the accumulation of clotting proteins at the electrode device 880e, via one or more mechanisms. For example, the flow of fluid can flush such proteins from the electrode device 880e. In addition to or in lieu of flushing the proteins, the ability of the fluid to reduce the temperature of the electrode device 880e can reduce or eliminate protein accumulations. Still further, when the fluid is electrically non-conductive, it can displace the electrically conductive blood away from the electrode device 880a, so as to create an electrically non-conductive region around the electrode device 880e and preferentially direct current into the septal tissue.

Figure 8J:
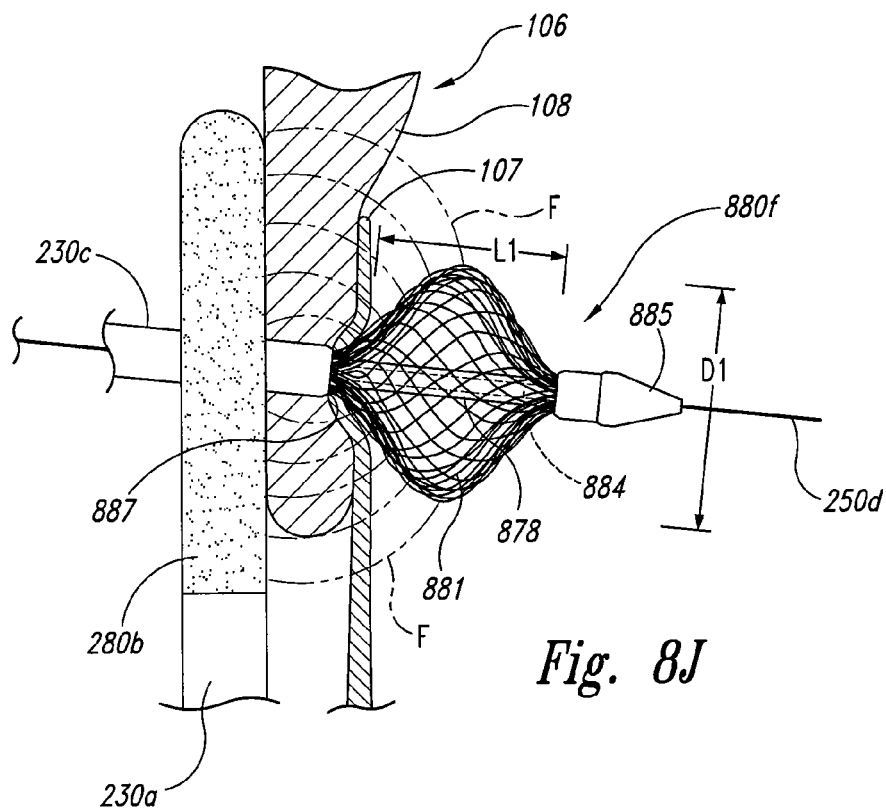

In any of the foregoing embodiments, the fluid can include constituents that provide functions other than (e.g., in addition to) those described above. For example, the fluid can include an ultrasound contrast agent to allow the fluid to be visualized more readily via ultrasound techniques. In any of the foregoing embodiments, the fluid can be provided at a suitable rate through suitably sized delivery ports 890. For example, the electrode device 880e can include 8-16 ports 890 having diameters of 0.005 inches, and the fluid can be provided at a rate of from about 1 ml/minute to about 100 ml/minute. In particular embodiments, the fluid can be pulsed. For example, the fluid flow can be active or active at a first rate during portions of the cardiac cycle when there is a low blood flow rate past the electrode device 880e, and the fluid flow can be inactive or active at a second rate less than the first rate during portions of the cardiac cycle when there is a higher blood flow rate past the electrode device 880e. Changes in the fluid flow rate can be based at least in part on changes in left atrial and/or right atrial pressure, and/or based on EKG data. In a particular embodiment, the system can include pressure transducers positioned in both the left and right atria, and coupled to a controller to vary the fluid flow rate in accordance with changes in the left atrial pressure and/or changes in the difference between left and right atrial pressures. Varying the flow rate can reduce the volume of fluid injected into the patient, while preserving a cooling effect on the electrode device 880e. Any of the foregoing aspects of fluid delivery can be controlled by the controller 221 as shown in FIG. 2, e.g., via programmed, computer-based instructions As discussed previously, it is believed that the mechanism by which the interface between an electrode device 880e and the adjacent septal tissue 106 heats up is not due to directly heating the electrode device 880e as current is passed through it, but is instead due to heat that is conductively transferred back to the electrode device 880e from the adjacent septal tissue 106, which is in turn heated by absorbing RF radiation from the electrode device 880e. Accordingly, embodiments of the disclosure are directed to devices and techniques that facilitate cooling an electrode device without unduly sacrificing heat applied to the septal tissue 106 for closing the PFO. For example, FIG. 8J illustrates an electrode device 880f deployed relative to the primum 107 and the secundum 108 in accordance with a particular embodiment of the disclosure. The electrode device 880f can include a filamentous electrically conductive material 881 connected at one end to a support 887 (e.g., the end portion of the electrode catheter 230c) and at the other end to an actuator cap 885. The actuator cap 885 is in turn moved by an actuator tube 884 that slides within the electrode catheter 230c. A stop tube 878 or other suitable device restricts the axial motion of the actuator cap 885 toward the support 887. Accordingly, when the actuator cap 885 is drawn proximately into contact with the stop tube 878, the electrode device 880f assumes an ellipsoid shape, generally as shown in FIG. 8J. The ellipsoid can have any of a variety of aspect ratios. For example, in a particular embodiment, the electrode device 880f can have a generally spheroidal shape, with a diameter D1 approximately equal to an overall length L1. In still further embodiments, D1 and L1 can have values of about 9 mm. In other embodiments, the electrode device can have variations on this shape, as described later with reference to FIGS. 8K and 8L. The electrode device 880f can optionally include fluid delivery ports 890 (FIG. 8I) positioned between the support 887 and the actuator cap 885. However, it is expected that in at least some embodiments, the cooling effect resulting from the shape and porous nature of the electrode device 880*f* will eliminate the need for fluid delivery ports.

In a particular aspect of the embodiment shown in FIG. 8J, the electrode device 880*f* operates in a bipolar manner, for example, via the return electrode 280*b* carried by the delivery catheter 230*a*. Accordingly, electric field lines (shown as phantom lines F in FIG. 8J) generated when current is applied to the electrode device 880*f* tend to form a pattern that is directed back toward the return electrode 280*b*. One expected result of this arrangement is that more of the electrical current generated by the electrode device 880*f* will be directed into the primum 107 and the secundum 108, rather than distally into the adjacent blood field. Another result is that the patient need not have a patient pad or plate in contact with the patient's skin to provide a return electrical path. This can simplify the system and reduce the number of components the practitioner must track. In addition, in at least some embodiments, this bipolar arrangement can increase the predictability and repeatability of the tissue sealing procedure. For example, it is expected that the patient-to-patient impedance variations between the two bipolar electrodes will be less than the variation between a monopolar electrode and a remote patient pad. In particular, the electrode 880*f* can have a relatively low impedance. If the impedance at the skin/pad interface varies significantly, this can have a dramatic effect on the impedance of the overall circuit, and therefore on the efficacy and/or efficiency of the tissue sealing process.

One feature of the ellipsoid/spheroid shape of the electrode device 880*f* is that it has fewer corners or edges than flat electrode devices, for example the electrode device 880*e* described above with reference to FIGS. 8H and 8I. As a result, it is expected that the likelihood for current density concentrations at such edges is significantly reduced or eliminated, producing a more uniform electrical field within the septal tissue 106. Another feature of this arrangement is that a relatively small portion of the electrode device 880*f* is actually in contact with the primum 107. As a result, the electrode device 880*f* is expected to receive less heat from the septal tissue 106 than is an electrode that is placed flat up against the primum 107. Nevertheless, the ellipsoidal (and in a particular embodiment, spheroidal) shape of the electrode device 880*f* can not only contact the primum 107 and provide a coapting force, but it can also conform the primum 107 to have a concave shape, which can in turn stretch the primum 107 and extend the radius of the coapting force between the primum 107 and the secundum 108 beyond the region of the primum 107 that is in direct contact with the electrode device 880*f*. In addition, this arrangement, in combination with the overall porous nature of the electrode device 880*f* provided by the filamentous conductive material 881 allows for greater cooling by the adjacent blood. This in turn reduces the likelihood for forming clots at the electrode device 880*f* and/or causing the electrode device 880*f* to stick to the primum 107. The bipolar electric field (which tends to direct more energy to the septum 106 and less into the left atrial blood) is also expected to reduce the likelihood for clotting. Optionally, the electrode device 880*f* can include heparin or another antithrombotic coating to reduce or prevent clot formation. At the same time, the shape of the electrode device 880*f* is expected to provide a coaption force sufficient to clamp the primum 107 and the secundum 108 against each other between the electrode device 880*f* and the delivery catheter 230*a*.

Still another feature of at least some embodiments of the foregoing arrangement is that the shape and radius of the electrode device 880*f* can be controlled by varying the movement of the actuator tube 878. For example, the practitioner can deploy the electrode device 880*f* by different amounts to produce corresponding different shapes, including those described below with reference to FIGS. 8K and 8L. The particular shape selected by the practitioner can depend on size and/or geometry of a particular patient's PFO.

When power is applied to the electrode device 880*f* (and/or other electrode devices described herein), it can be applied in a number of manners. For example, in one embodiment, the power can be applied to the electrode device 880*f* as a generally continuous high-frequency stream of pulses. In other embodiments, the power can be modulated to achieve particular results. For example, in a particular embodiment, the power can be provided at different amplitudes during different phases of the tissue sealing process. In particular, the power can be provided during a first phase at a first power level and during a second phase at a second power level higher than the first. During the first phase, the power applied to the septal tissue 106 can produce one or both of the following effects. First, it can pre-shrink the septal tissue 106 (e.g., the primum 107 and/or the secundum 108) without sealing the tissue together. More particularly, the power can be applied at an amplitude high enough to heat the septal tissue 106 sufficiently to cause it to shrink, but not so high as to cause it to seal. For example, the tissue can reach a temperature of less than 100° C. during the first phase. Second, applying heat to the septal tissue 106 in this manner can pre-desiccate the tissue, e.g., purge or at least partially purge the tissue of water before the primum 107 is sealed to the secundum 108. During the second phase, the pre-shrunk and/or pre-desiccated tissue is sealed by applying power at a higher amplitude and heating the tissue to a higher temperature (e.g., about 100° C.).

In particular embodiments, the power can be selected in a manner that depends upon patient-specific characteristics and/or specific characteristics of the electrode device 880*f* and/or other features of the overall system. For example, power can be applied in the range of from about 10 watts to about 60 watts for a period of about 2 seconds to about 120 seconds during the initial phase, and can be applied at a higher power (e.g., 12 watts to about 100 watts for a period of about 2 seconds to about 180 seconds) to seal the septal tissue during the second phase. Particular values selected within the foregoing ranges can depend upon factors that include whether the electrical power is provided in a monopolar manner or a bipolar manner, the size and shape of the electrode device, and/or the shape or characteristics of a particular patient's secundum 108 and/or primum 107.

One expected advantage of the foregoing arrangement is that pre-shrinking the septal tissue 106 can reduce the likelihood that the tissue will shrink during the tissue sealing process. Accordingly, the sealed tissue is expected to have fewer shear stresses and is therefore expected to remain intact for a longer period of time and/or (in the case of an initially incomplete seal) it is expected to more quickly form a complete seal as a result of the body's natural healing processes. By pre-desiccating the septal tissue, embodiments of the foregoing process can reduce or eliminate the presence of water in the septal tissue when higher power is applied to the septal tissue for sealing. This in turn can reduce the likelihood that such residual water will vaporize as the tissue is sealed under higher amplitude power, thus reducing the likelihood for disrupting the tissue seal as the vaporized water attempts to escape from the sealed region.

In another embodiment, the power applied to the electrode can be provided at a duty cycle of less than 100% (e.g., with the power off during certain intervals) so as to increase the efficacy of the process. For example, it has been observed that the surface of the primum 107 exposed in the left atrium can cool much more quickly than the tissue located at the interface between the primum 107 and the secundum 108, at least in part due to the enhanced cooling effect provided by blood in the left atrium as it passes directly adjacent to the exposed left atrial surface of the primum 107. By interrupting the power provided by the electrode device 880*f* to the septal tissue 106, the exposed surface of the primum 107 can cool relatively rapidly, while the temperature of the tissue at the interface between the primum 107 and the secundum 108 remains relatively high. For example, in at least some cases, there can exist a 30°-45° temperature difference between the exposed left atrial surface of the primum 107 and the interface between the primum 107 and the secundum 108. The ability to achieve this temperature differential can be enhanced by using a duty cycle of less than 100% Representative duty cycles include a 75% duty cycle (with power on for 15 seconds and off for 5 seconds), a 67% duty cycle (with power on for 14 seconds and off for 7 seconds), and an 84% duty cycle (with power on for 5 seconds and off for 1 second). In other embodiments, the duty cycle can have other characteristics with ranges of from about 50% to about 90%, durations ranging from about 1 second to about 10 minutes, and the total number of cycles ranging from 1 to about 1,000.

Figure 8K:
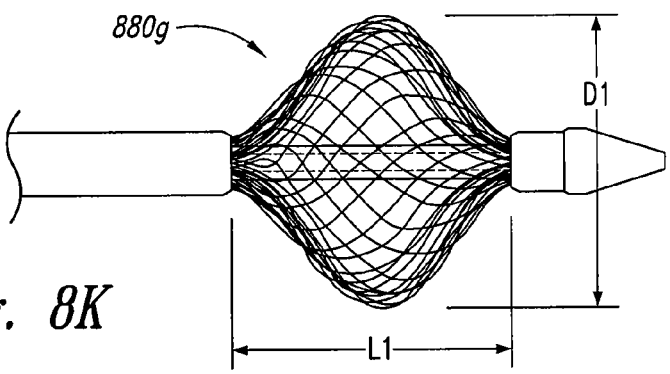
Figure 8L:
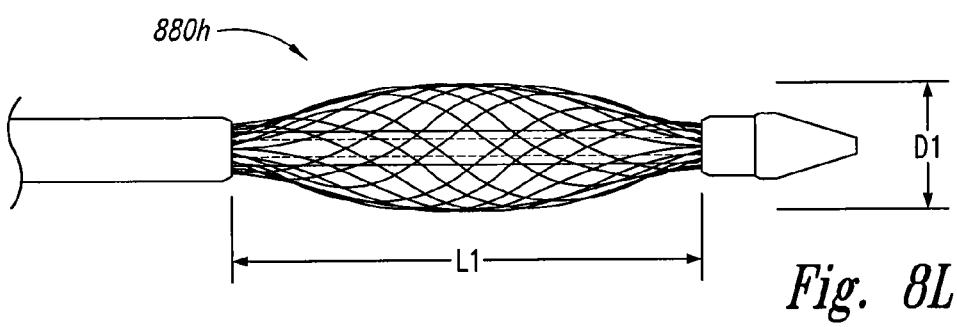

In other embodiments, electrodes having shapes similar at least in part to those described above can be operated in a generally similar manner to that described above with reference to FIG. 8J. For example, as shown in FIG. 8K, an electrode device 880*g* can have an aspect ratio D1/L1 of up to approximately 1.5 or more, to form an oblate spheroidal shape. In a particular aspect of this embodiment, D1 can have a value of about 10.6 mm. As shown in FIG. 8L, another electrode device 880*h* can have an aspect ratio D1/L1 that is less than 1.0 to form a generally prolate spheroid. In a particular aspect of this embodiment, D1 can have a value of less than 9 mm. In still further embodiments, the electrode device can have shapes other than those specifically described above and shown in the Figures.

Figure 9A:
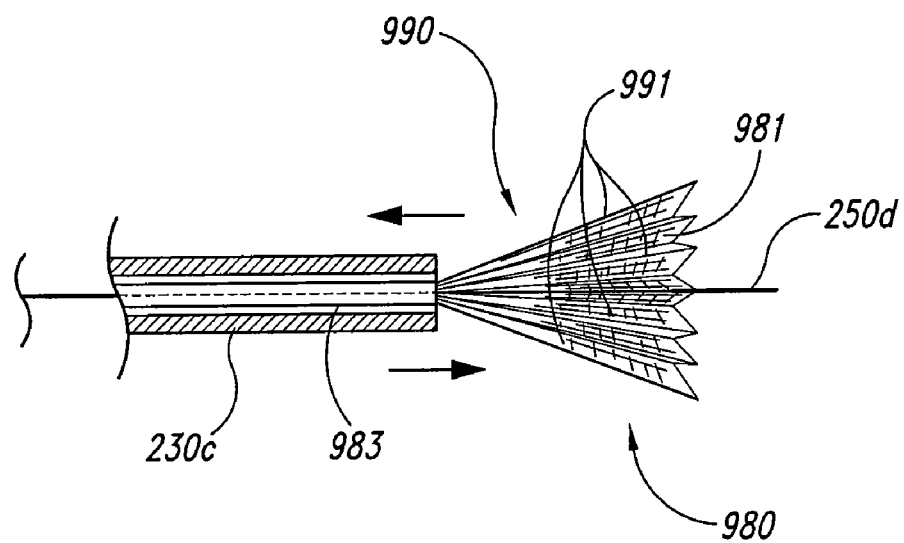
FIGS. 9A and 9B illustrate an electrode device that includes a conductive sheet configured in accordance with an embodiment of the disclosure.

FIG. 9A is a partially schematic, cross-sectional side view of an electrode device 980 configured in accordance with another embodiment of the disclosure. The electrode device 980 can include a conductive sheet 981 carried by a support structure 990. In a particular embodiment, the conductive sheet 981 can include a conductive fabric, for example, a fabric woven from conductive strands or fibers. The conductive fibers or strands can be fully conductive (e.g., metal strands) or partially conductive (e.g., polyester or other non-conductive strands coated or deposited with a conductive material). In another embodiment, the conductive sheet 981 can include a non-conductive substrate coated with a conductive material, for example, a flexible polymer sheet coated with a deposited conductive material, such as gold and/or silver. In a particular aspect of this embodiment, the substrate material can be flexible but generally not stretchable (e.g., Mylar®), so as to reduce the likelihood for the conductive material to flake off.

Figure 9B:
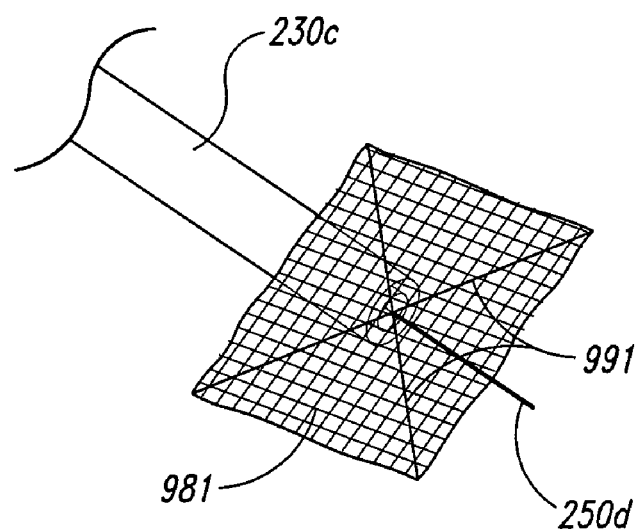

The support structure 990 can include struts 991 (e.g., Nitinol struts) connected between the conductive sheet 981 and an actuator 983. In a particular embodiment, the struts 991 are biased or pre-formed to a position that is at least approximately orthogonal relative to the penetrating guidewire 250*d*. When the electrode device 980 is stowed, the struts 991 are folded within the electrode catheter 230*c* and the conductive sheet 981 is furled. When the electrode device 980 is deployed, the struts 991 can move outwardly, as shown in FIG. 9B to unfurl the conductive sheet 981. The electrode device 980 can be deployed to form the generally flat shape shown in FIG. 9B, or it can include a stop (generally similar to that described above with reference to FIG. 8J) so as to form a pyramidal shape like that shown in FIG. 9A when fully deployed. Such an arrangement can produce at least some of the beneficial effects described above with reference to FIG. 8J.

FIGS. 10A and 10B illustrate an electrode device 1080 configured in accordance with another embodiment of the disclosure to deploy in a manner somewhat similar to that described above with reference to FIGS. 9A-9B. In a particular aspect of this embodiment, the electrode device 1080 includes a flexible conductive material 1081 electrically connected to an electrical energy path 1086 (e.g., a leadwire) and attached to a support structure 1090. The support structure 1090 can include flexible, resilient struts 1091 having first ends attached to an actuator 1083 at an electrode attachment or anchor 1093. The second ends of the struts 1091 can be connected to a slider 1092 (e.g., another anchor) that slides axially along the actuator 1083. Each of the struts 1091 can include a spring loop 1099 that tends to force the struts 1091 into a triangular shape. When stowed, the struts 1091 are forced by the interior walls of the electrode catheter 230*c* to be approximately parallel to the penetrating guidewire 250*d*. When deployed, as shown in FIG. 10B, the actuator 1083 moves the electrode device 1080 out of the catheter 230*c*. Once the electrode device 1080 emerges from the catheter electrode 230*c*, the struts 1091 can assume a generally triangular shape. The electrode attachment 1093 remains fixed, while the slider 1092 slides in a proximal direction (indicated by arrow H) to accommodate the radially expanded shape of the struts 1091.

Figure 11A:
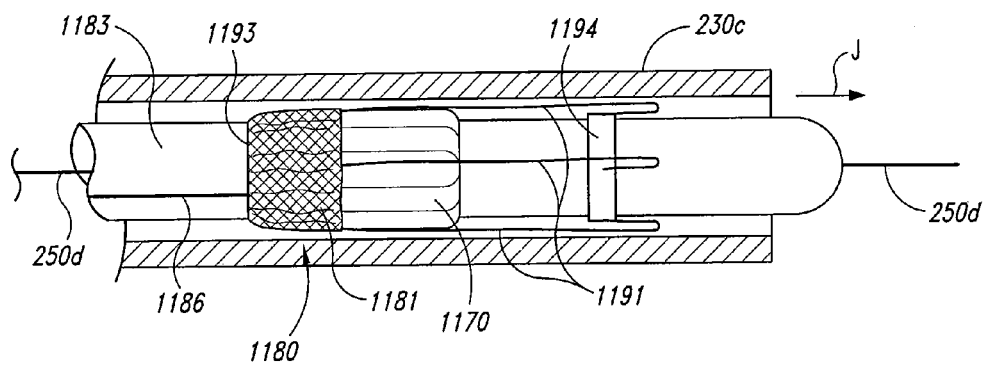
FIGS. 11A-11C illustrate an electrode device and an inflatable member for deploying the electrode device.
Figure 11B:
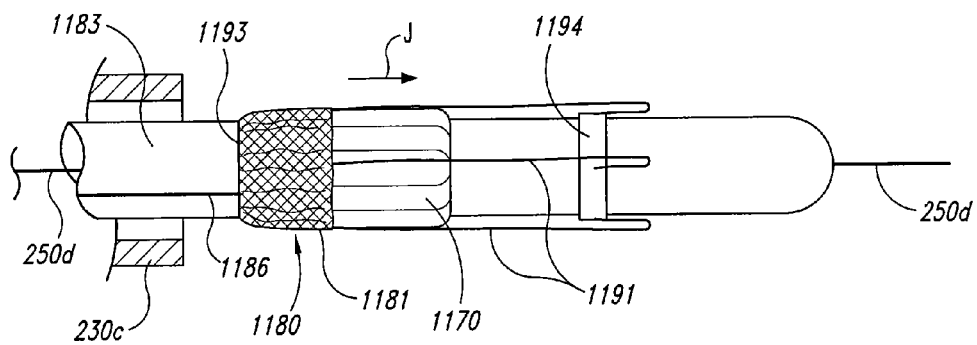
Figure 11C:
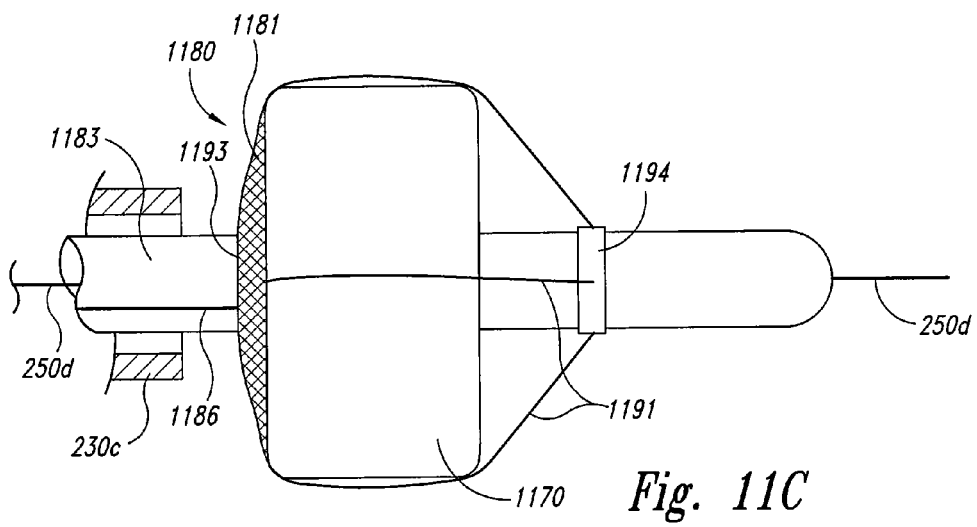

FIGS. 11A-11C illustrate an electrode device 1180 that includes a conductive material 1181 deployed, at least in part, by an inflatable member 1170 in accordance with another embodiment. The conductive material 1181 can be secured to an actuator 1183 at an electrode attachment or anchor 1193. Flexible support lines 1191 extend in a distal direction from the conductive material 1181 to a collar 1194 (e.g., another anchor) that is fixed relative to the actuator 1183. A wire or other conductive element provides an electrical energy path 1186 to the conductive material 1181. The inflatable member 1170 can be inflated with saline, contrast, or another suitable fluid. In a particular embodiment, the inflation fluid can be circulated through the inflatable member 1170 via supply and return conduits, and can accordingly provide functions in addition to inflating the inflatable member 1170. Such functions can include cooling the electrode device 1180.

When the actuator 1183 is moved in a distal direction (indicated by arrow J), it moves the electrode device 1180 out of the catheter 230*c*, as shown in FIG. 11B. As shown in FIG. 11C, the inflatable member 1170 can then be inflated to unfurl the conductive material 1181. The inflatable member 1170 can bear outwardly on the electrode support lines 1191, placing the electrode support lines 1191 under tension, which secures the conductive material 1181 in the deployed or unfurled configuration. In this embodiment, and in other embodiments that include an inflatable member, (e.g., the inflatable member 270 shown in FIG. 3G) the practitioner may in some cases select the degree to which the inflatable member is inflated based on the particular patient's PFO physiology. For example, the inflatable member 1170 can be partially inflated to allow the conductive material 1181 to assume a convex shape when drawn against the septum, or it can be more fully inflated so as to assume a flatter shape.

One aspect of an embodiment shown in FIGS. 11A-11C is that the inflatable member 1170 and the electrode device 1180 need not be intimately connected to each other, as is the case with an electrode device that includes a conductive coating applied to, and in continuous direct contact with, the exterior surface of the inflatable member. Instead, the inflatable member 1170 and the electrode device 1180 can be movable relative to each other. For example, the inflatable member 1170 shown in FIGS. 11A-11C can erect or deploy the electrode device 1180 by acting on the electrode support lines 1191. When fully inflated, the inflatable member 1170 can be in surface-to-surface contact with the electrode device 1180 to provide shape and support to the electrode device 1180, but the inflatable member 1170 and the electrode device 1180 can collapse separately. An expected advantage of this feature is that the material forming the electrode device 1180 need not be bonded directly to the inflatable member 1170, and as a result, is less likely to deteriorate, e.g., due to flaking off the inflatable member 1170. An additional expected advantage is that this arrangement can allow greater flexibility for the manufacturer when choosing materials and configurations for both the electrode device 1180 and the inflatable member 1170.

Figure 12:
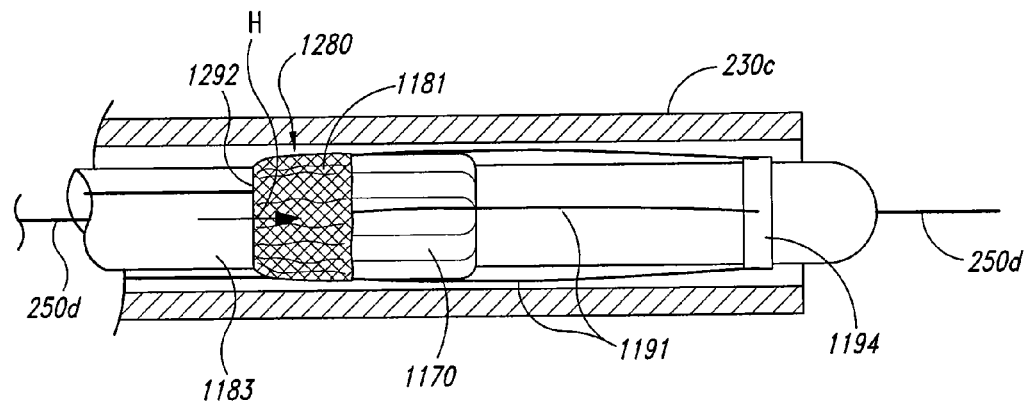
FIGS. 12 and 13 illustrate electrode devices that are deployed with inflatable members in accordance with further embodiments of the disclosure.

FIG. 12 illustrates an electrode device 1280 having at least some features generally similar to those of the electrode device 1180 described above, except that the conductive material 1181 slides relative to the actuator 1183 at a sliding interface 1292, while the collar 1194 is fixed. When the electrode device 1280 is moved out of the catheter 230c, and the inflatable member 1170 is inflated, the conductive material 1181 can slide distally toward the inflatable member 1170 along the actuator 1183, as indicated by arrow H. It is expected that this arrangement can increase the likelihood for the conductive material to have a generally flat surface facing toward the primum 107 (FIG. 8A) when deployed. In other embodiments, the inflatable member 1170 can have other shapes (e.g., rounded, spheroid, or ellipsoid shapes) to produce correspondingly shaped electrode device surfaces. In still further embodiments, the shape of the inflatable member 1170 can be changed (e.g., by varying the inflation pressure) to conform to an individual patient's septal geometry.

Figure 13:
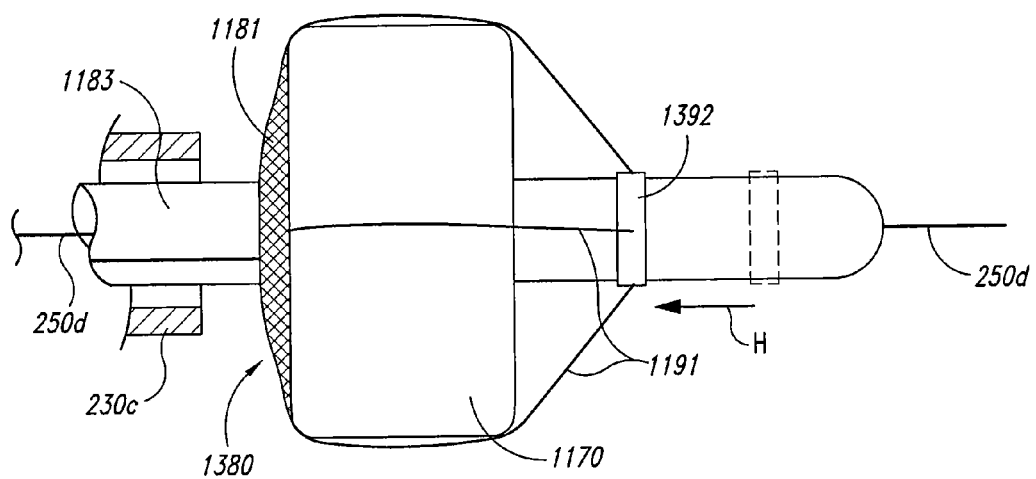

FIG. 13 illustrates an electrode device 1380 that is somewhat similar to the electrode device 1280 described above, but instead of the conductive material 1181 sliding at a sliding interface 1292, the electrode support lines 1191 are attached to a slider 1392 so as to slide relative to the actuator 1183 when the electrode device 1380 is deployed. In at least some cases, the sliding action provided by the slider 1392 can allow the conductive material 1181 to take on a flatter shape when deployed, as discussed above with reference to FIG. 12.

Figure 14:
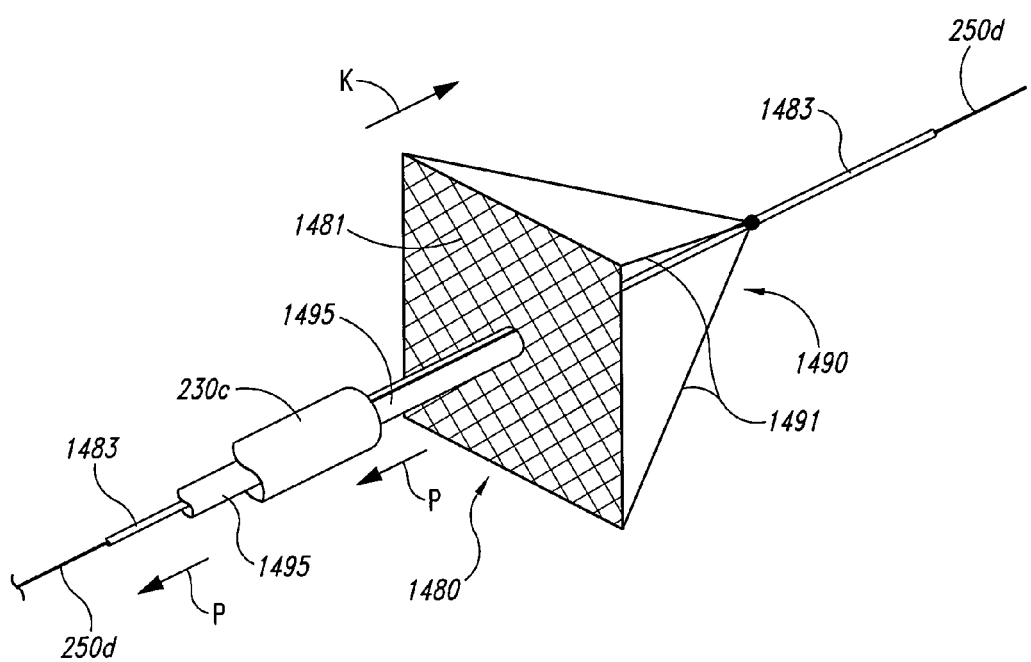
FIG. 14 illustrates an electrode device that is deployed in an umbrella-like fashion in accordance with another embodiment of the disclosure.

FIG. 14 illustrates an electrode device 1480 that is similar in some respects to the electrode device 980 described above with reference to FIGS. 9A-9B, but that deploys and retracts in a sense generally opposite to that described above with reference to FIGS. 9A-9B. For example, the electrode device 1480 can include a conductive material 1481 attached to an actuator 1483 with a support structure 1490 that includes multiple flexible struts 1491. The conductive material 1481 can also be attached to a retractor 1495. The struts 1491 can be biased to the position shown in FIG. 14, and can lie generally parallel to the guidewire 250d when stowed. When the electrode device 1480 is deployed from the electrode catheter 230c as indicated by arrow K, the struts 1491 can spring outwardly to the position shown in FIG. 14, unfurling the conductive material 1481. To retract the electrode device 1480, the practitioner can draw the retractor 1495 in a proximal direction P, pulling the conductive material 1481 and the struts 1491 inwardly toward the actuator 1483 and the guidewire 250d. Once the struts 1491 are aligned with the guidewire 250d, the practitioner can move the retractor 1495 and the actuator 1483 as a unit in the proximal direction P to draw the electrode device 1480 into the electrode catheter 230c.

FIG. 15A is a partially schematic, cross-sectional side view of an electrode device 1580 configured in accordance with another embodiment of the disclosure. FIG. 15B is a partially schematic, end view of a portion of the electrode device 1580 shown in FIG. 15A. With reference to FIG. 15A, the electrode device 1580 can include a tubular portion 1596 connected to an electrode actuator 1583, and fingers 1597 that extend from the tubular portion 1596. In a particular embodiment, the fingers 1597 can be manufactured by slitting the tubular portion 1596, and bending the fingers 1597 in an outward direction. When the electrode device 1580 is stowed, the walls of the electrode catheter 230c can force the fingers 1597 into axial alignment with the guidewire 250d. When the electrode device 1580 is deployed, the fingers 1597 can expand radially outwardly as shown in FIG. 15A. An inflatable member 1570 (e.g., a balloon) can be positioned adjacent to the electrode device 1580 to provide support for the electrode device 1580 when the electrode device 1580 is clamped against the adjacent septal tissue. The inflatable member 1570 can include an inflatable member actuator 1571 that provides an inflation medium (e.g., saline) to the inflatable member 1570, and that can be used to draw the inflatable member 1570 proximally against the electrode device 1580. FIG. 15B illustrates an end view of the electrode device 1580 (without the inflatable member 1570), showing the fingers 1597 in the deployed position.

FIGS. 16A-20B illustrate electrode devices having tubular portions and outwardly splayed fingers or flanges in accordance with further embodiments of the disclosure. For example, FIGS. 16A and 16B illustrate side and end views, respectively, of an electrode device 1680 that includes an outer tubular portion 1696a having outer fingers 1697a and a nested inner tubular portion 1696b positioned annularly inwardly from the outer tubular portion 1696a and having inner fingers 1697b. The combination of the outer and inner fingers 1697a, 1697b can increase the conductive surface area presented to the septal tissue when the electrode device 1680 is deployed.

Figure 17A:
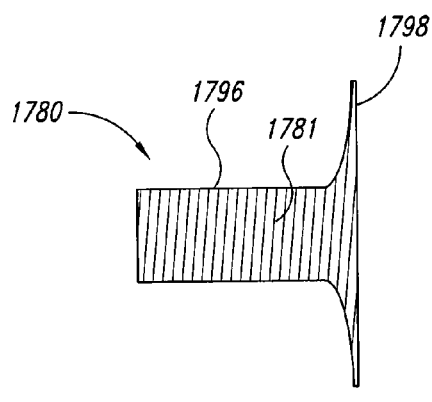
FIGS. 17A-17B illustrate an electrode device having a spiral wound tubular portion and associated flange in accordance with an embodiment of the disclosure.
Figure 17B:
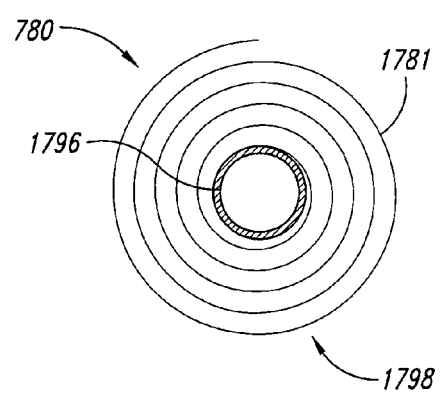
Figure 18A:
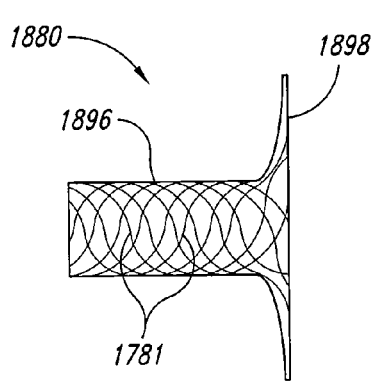
FIGS. 18A-18B illustrate an electrode device having a woven tubular portion and associated flange in accordance with an embodiment of the disclosure.
Figure 18B:
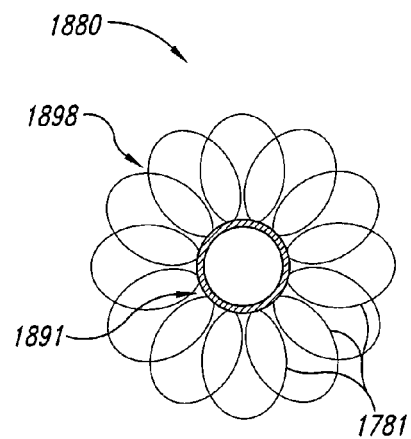

FIGS. 17A and 17B illustrate side and end views, respectively, of an electrode device 1780 formed by winding a conductive filament 1781 into a tubular portion 1796 and a flange 1798. In this embodiment, the electrode device 1780 can include a single filament of conductive material that is wound in a helical fashion to form both the tubular portion 1796 and the flange 1798. In other embodiments, filamentous conductive material can form electrode devices having generally the same shape as is shown in FIGS. 17A and 17B, with different construction techniques. For example, FIGS. 18A and 18B illustrate an electrode device 1880 having a tubular portion 1896 and a flange 1898 formed by weaving conductive filaments 1781. In FIGS. 19A-19B, the illustrated electrode device 1980 includes a tubular portion 1996 and a flange 1998 formed by a knitting process. In FIGS. 20A-20B, the illustrated electrode device 2080 includes a tubular portion 2096 and flange 2098 formed from a flat pattern rather than spiral weave pattern.

F. Systems and Techniques for Clamping Tissue

Figure 21:
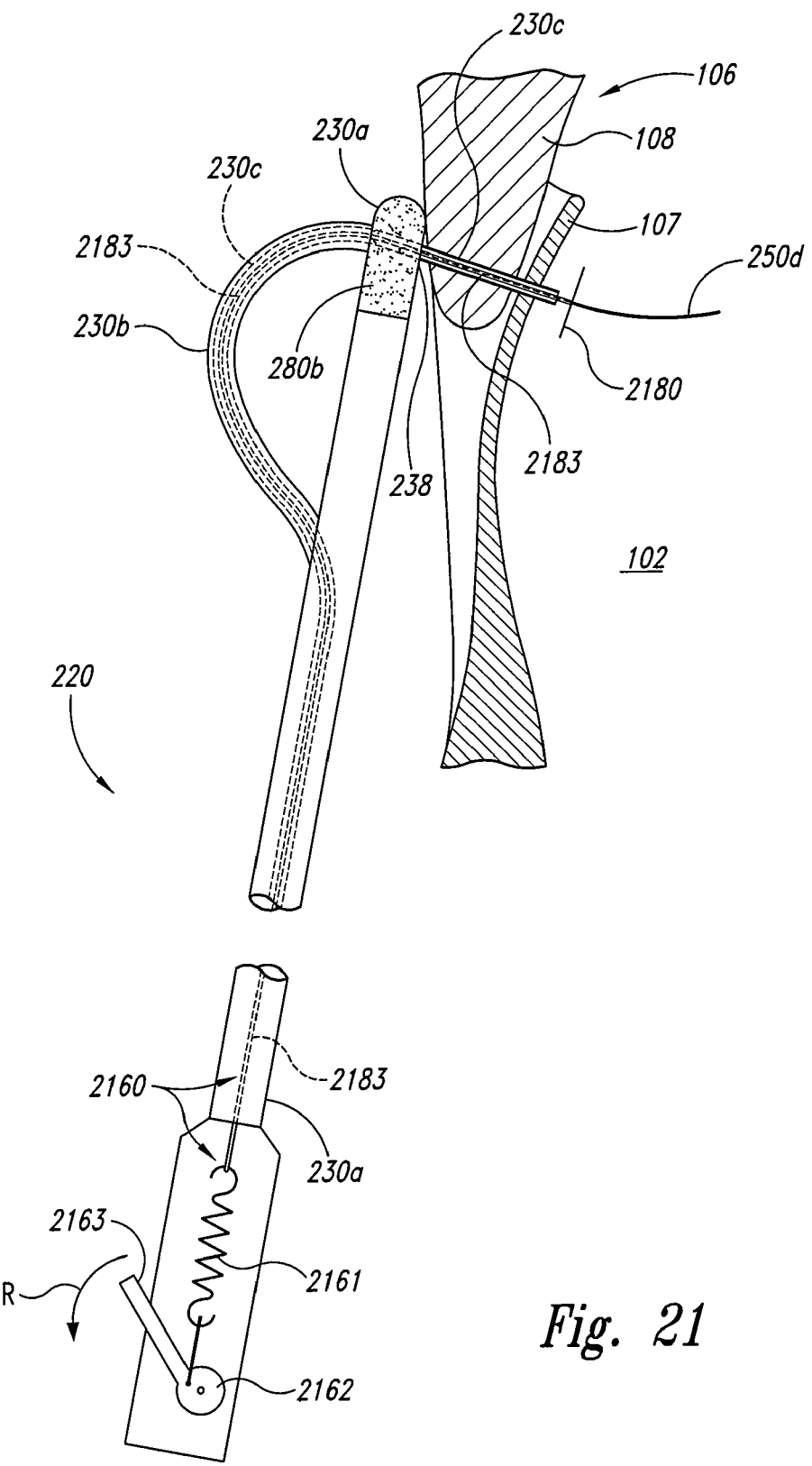
FIG. 21 is a partially schematic, cross-sectional illustration of a catheter arranged to apply a compressive force on an electrode device in accordance with a particular embodiment of the disclosure.

In particular embodiments, the tissue sealed or fused by the electrode or other energy transmission device can be clamped as it is heated, so as to promote tissue sealing. FIG. 21 is a partially schematic illustration of an embodiment of the system 220 that includes a compression device 2160 for clamping the primum 107 and the secundum 108 between an electrode device 2180 and the delivery catheter 230a. The delivery catheter 230a can have a configuration generally similar to that described above with reference to FIG. 3H and can accordingly include a backstop surface 238 positioned proximate to the secundum 108. The positioning catheter 230b can then be positioned to deploy the electrode catheter 230c along the penetrating guidewire 250d through the septum 106 (e.g., the secundum 108 and the primum 107, or just the primum 107). An electrode device 2180, shown schematically in FIG. 21, can then be deployed in the right atrium 102.

The electrode device 2180 can have a generally flat, not-cutting surface facing toward the primum 107, suitable for tissue sealing and/or fusing. The compression device 2160 can be operatively coupled between the electrode device 2180 and one of the catheters 230a-230c (e.g., the delivery catheter 230a). For example, the compression device 2160 can include an actuator 2183 (e.g., a cable) that is connected to the electrode 2180 and that extends through the electrode catheter 230c, the positioning catheter 230b, and the delivery catheter 230a and is connected to a compression member 2161. In a particular embodiment, the compression member 2161 includes a spring connected to a cam 2162 that is operated via a cam handle 2163 and is accordingly located outside the patient for manipulation by the practitioner. With the electrode device 2180 deployed, the practitioner can rotate the cam handle 2163, as indicated by arrow R, to stretch the compression member 2161, thereby applying an axial tension to the actuator 2183 and compressing the septum 106 between the electrode device 2180 and the backstop surface 238.

The amount of force and/or pressure provided by the compression device 2160 can be selected based on a variety of factors, including the particular patient physiology and the particular electrode device configuration. For example, in a particular embodiment, the pressure applied to the septal tissue by the compression device 2160 can be from about 0.1 psig to about 15 psig. In a particular embodiment, the pressure can be from about 0.5 psig to about 5 psig, and in a further particular embodiment, about 8 psig. When the electrode device 2180 has a petal-shaped configuration (as shown in FIG. 8C) with an overall diameter of about 12 mm, the load applied to the electrode device 2180 can be in the range of from about 0.5 pounds to about 2.0 pounds, and in a particular embodiment, about 1.4 pounds.

One advantage of embodiments including the foregoing feature is that they can improve the efficiency with which a seal is created between the secundum 108 and the primum 107. For example, clamping the tissue to be sealed can improve the strength of the seal by (a) reducing the convective cooling provided by blood in the tissue, (b) raising the boiling point of tissue water, (c) raising the temperature for evolution of entrained tissue gases, (d) improving thermal conductivity, and/or (e) increasing tissue adhesion at the tissue interface. In addition, the primum 107 and/or the secundum 108 may shrink during the heating and fusing process, and the compression device 2160 can maintain a compressive force on these two tissues throughout the sealing process, even if the tissues tend to shrink. For example, the compression device 2160 can apply a generally constant force over a distance several times the thickness of the septum 106, e.g., over a distance of about 20 mm. Accordingly, the compression device 2160 can maintain a generally constant force on the tissue during at least some phases of operation, and can be adjustable to vary the compressive force applied to the tissue (e.g., between a first clamping force and a second lesser or zero clamping force) during other phases of operation. By applying a constant force over a particular range, embodiments of the compression device can also be suitable for sealing tissues (e.g., septal tissues) having a variety of thicknesses. Accordingly, such devices can be used with a wide variety of patient cardiac topologies.

In other embodiments, other devices and/or techniques can be used to apply tension to the actuator 2183 and compression to the secundum 108 and the primum 107. For example, the compression device 2160 can be activated until the two tissues are "snugged" against each other, and then further tightened or activated by extending the spring a predetermined distance, corresponding to a predetermined load. In other embodiments, the actuator 2183 itself can be resilient, compliant, and/or stretchable, and can provide the compressive force on the septum 106. Accordingly, the compression device 2160 need not include a compression member 2161 in addition to the actuator 2183. In this and other embodiments, at least part of the compression device can be located inside the patient, e.g., at the working portion or other portions of the catheter.

Figure 22:
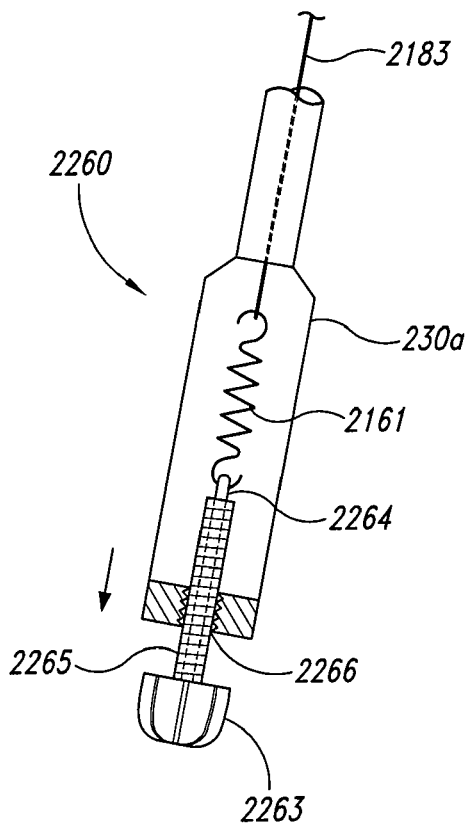
FIG. 22 is a partially schematic illustration of a threaded device for applying a compressive force on an electrode device in accordance with an embodiment of the disclosure.

FIG. 22 illustrates a compression device 2260 that includes a threaded shaft 2265 connected to the compression member 2161 (e.g., a spring) with a swivel joint 2264. The threaded shaft 2265 is connected to a handle 2263 and is received in a threaded opening 2266 of the delivery catheter 230a. When the practitioner rotates the handle 2263 counterclockwise, the threaded shaft 2265 moves outwardly from the delivery catheter 230a, applying a tension to the compression member 2161 and the actuator 2183 so as to clamp the primum 107 (FIG. 21) and the secundum 108 (FIG. 21). The compressive force can be released by rotating the handle 2263 in the opposite direction. As discussed above with reference to FIG. 21, the actuator 2183 can be made stretchable and the spring can be eliminated in another embodiment. The compression device 2260 can include detents and/or circumferential markings to indicate to the practitioner how much force (or an equivalent, e.g., stretch distance) is being applied to the actuator 2183.

Figure 23:
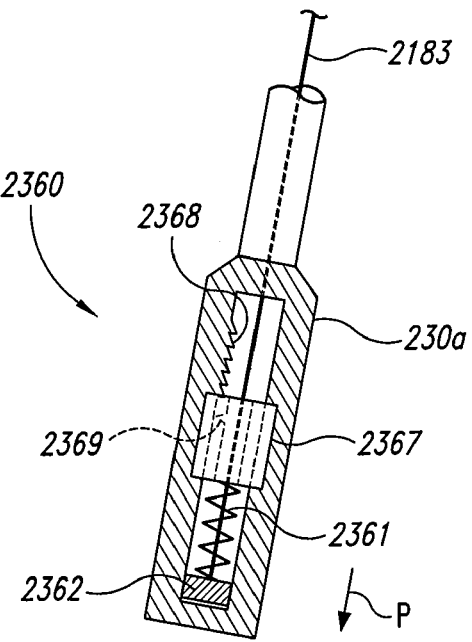
FIG. 23 is a partially schematic, cross-sectional illustration of an arrangement that includes a slider for applying a compressive force on an electrode device in accordance with yet another embodiment of the disclosure.

FIG. 23 illustrates a compression device 2360 that in turn includes a slider 2367 having a pawl 2369 that engages with one or more teeth or notches 2368 carried by the delivery catheter 230a. The compression device 2360 can further include a piston (e.g. non-sealing piston) 2362 and a compression member 2361 (e.g., a spring between the piston 2362 and the slider 2367). The piston 2362 can be attached to the actuator 2183, which passes through a passageway in the slider 2367. The practitioner can move the slider 2367 in a proximal direction indicated by arrow P to compress the compression member 2361, which applies a tension to the actuator 2183, which in turn compresses the primum 107 (FIG. 21) and secundum 108 (FIG. 21). This arrangement can provide a stop (or multiple stops) along the path of the slider 2367 to prevent the practitioner from inadvertently clamping the tissue too tightly, and/or to provide a final stop that prevents the practitioner from over-compressing the septal tissue.

Any of the foregoing devices described above with reference to FIGS. 21-23 can be configured as "two position" devices (e.g., having a "compressed" position and an "uncompressed" position), or as a variable position device (e.g., having intermediate positions). The actuation forces can be applied by devices other than springs. For example, the actuation forces can be provided by pneumatic or hydraulic actuators, which are suitable for applying a constant force over a selected actuation distance.

From the foregoing, it will be appreciated that specific embodiments of the disclosure have been described herein for purposes of illustration, but that various modifications may be made from these embodiments. For example, as discussed above, the energy transmitter can include devices other than RF electrodes, e.g., microwave devices. When the energy transmitter includes electrodes, the electrodes can be arranged in a monopolar manner or a bipolar manner as described above, or the electrodes can be arranged in another multipolar manner (e.g., a quadrapolar manner). For example, the spheroidal electrode shown in FIG. 8J can include multiple neighboring portions (in a circumferential direction) that are electrically insulated from each other. Certain aspects of the foregoing embodiments may be applied to tissues other than septal tissue (e.g., other target tissues), and/or in a manner to treat patient conditions other than PFOs. For example, in some cases, aspects of the foregoing embodiments can be used for procedures other than sealing or closing a PFO, and/or procedures other than tissue fusing. Representative procedures include percutaneous aortic or mitral valve treatments and/or implants, left atrial appendage closures, aortic aneurysm repair, artery or vein treatment, and electrophysiology ablation therapies for correcting EKG rhythm disorders.

Certain aspects of the disclosure described in the context of particular embodiments may be combined or eliminated in other embodiments. For example, a catheter system in accordance with particular embodiments may include only some of the foregoing devices and features, and other systems may include devices and features in addition to those disclosed above. In a further particular example, features of the guidewire advancers discussed above with reference to FIGS. 7A-7F may be included in the electrode clamping devices described with reference to FIGS. 21-23, and/or vice versa. Electrode devices other than those shown in FIGS. 8H-8I can include the fluid delivery ports shown in FIGS. 8H-8I. Further, while advantages associated with certain embodiments have been described in the context of those embodiments, other embodiments may also exhibit such advantages, and not all embodiments need necessarily exhibit such advantages. Accordingly, the disclosure can include other embodiments not shown or described above. The following examples provide representative embodiments.

We claim:

1. A method for treating a patient, comprising:
    positioning a tissue penetrating guidewire adjacent to a cardiac septum;
    directing pulses of energy to the guidewire;
    advancing the guidewire into and through the septum by moving the guidewire in a distal direction in a series of discrete steps, with individual steps being of a predetermined distance measured outside the patient's body;
    receiving an indication of an impedance of a conductive path that includes the guidewire;
    halting advancement of the guidewire when the impedance changes by or to a target value; and
    passing a catheter over the guidewire after the guidewire has passed through the septum.

2. The method of claim 1 wherein advancing the guidewire includes manually advancing the guidewire.

3. The method of claim 1 wherein advancing the guidewire includes automatically advancing the guidewire via a powered device.

4. The method of claim 1 wherein advancing the guidewire includes automatically advancing the guidewire via a constant force spring.

5. The method of claim 1, further comprising halting movement of the guidewire at the conclusion of individual discrete steps.

6. The method of claim 1 wherein advancing the guidewire includes placing an axial load on the guidewire with an individual discrete step, and wherein directing pulses of energy to the guidewire includes directing a pulse train causing the guidewire to heat the septum, penetrate into the septum, and release the axial load.

7. The method of claim 1 wherein directing pulses of energy includes directing a single pulse train after moving the guidewire by a single discrete step.

8. The method of claim 1 wherein moving the guidewire includes moving the guidewire in a series of discrete steps of about one millimeter.

9. The method of claim 1, further comprising selecting the predetermined distance.

10. The method of claim 1 wherein passing a catheter over the guidewire includes passing an energy transmitter catheter over the guidewire.

11. The method of claim 10 wherein the energy transmitter catheter includes at least one electrode, and wherein the method further comprises at least partially sealing an opening in the septum by applying electrical energy to at least one electrode.

12. The method of claim 10 wherein the guidewire is connected to an actuator, and wherein moving the guidewire includes linearly translating the actuator.

13. The method of claim 10 wherein moving the guidewire includes rotating a knob that is threadably engaged with the actuator.

14. The method of claim 1, further comprising:
    controlling advancement of the guidewire based at least in part on the impedance indication;
    upon receiving an indication that the guidewire has contacted septal tissue, applying an axial force to the guidewire to deflect the septal tissue and deflect a spring coupled to the guidewire; and
    applying electrical energy to the guidewire to ablate a hole in the septal tissue and release the deflection in the spring and the deflection in the septal tissue.

15. The method of claim 1 wherein advancing the guidewire includes advancing the guidewire at an angle of from about 80° to about 135° relative to the septum.

16. The method of claim 15 wherein advancing the guidewire includes advancing the guidewire at an angle of about 105° relative to the septum.

17. The method of claim 1, further comprising:
    directing the pulses of energy from the guidewire to the septum and to a return electrode in a bipolar manner while the return electrode is positioned in the patient's heart.

18. The method of claim 17, further comprising:
    positioning a catheter in the patient's right atrium, the catheter carrying the guidewire and the return electrode; and
    deploying the guidewire from the catheter, wherein advancing the guidewire includes advancing the guidewire from the right atrium through the septum to the left atrium while the return electrode remains in the right atrium.

19. The method of claim 17, further comprising passing a catheter over the guidewire after the guidewire has passed through the septum.

20. The method of claim 19 wherein passing a catheter includes passing an electrode delivery catheter, and wherein the method further comprises at least partially sealing a PFO at the cardiac septum by directing energy from an electrode carried by the electrode delivery catheter to the return electrode in a bipolar manner while the return electrode is positioned in the patient's heart.

21. A method for treating a patient, comprising:
positioning a tissue penetrating guidewire adjacent to a cardiac septum;
directing pulses of energy to the guidewire;
advancing the guidewire into and through the septum by moving the guidewire in a distal direction in a series of discrete steps, with individual steps being of a predetermined distance measured outside the patient's body, wherein advancing the guidewire includes placing an axial load on the guidewire with an individual discrete step, and wherein directing pulses of energy to the guidewire includes directing a pulse train causing the guidewire to heat the septum, penetrate into the septum, and release the axial load; and
passing a catheter over the guidewire after the guidewire has passed through the septum.

22. The method of claim 21 wherein advancing the guidewire includes manually advancing the guidewire.

23. The method of claim 21 wherein advancing the guidewire includes automatically advancing the guidewire via a powered device.

24. The method of claim 21, further comprising halting movement of the guidewire at the conclusion of individual discrete steps.

25. The method of claim 21, further comprising:
receiving an indication of an impedance of a conductive path that includes the guidewire; and
halting advancement of the guidewire when the impedance changes by or to a target value.

26. The method of claim 21 wherein directing pulses of energy includes directing a single pulse train after moving the guidewire by a single discrete step.

27. The method of claim 21 wherein passing a catheter over the guidewire includes passing an energy transmitter catheter over the guidewire.

28. The method of claim 27 wherein the energy transmitter catheter includes at least one electrode, and wherein the method further comprises at least partially sealing an opening in the septum by applying electrical energy to at least one electrode.

29. The method of claim 27 wherein the guidewire is connected to an actuator, and wherein moving the guidewire includes linearly translating the actuator.

30. The method of claim 27 wherein moving the guidewire includes rotating a knob that is threadably engaged with the actuator.

31. The method of claim 21, further comprising:
receiving an indication of an impedance of a conductive path that includes the guidewire;
controlling advancement of the guidewire based at least in part on the impedance indication;
upon receiving an indication that the guidewire has contacted septal tissue, applying the axial load to the guidewire to deflect the septal tissue and deflect a spring coupled to the guidewire; and
wherein directing pulses of energy includes applying electrical energy to the guidewire to ablate a hole in the septal tissue and release the deflection in the spring and the deflection in the septal tissue.

32. A method for treating a patient, comprising:
receiving an indication of an impedance of a conductive path that includes a tissue penetrating guidewire;
controlling advancement of the guidewire based at least in part on the impedance indication;
positioning the tissue penetrating guidewire adjacent to a cardiac septum;
upon receiving an indication that the guidewire has contacted septal tissue, applying an axial force to the guidewire to deflect the septal tissue and deflect a spring coupled to the guidewire;
directing pulses of energy to the guidewire;
advancing the guidewire into and through the septum by moving the guidewire in a distal direction in a series of discrete steps, with individual steps being of a predetermined distance measured outside the patient's body, where advancing the guidewire includes applying electrical energy to the guidewire to ablate a hole in the septal tissue and release the deflection in the spring and the deflection in the septal tissue; and
passing a catheter over the guidewire after the guidewire has passed through the septum.

33. The method of claim 32 wherein advancing the guidewire includes manually advancing the guidewire.

34. The method of claim 32 wherein advancing the guidewire includes automatically advancing the guidewire via a powered device.

35. The method of claim 32, further comprising halting movement of the guidewire at the conclusion of individual discrete steps.

36. The method of claim 32, further comprising:
halting advancement of the guidewire when the impedance changes by or to a target value.

37. The method of claim 32 wherein passing a catheter over the guidewire includes passing an energy transmitter catheter over the guidewire.

38. The method of claim 37 wherein the energy transmitter catheter includes at least one electrode, and wherein the method further comprises at least partially sealing an opening in the septum by applying electrical energy to at least one electrode.

39. The method of claim 37 wherein the guidewire is connected to an actuator, and wherein moving the guidewire includes linearly translating the actuator.

40. The method of claim 37 wherein moving the guidewire includes rotating a knob that is threadably engaged with the actuator.

* * * * *